(12) United States Patent
Andersen et al.

(10) Patent No.: US 12,110,510 B2
(45) Date of Patent: Oct. 8, 2024

(54) FUNCTIONAL CORTICO-SPINAL-MUSCLE ASSEMBLED SPHEROIDS

(71) Applicant: The Board of Trustees of the Leland Stanford Junior University, Stanford, CA (US)

(72) Inventors: Jimena Andersen, Palo Alto, CA (US); Sergiu P. Pasca, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 909 days.

(21) Appl. No.: 17/253,038

(22) PCT Filed: Jun. 20, 2019

(86) PCT No.: PCT/US2019/038307
§ 371 (c)(1),
(2) Date: Dec. 16, 2020

(87) PCT Pub. No.: WO2019/246436
PCT Pub. Date: Dec. 26, 2019

(65) Prior Publication Data
US 2021/0261924 A1 Aug. 26, 2021

Related U.S. Application Data

(60) Provisional application No. 62/688,924, filed on Jun. 22, 2018.

(51) Int. Cl.
*C12N 5/071* (2010.01)
*C12N 5/077* (2010.01)
*C12N 5/0793* (2010.01)
*G01N 33/50* (2006.01)

(52) U.S. Cl.
CPC ......... *C12N 5/0697* (2013.01); *C12N 5/0619* (2013.01); *C12N 5/0658* (2013.01); *G01N 33/5082* (2013.01); *C12N 2500/38* (2013.01); *C12N 2501/01* (2013.01); *C12N 2501/105* (2013.01); *C12N 2501/11* (2013.01); *C12N 2501/115* (2013.01); *C12N 2501/13* (2013.01); *C12N 2501/15* (2013.01); *C12N 2501/41* (2013.01); *C12N 2501/734* (2013.01); *C12N 2501/999* (2013.01); *C12N 2502/081* (2013.01); *C12N 2502/1335* (2013.01); *C12N 2506/45* (2013.01); *C12N 2513/00* (2013.01)

(58) Field of Classification Search
CPC .. C12N 5/0697; C12N 5/0619; C12N 5/0658; C12N 2500/38; C12N 2501/01; C12N 2501/105; C12N 2501/11; C12N 2501/115; C12N 2501/13; C12N 2501/15; C12N 2501/41; C12N 2501/734; C12N 2501/999; C12N 2502/081; C12N 2502/1335; C12N 2506/45; C12N 2513/00; G01N 33/5082

See application file for complete search history.

(56) References Cited

U.S. PATENT DOCUMENTS 10,323,229 B1    6/2019    Li et al.
2018/0282689 A1  10/2018   Andersen et al.
2018/0298333 A1  10/2018   Marton et al.

FOREIGN PATENT DOCUMENTS

WO    WO2017/117547    7/2017

OTHER PUBLICATIONS

Andersen et al. (2020) "Generation of Functional Human 3D Cortico-Motor Assembloids" Cell, Elsevier, Amsterdam NL, 183:7, p. 1913.
Birey et al. (2017) "Assembly of functionally integrated human forebrain spheroids" Nature, 545:7652, pp. 54-59.
Lindborg et al. (2016) "Rapid Induction of Cerebral Organoids From Human Induced Pluripotent Stem Cells Using a Chemically Defined Hydrogel and Defined Cell Culture Medium" Stem Cells Translational Medicine, 5:7 pp. 970-979.
Martins et al. (2020) "Self-organizing 3D Human Trunk Neuromuscular Organzoids" Cell Stem Cell, 26:2, pp. 172-186.
Osaki et al. "Microphysiological 3D model of amyotrophic lateral sclerosis (ALS) from human iPS-derived muscle cells and optogenetic motor neurons" Science Advances, 4: pp. 1-15.
Pasca et al. (2015) "Functional Cortical Neurons and Astrocytes From Human Pluripotent Stem Cells in 3D Culture" Nature Methods, 12:7 pp. 671-678.
Puttonen et al. (2015) "Generation of Functional Neuromuscular Junctions from Human Pluripotent Stem Cell Lines" Frontiers In Cellular Neuroscience, vol. 9.
Sances et al. (2016) "Modeling ALS with motor neurons derived from human induced pluripotent stem cells" Nature Neuroscience, 19:4 pp. 542-553.
Birey et al. (2017) "Assembly of functionally integrated human forebrain spheroids," Nature vol. 545, No. 7652, p. 54-59.
Pasca et al. (2018) "Building three-dimensional human brain organoids," Nature Neuroscience, p. 1 of 1.

*Primary Examiner* — Titilayo Moloye
*Assistant Examiner* — Gillian C. Reglas
(74) *Attorney, Agent, or Firm* — Andrew R. Guzman; Bozicevic, Field & Francis LLP

(57) ABSTRACT

Functional human cortico-spinal-muscle assembled spheroids are generated by in vitro culture. Complete cortico-spinal-muscle spheroids (hCS-hSC-hSkM) are assembled from component cultured cell systems, where each cultured cell system is designed to provide specific sets of neural and/or muscle cells, and which components are functionally integrated in the assembled spheroid.

17 Claims, 28 Drawing Sheets

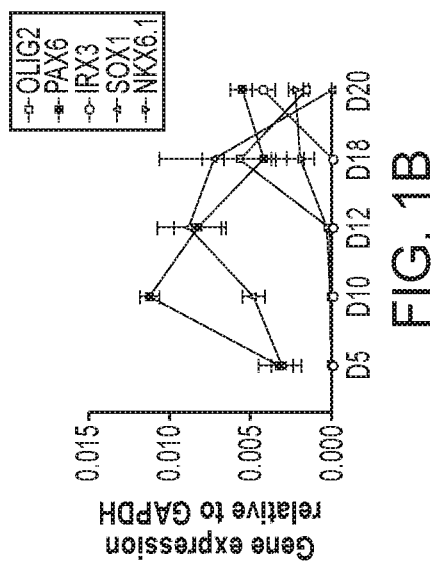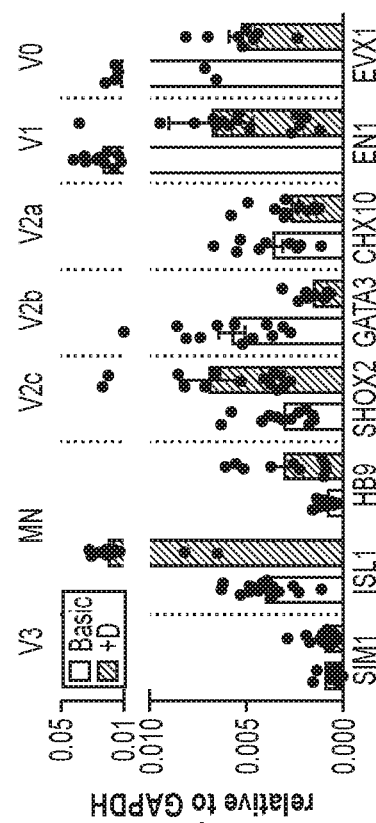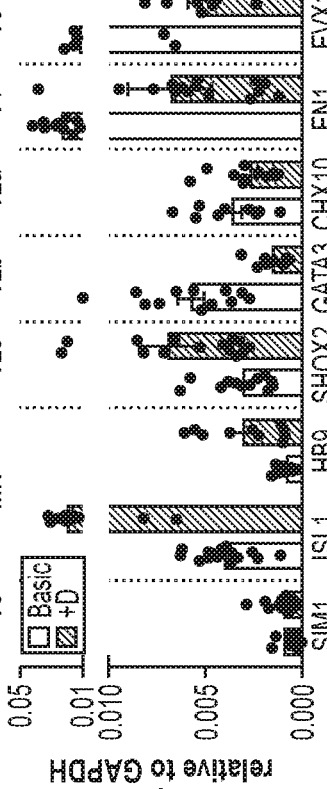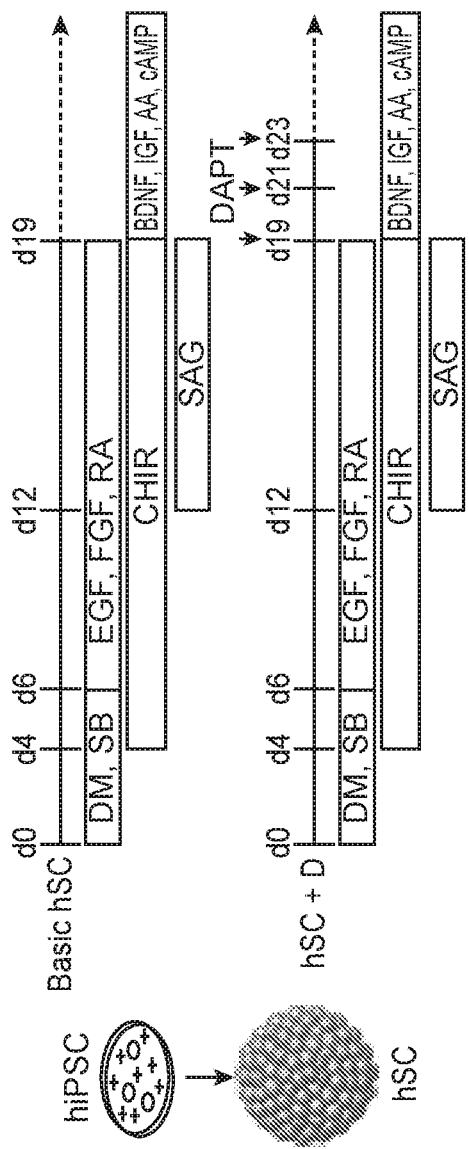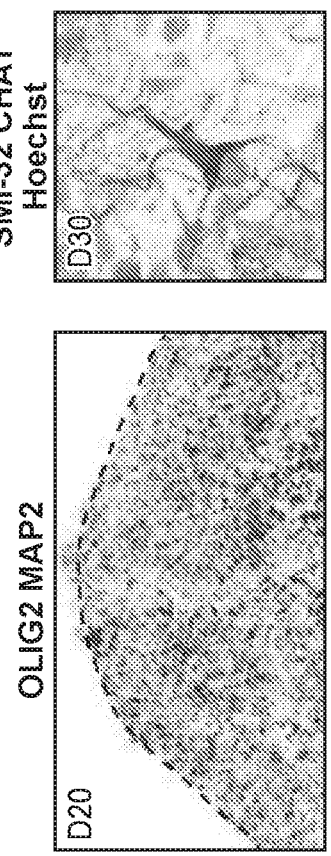
FIG. 1A
FIG. 1B
FIG. 1C
FIG. 1D
FIG. 1E

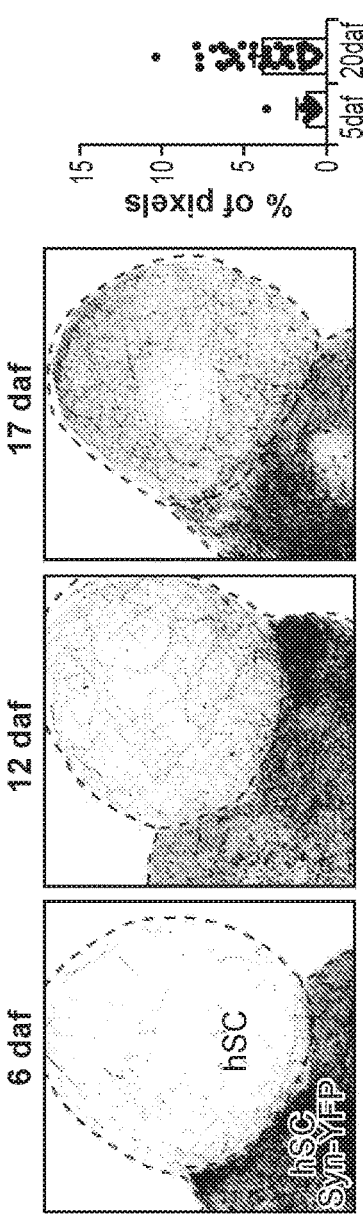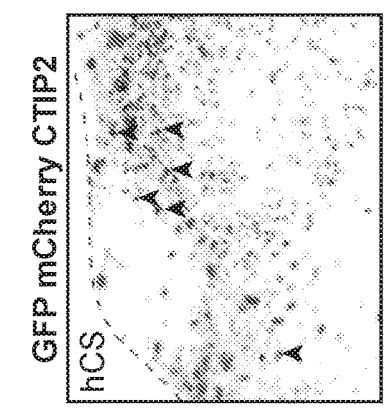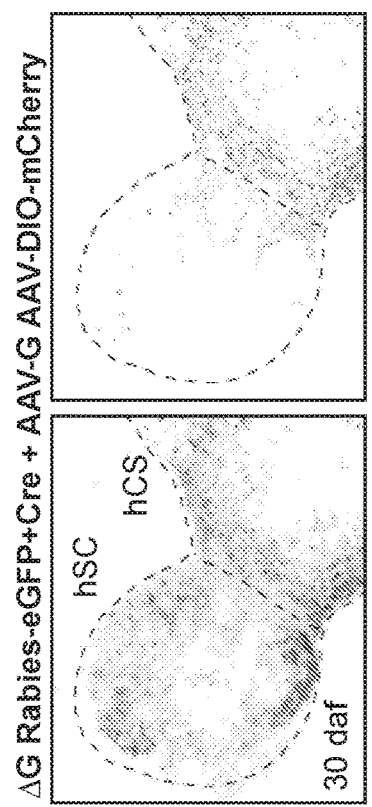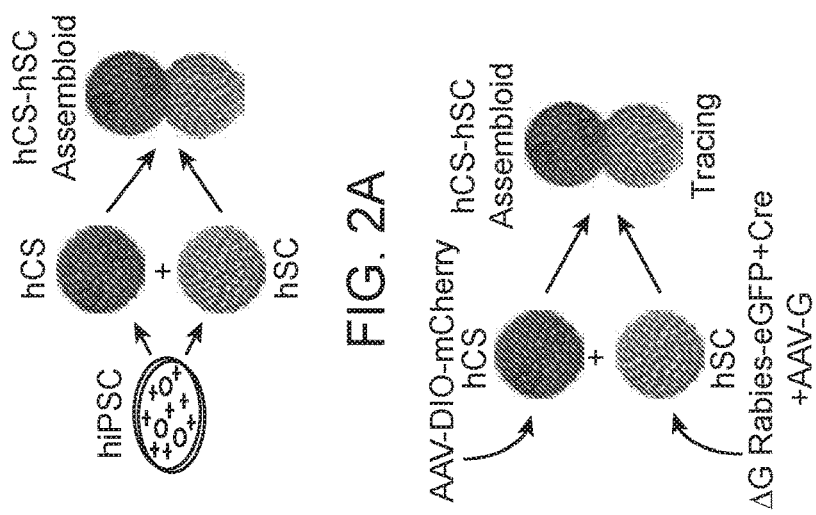

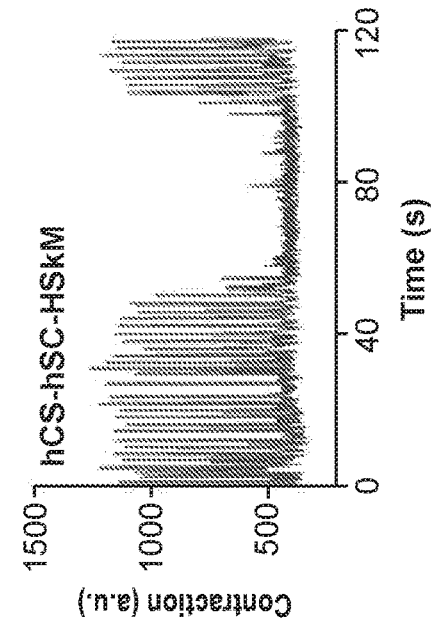
FIG. 3B
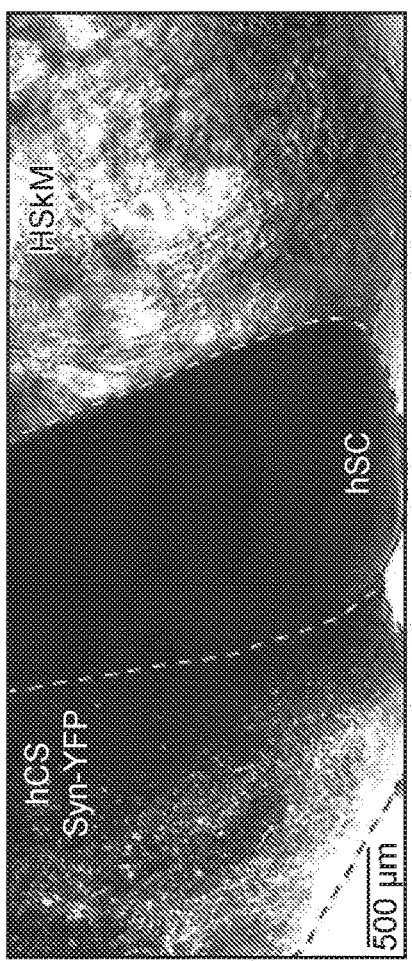
FIG. 3A
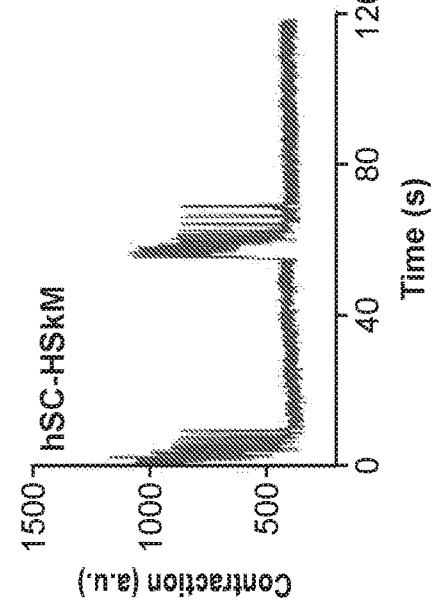
FIG. 3D
FIG. 3E
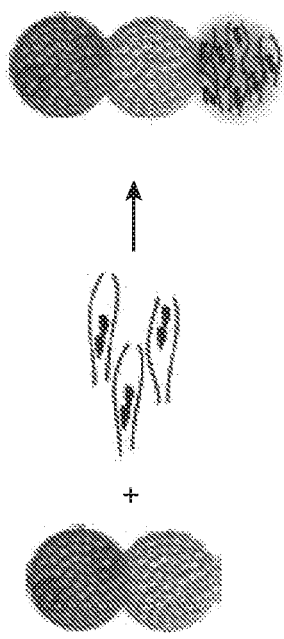
FIG. 3C

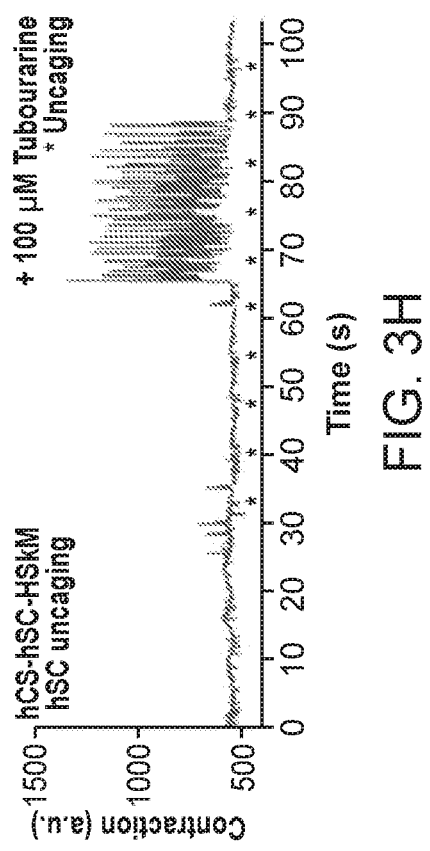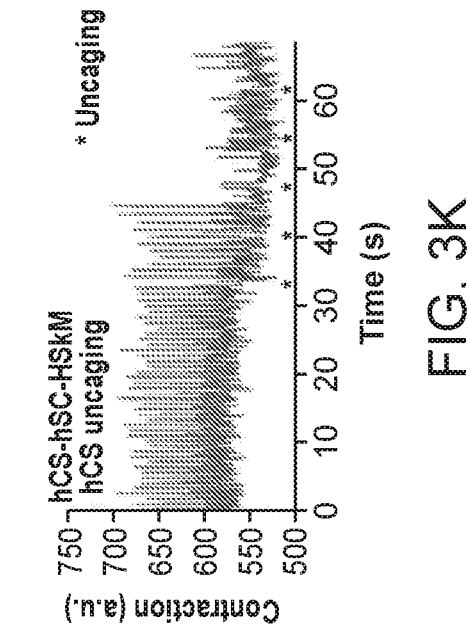
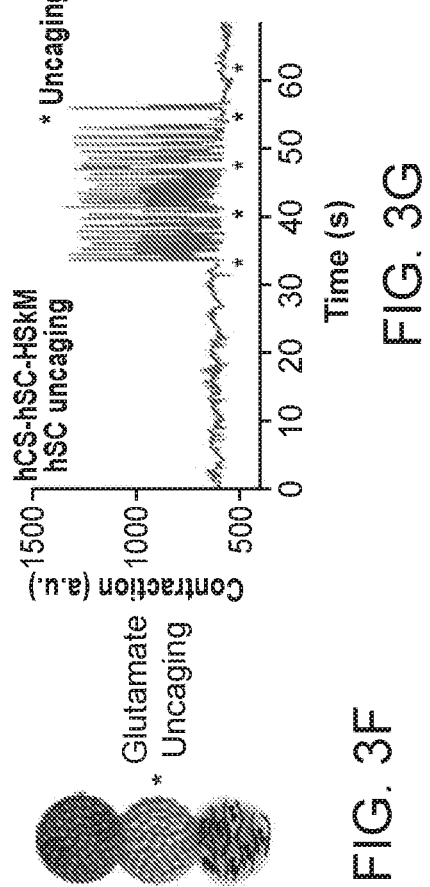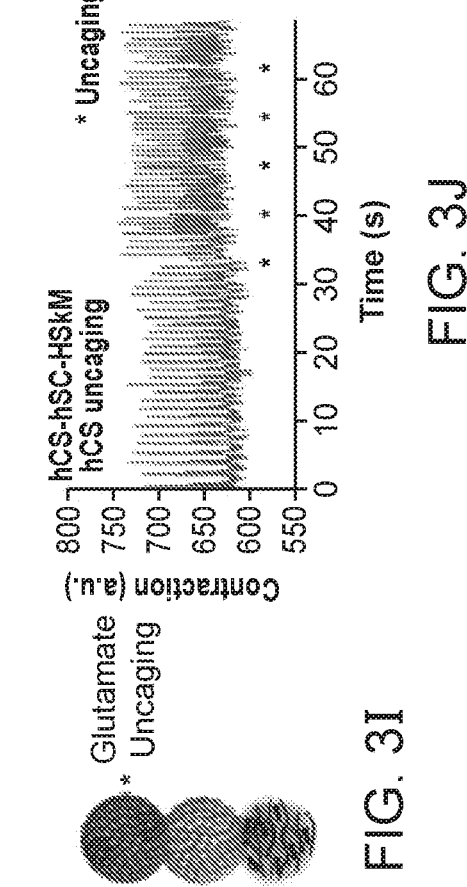
FIG. 3F  FIG. 3G  FIG. 3H
FIG. 3I  FIG. 3J  FIG. 3K

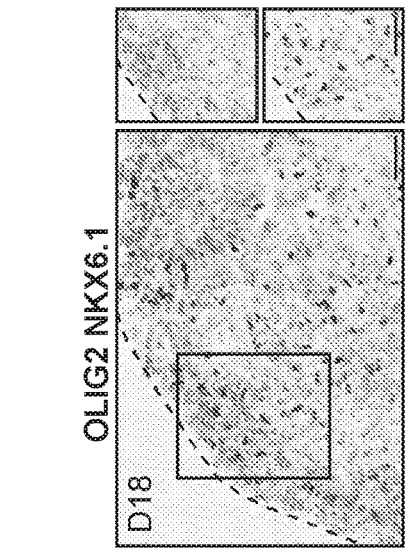
FIG. 4A
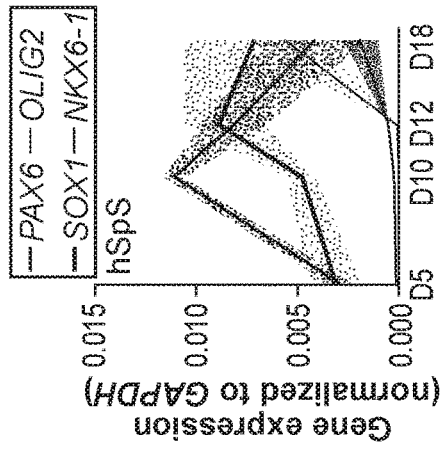
FIG. 4B
FIG. 4C
FIG. 4D
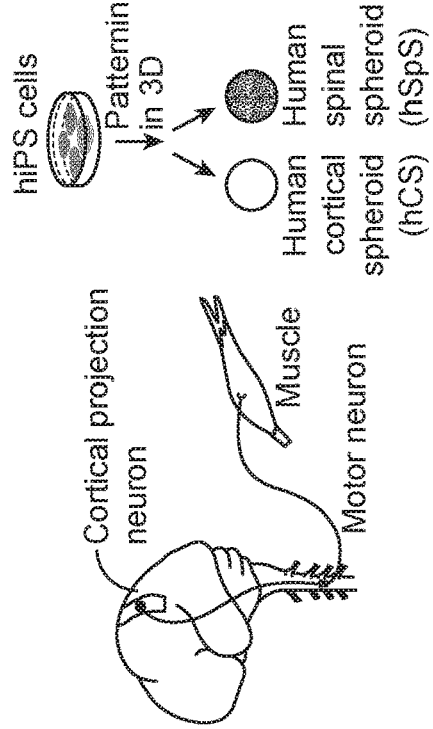
FIG. 4E
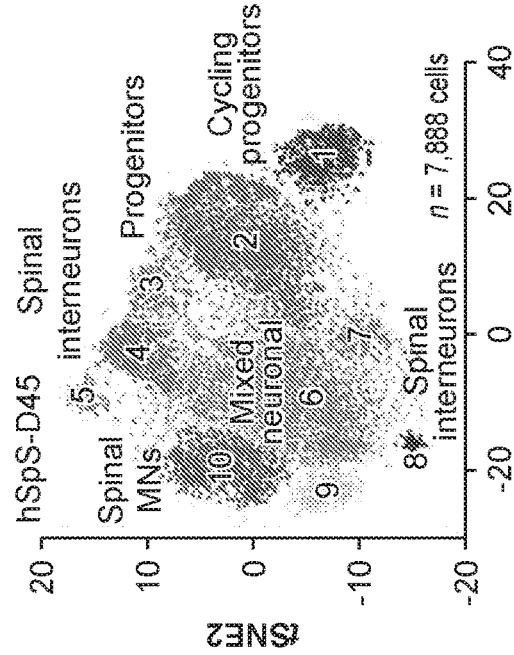
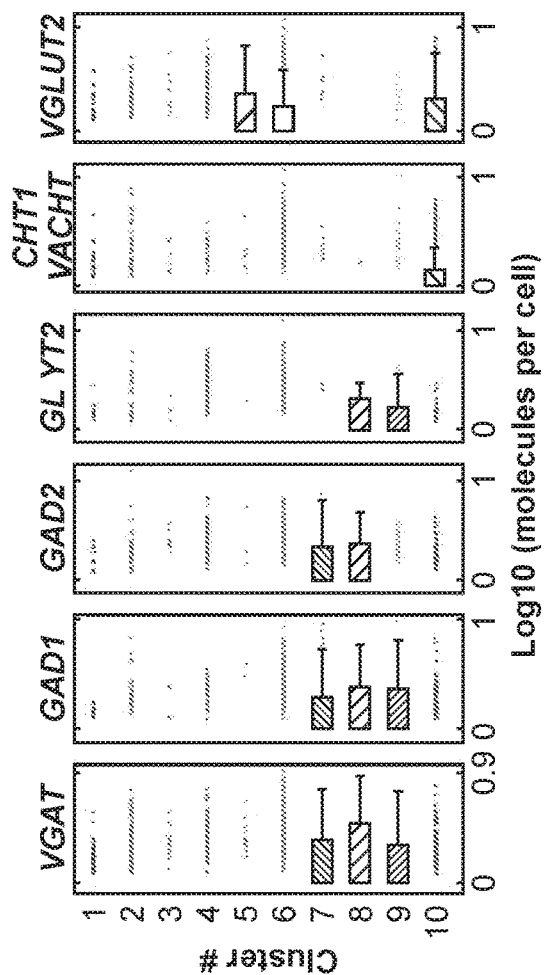
FIG. 4F

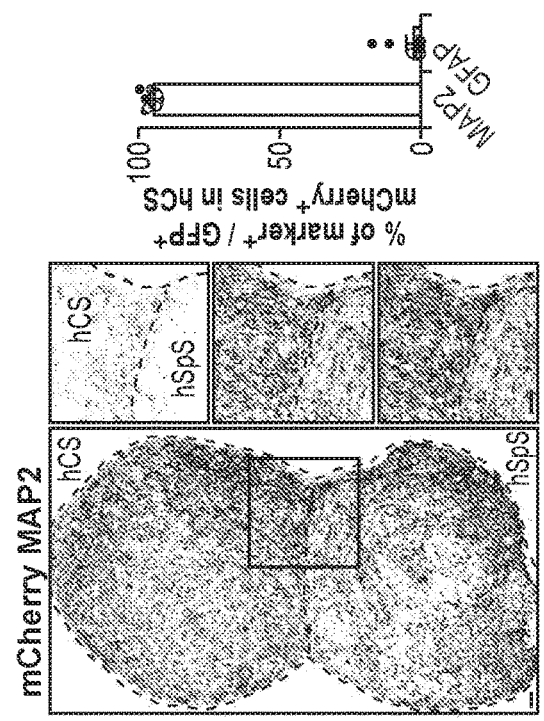
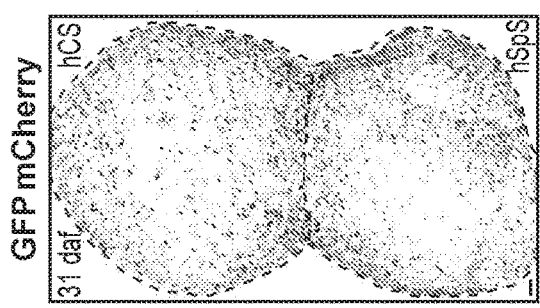
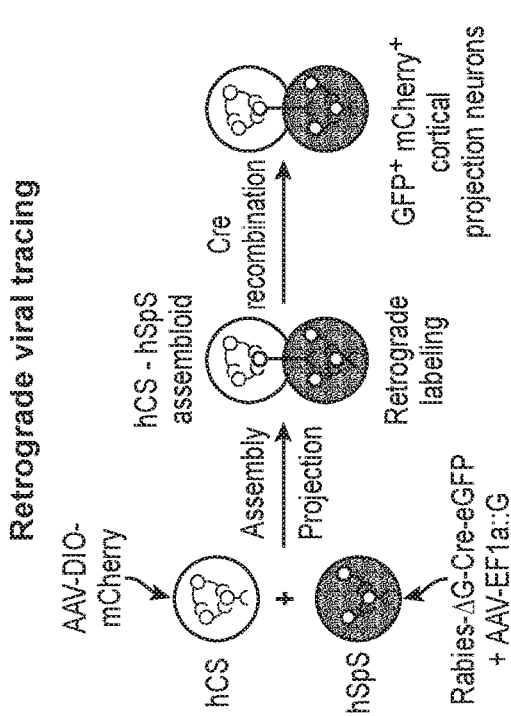
FIG. 5A
FIG. 5B
FIG. 5C
FIG. 5D
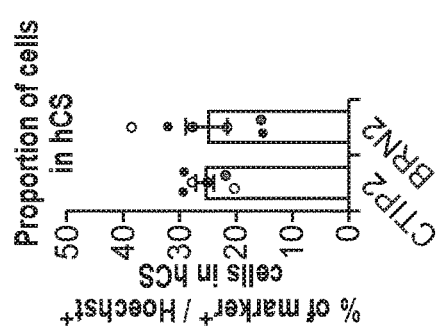
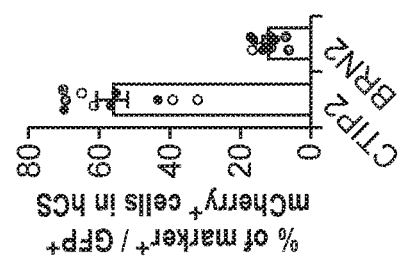
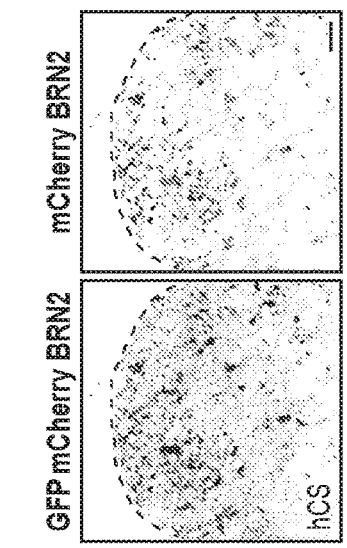
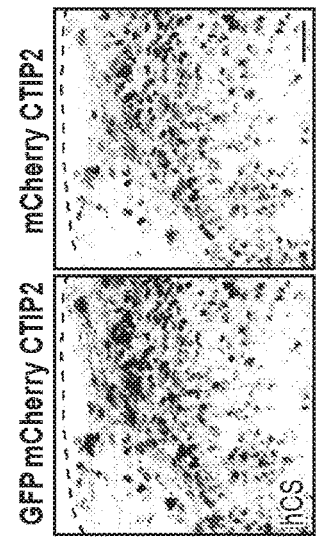
FIG. 5E
FIG. 5F
FIG. 5G
FIG. 5H

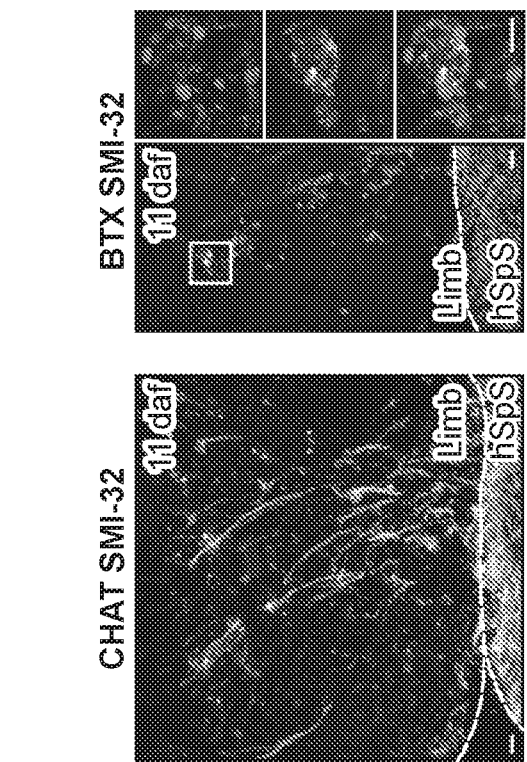
FIG. 6A
FIG. 6B
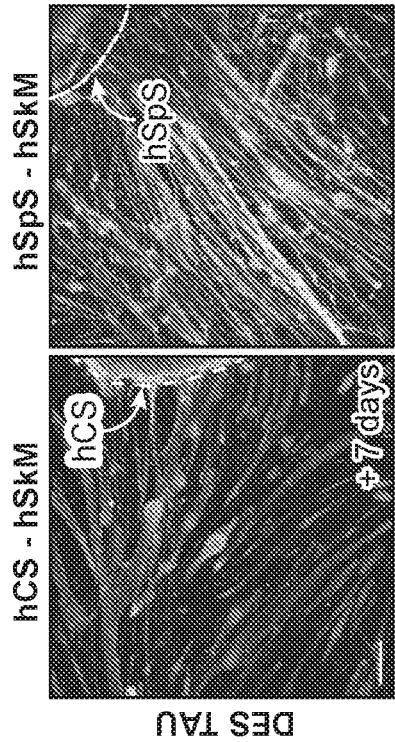
FIG. 6C
FIG. 6D
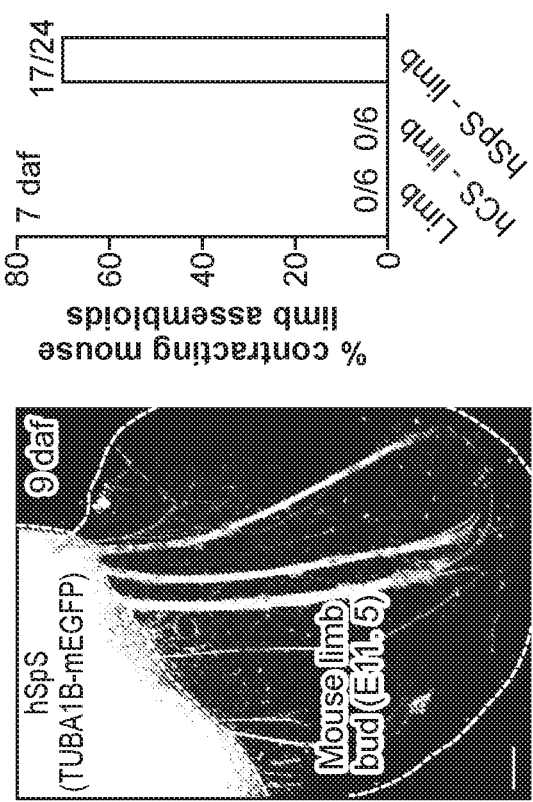
FIG. 6E
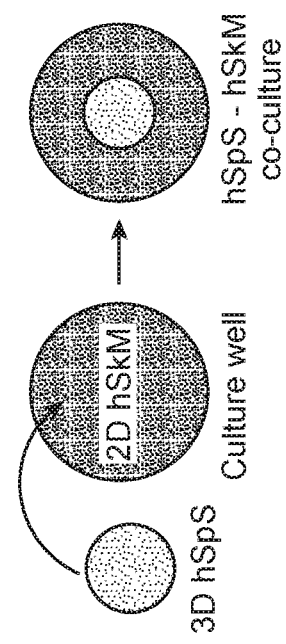
FIG. 6F

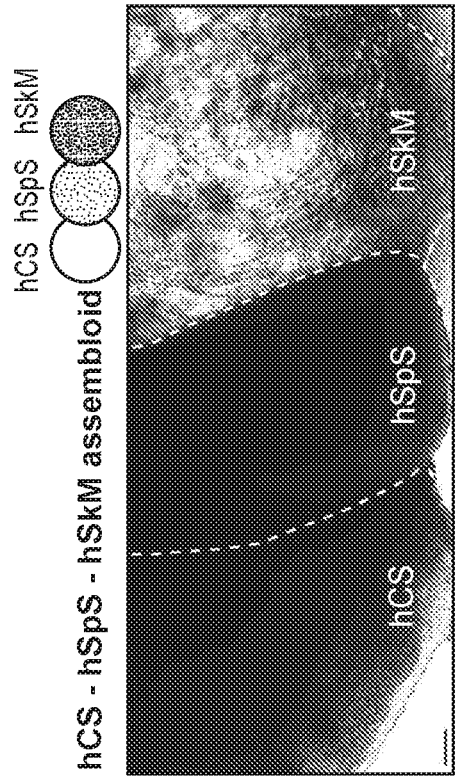
FIG. 7C
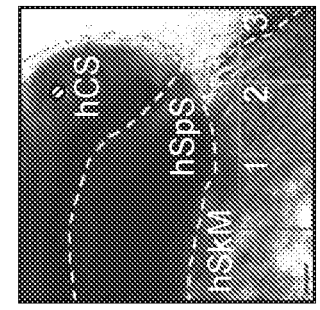
FIG. 7E
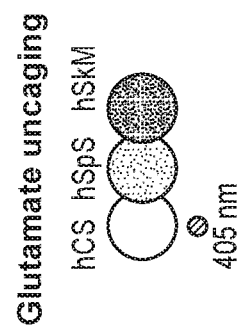
FIG. 7D
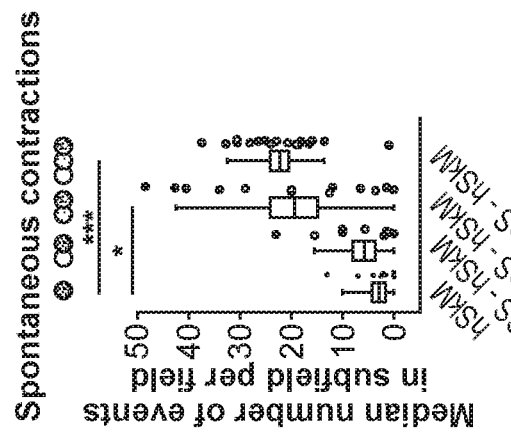
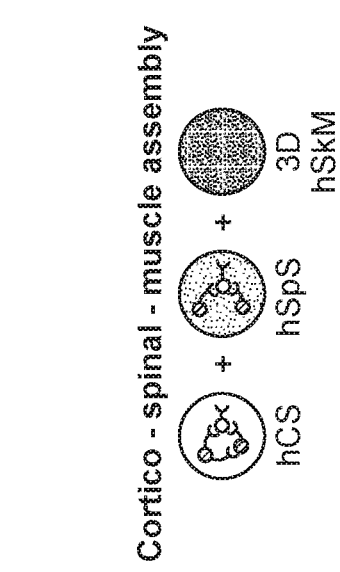
FIG. 7A
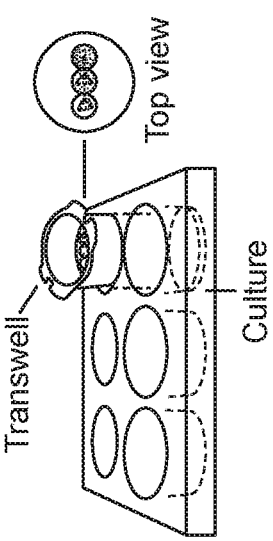
FIG. 7B

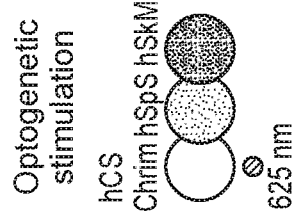
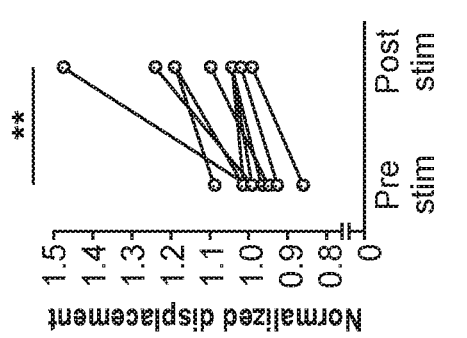
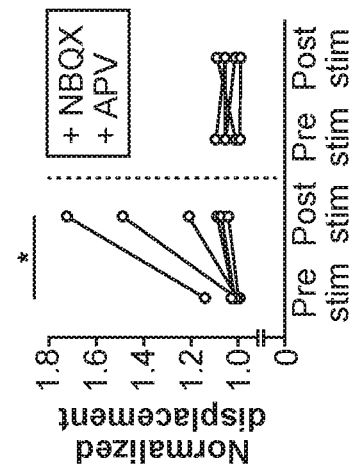
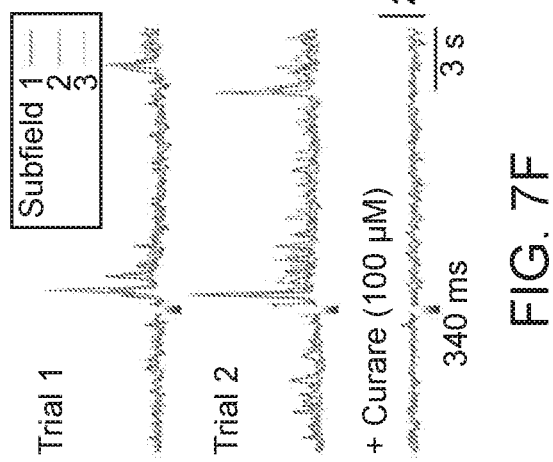
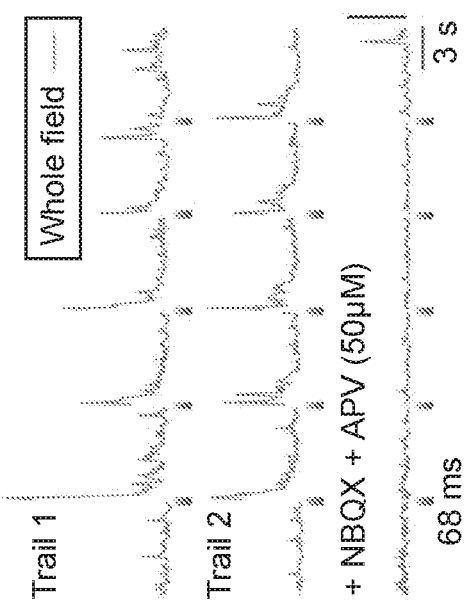
FIG. 7F
FIG. 7G
FIG. 7H
FIG. 7I
FIG. 7J

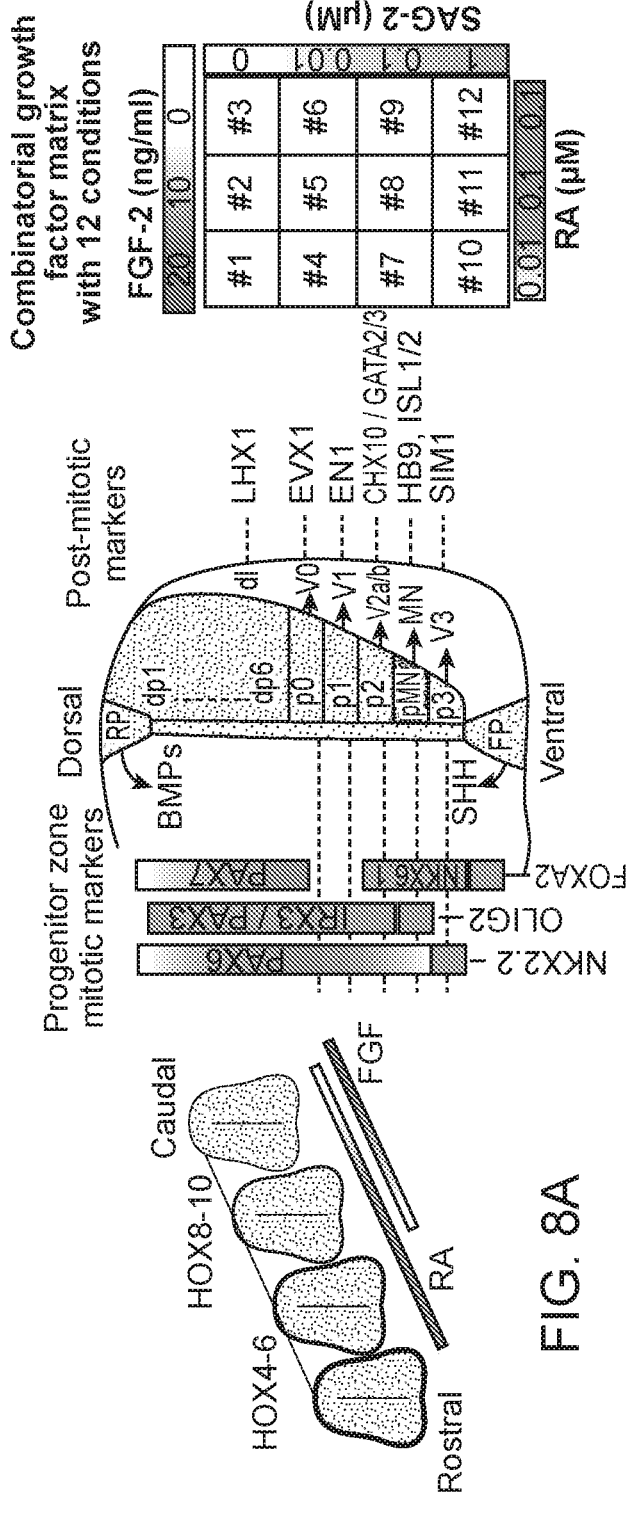
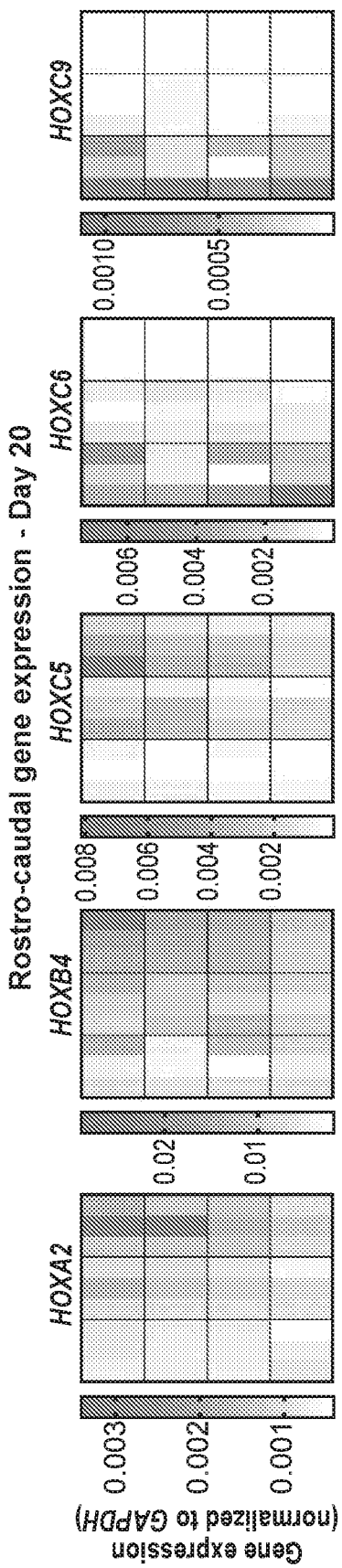
FIG. 8A
FIG. 8B
FIG. 8C
FIG. 8D

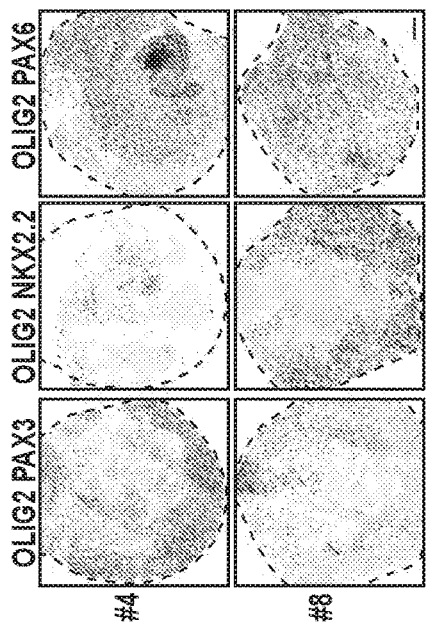
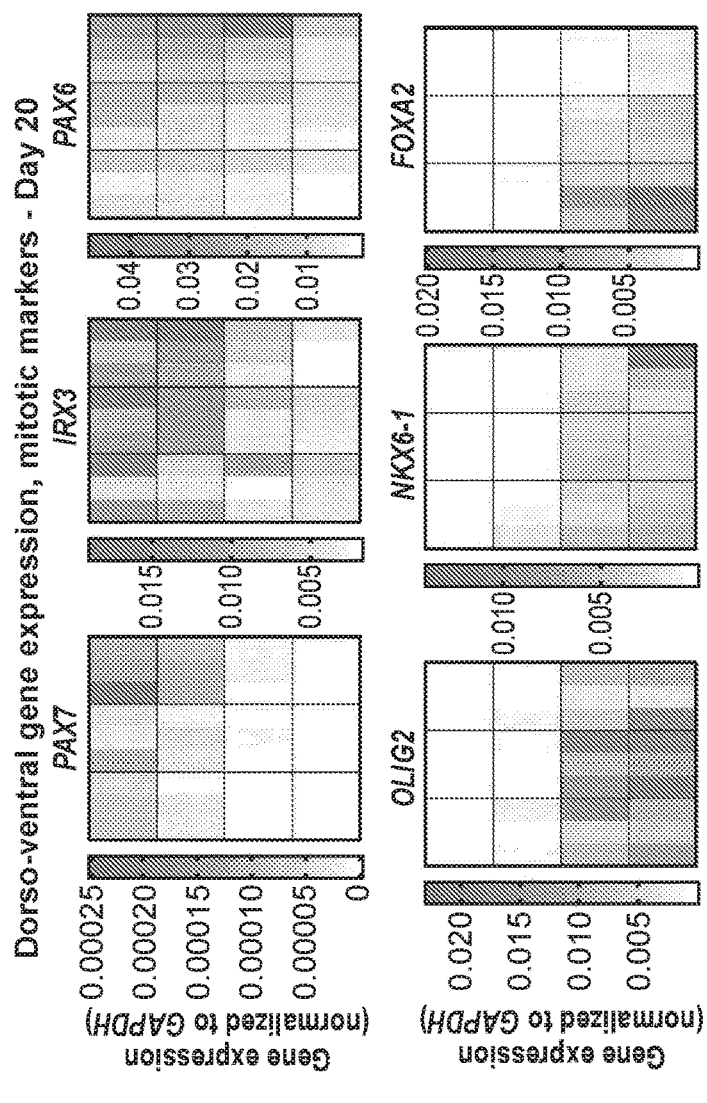
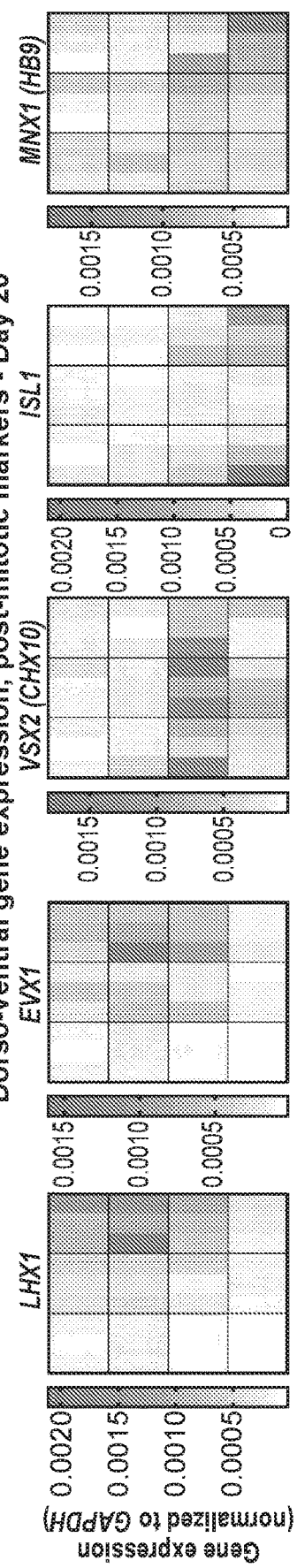
FIG. 8E
FIG. 8F
FIG. 8G

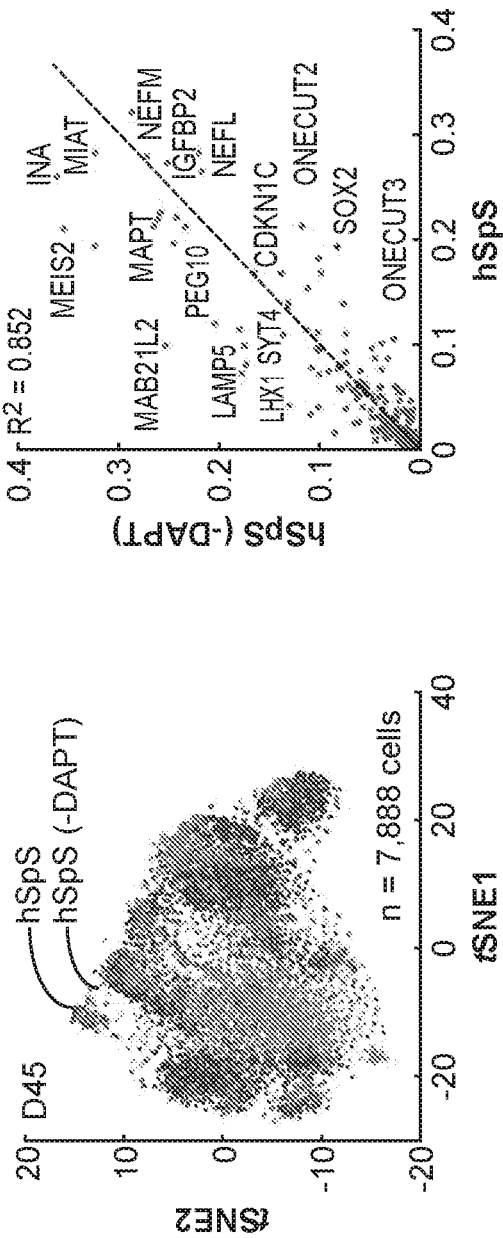
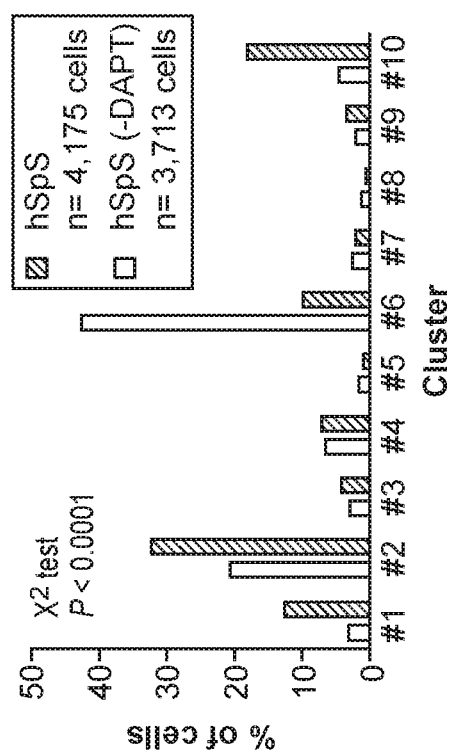
FIG. 9D
FIG. 9E
FIG. 9F

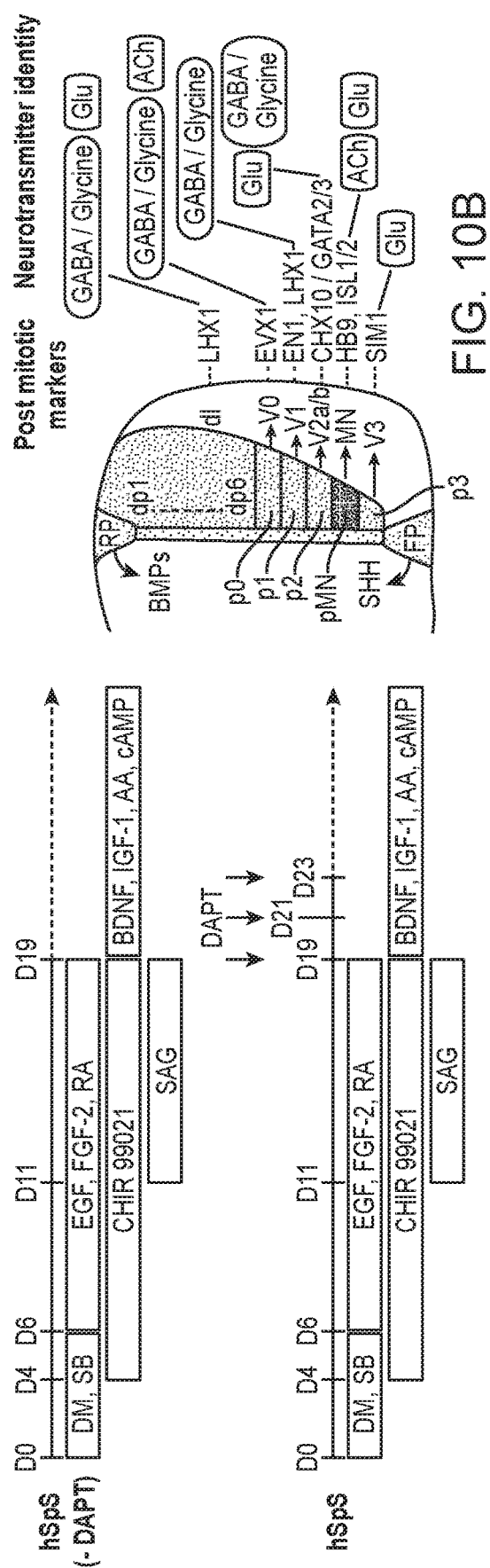
FIG. 10A
FIG. 10B
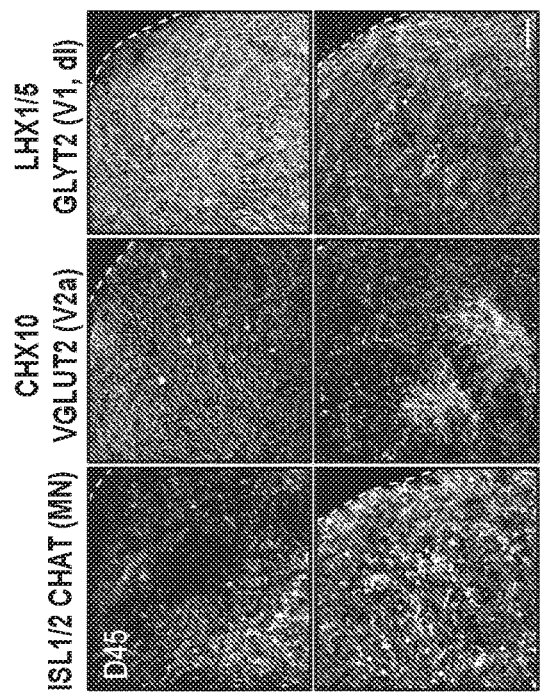
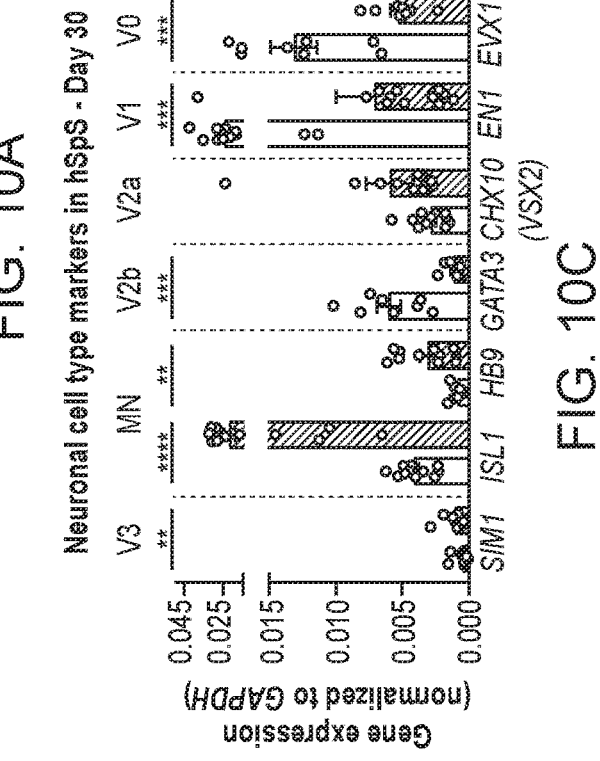
FIG. 10C
FIG. 10D

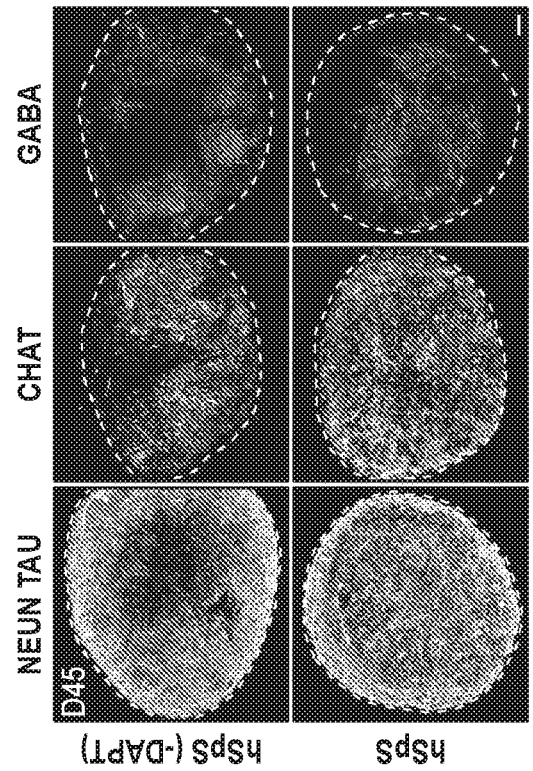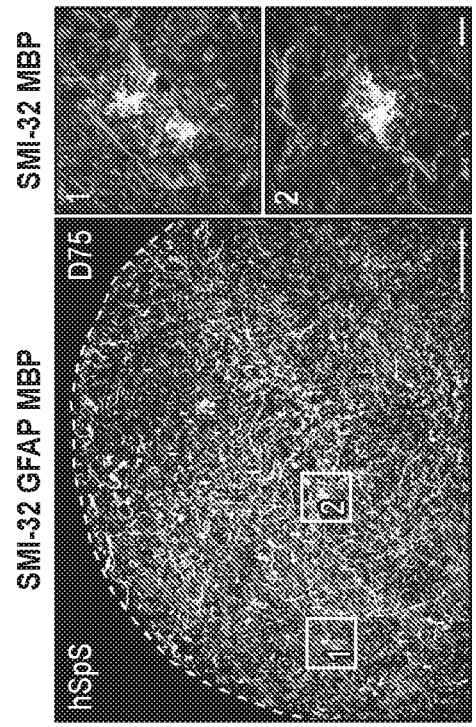
FIG. 10F
FIG. 10H
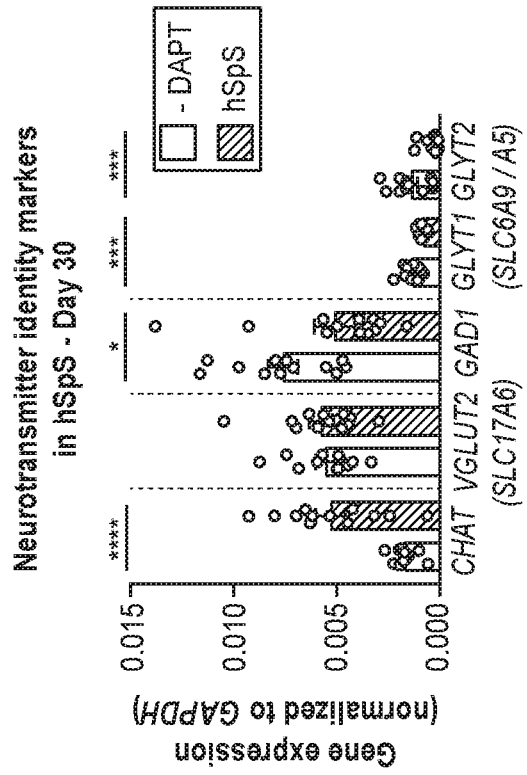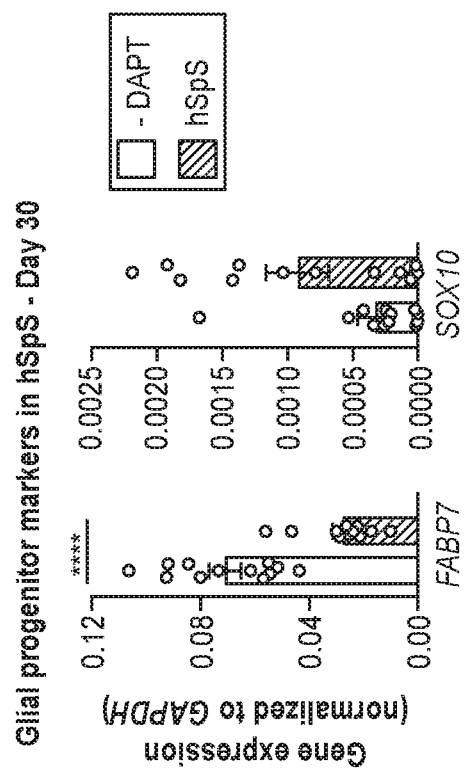
FIG. 10E
FIG. 10G

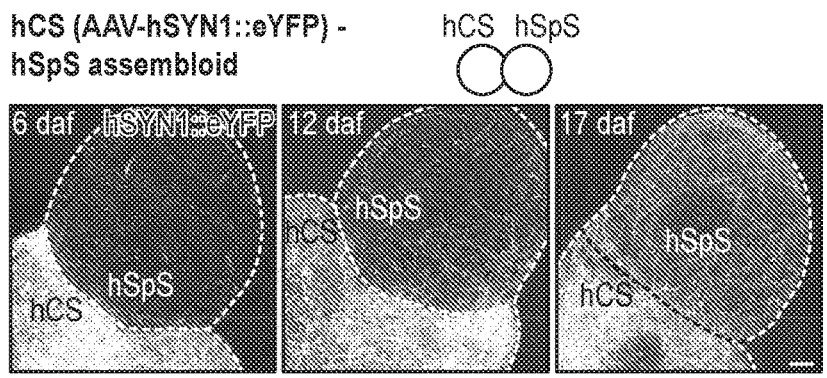
FIG. 12A
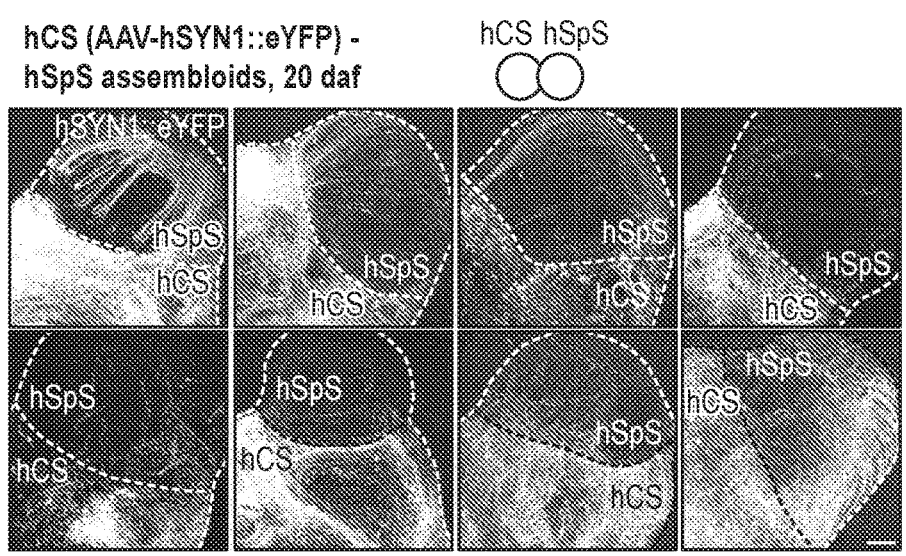
FIG. 12B
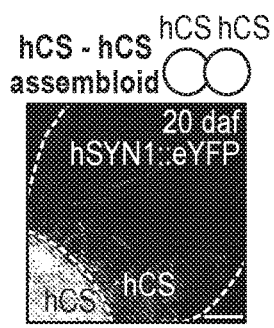
FIG. 12C
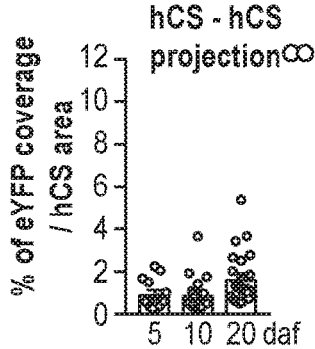
FIG. 12D
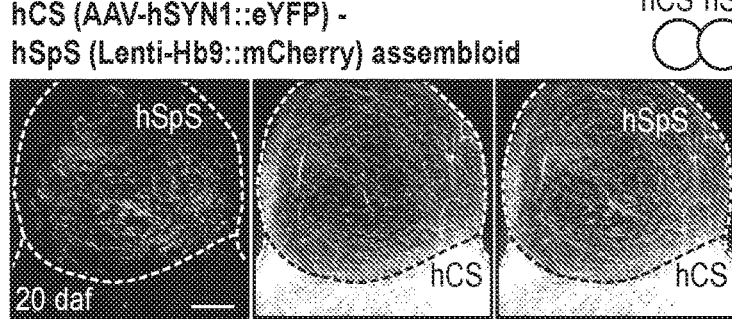
FIG. 12E
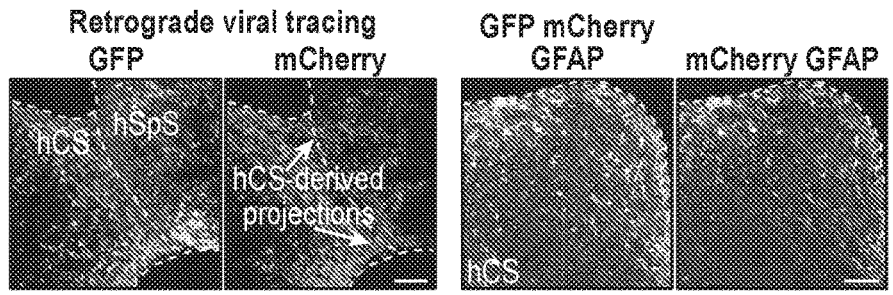
FIG. 12F
FIG. 12G

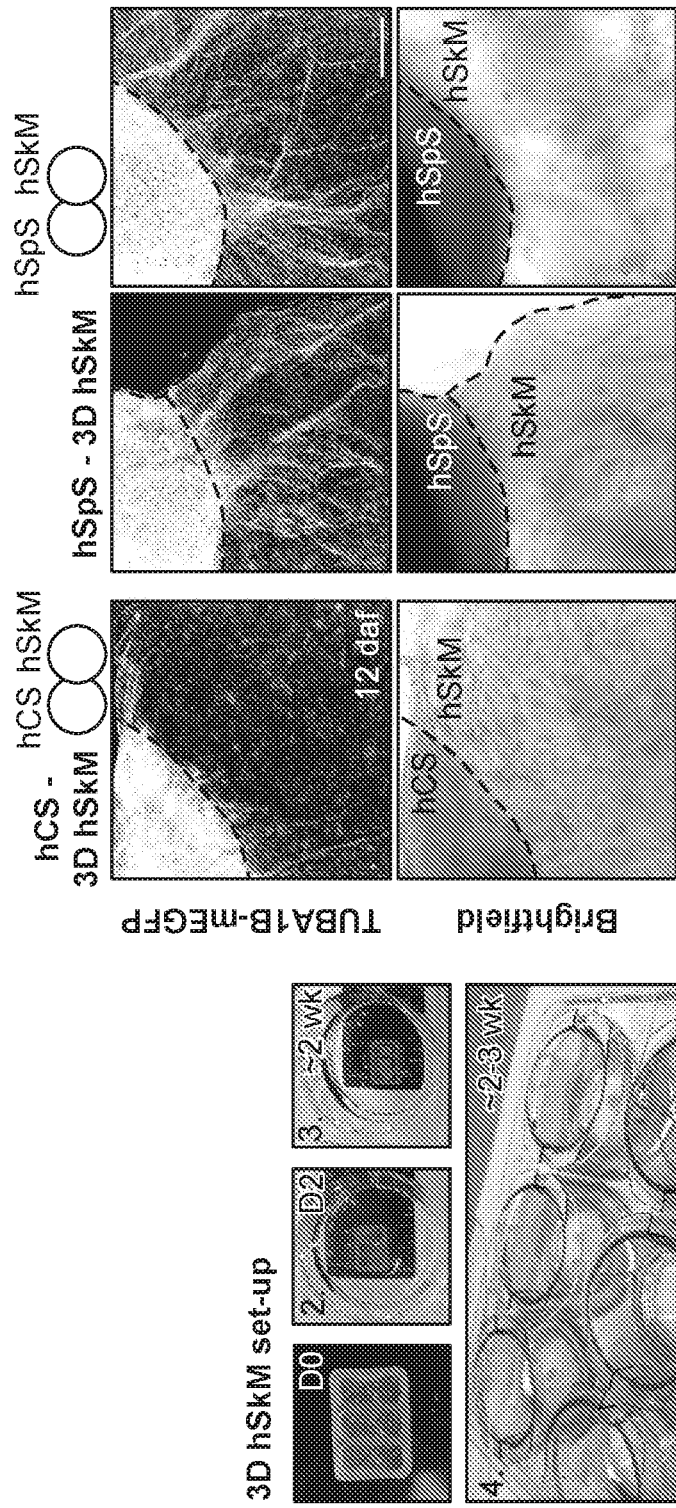
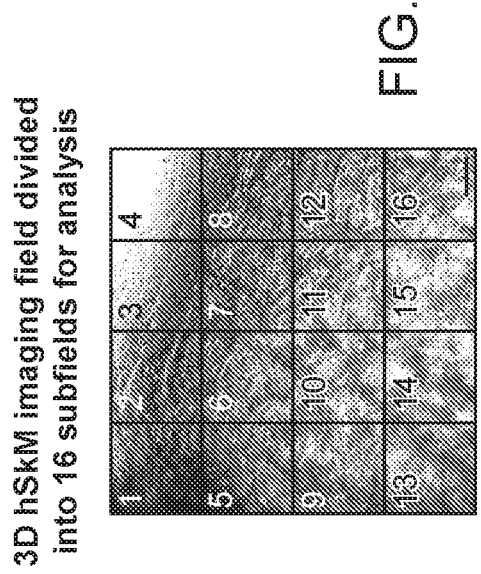
FIG. 14A
FIG. 14B
FIG. 14C

AAV-hSYN1-ChrimsonR-tdT

Optogenetic stimulation
success rate (out of 5 pulses)

Optogenetic stimulation

Optogenetic stimulation

FUNCTIONAL CORTICO-SPINAL-MUSCLE ASSEMBLED SPHEROIDS

CROSS REFERENCE

This application claims the benefit and is a 371 Applications of PCT Application No. PCT/US2019/038307, filed Jun. 20, 2019, which claims benefit of U.S. Provisional Application No. 62/688,924, filed Jun. 22, 2018 which are incorporated herein by reference in their entirety.

BACKGROUND OF THE INVENTION

The corticospinal tract plays a central role in controlling muscle activity by mediating voluntary movements. During development, corticospinal neurons in the motor cortex of the central nervous system extend long axonal projections that innervate the spinal cord. In turn, motor neurons in the spinal cord innervate proximal skeletal muscle to form neuromuscular junctions and give rise to a motor unit. This circuit, as a whole, allows for the cerebral cortex to control and coordinate body and limb movement. Damage or degeneration to any of the components of this circuit following spinal cord injury, amyotrophic lateral sclerosis (ALS) or autoimmune disorders such as multiple sclerosis (MS) leads to severe motor dysfunction. Results from animal models of these disorders have not been successfully translated to humans, and currently, there are no efficient treatments for these disorders.

There is great need for human models that can functionally integrate components of the corticospinal tract circuit, allowing screening for therapies that translate into treatments for patients.

Publications Birey et al. Nature 545: 54-59, 2017. Pasca et al. Functional cortical neurons and astrocytes from human pluripotent stem cells in 3D cultures. Nature Methods, 12: 671-78, 2015.

SUMMARY OF THE INVENTION

Compositions and methods are provided for in vitro generation of functional human cortico-spinal-muscle assembled spheroids, which may be generated at least in part from human pluripotent stem cells (hPSCs). Complete cortico-spinal-muscle spheroids (hCS-hSC-hSkM) are assembled from component cultured cell systems, where each cultured cell system is designed to provide specific sets of neural and/or muscle cells, and which components are functionally integrated in the assembled spheroid. Functionally integrated cells interact in a physiologically relevant manner, e.g. forming synapses or neuromuscular junctions, transmitting signals, inducing muscle contractions, forming multicellular structures, and the like.

The component systems of cortico-spinal-muscle spheroids include without limitation human ventral spinal cord spheroids (hSC) and human skeletal muscle cells (hSkM), which may be integrated into a spinal cord muscle assembled spheroid (hSC-hSkM); and human cortical spheroids (hCS). The assembled spheroids, i.e. hSC; hSC-hSkM; and hCS-hSC-hSkM provide unique opportunities for analysis and screening of agents that affect cortico-spinal-muscular circuits; including, without limitation, CNS injury, genetic mutations, infectious agents, therapeutic agents, nutritional factors, electrophysiological factors, and the like. Derivation of the assembled spheroids from pluripotent stem cells allows the development of patient-specific and disease-specific models.

In some embodiments, one or more such functional assembled spheroids, i.e. hSC; hSC-hSkM; and hCS-hSC-hSkM are provided, including without limitation a panel of such in vitro derived assembled spheroids, i.e. hSC; hSC-hSkM; and hCS-hSC-hSkM are provided, where the panel includes spheroids generated from two or more genetically different cells. In some embodiments the genome of each of: the hCS component, the hSkM component, and the hSC component are the same or different. In some embodiments a panel of such functional assembled spheroids are subjected to a plurality of candidate agents, or a plurality of doses of a candidate agent. Candidate agents include small molecules, i.e. drugs, genetic constructs that increase or decrease expression of an RNA of interest, infectious agents, electrical changes, and the like. In some embodiments a panel refers to functional assembled spheroids, or a method utilizing patient-specific functional assembled spheroids, from two or more distinct conditions, e.g. different genetic backgrounds, exposure to different drug treatments, exposure to pathogens, etc., and may be three or more, four or more, five or more, six or more, seven or more different conditions.

In some embodiments, methods are provided for determining the activity of a candidate agent on human cells present in the functional assembled spheroids, i.e. hSC; hSC-hSkM; and hCS-hSC-hSkM, the method comprising contacting the candidate agent with one or a panel of functional assembled spheroids. The cells present in the functional assembled spheroids optionally comprise at least one allele encoding a mutation associated with, or potentially associated with, a cortical, spinal or neuromuscular disease; and determining the effect of the agent on morphological, genetic or functional parameters, including without limitation gene expression profiling, migration assays, muscle strength, fatigability, muscle contraction rate, relaxation rate, muscle fatigue/damage, and recovery from fatigue/damage, axonal growth and pathfinding assays, atomic force microscopy, super resolution microcopy, light-sheet microscopy, two-photon microscopy, patch clamping, cell death in neurodegenerative disorders, single cell gene expression (RNA-seq), calcium imaging with pharmacological screens, modulation of synaptogenesis and neuromuscular junctions, and the like.

Optionally individual cell types of interest can be isolated from functional assembled spheroids, i.e. hSC; hSC-hSkM; and hCS-hSC-hSkM for various purposes. The cells are harvested at an appropriate stage of development, which may be determined based on the expression of markers and phenotypic characteristics of the desired cell type. Cultures may be empirically tested by immunostaining for the presence of the markers of interest, by morphological determination, etc. The cells are optionally enriched before or after the positive selection step by drug selection, panning, density gradient centrifugation, flow cytometry etc. In another embodiment, a negative selection is performed, where the selection is based on expression of one or more of markers found on hESCs or hiPSC, fibroblasts, epithelial cells, and the like. Selection may utilize panning methods, magnetic particle selection, particle sorter selection, fluorescent activated cell sorting (FACS) and the like.

Ventral spinal cord spheroids (hSC) comprise functional human cholinergic motor neurons; and other excitatory and inhibitory interneurons. The relative proportion of these types of neurons can be shifted by modulating the Notch pathway. These functional motor neurons have the ability to promote muscle contractions in skeletal muscle cells. The hSC and cells derived therefrom may be used for transplantation, for experimental evaluation, as a source of lineage and cell specific products, and the like. In one embodiment, methods are provided for generating human ventral spinal cord spheroids and cells comprised therein, including, for example motor neurons and interneurons. The methods instruct pluripotent stem cells to develop a neural fate in vitro, and are then specified into a ventral spinal cord fate.

Human skeletal muscle cells can be functionally integrated with hSC to generate hSC-hSkM spheroids through co-culture, where neuromuscular junctions are formed between the motor neurons and the muscle cells. The skeletal muscle cells can be cultured from various sources, e.g. differentiated from hPSCs, isolated from primary skeletal myoblasts, etc. In some embodiments the hSkM are cultured in a 3-dimensional (3-D) matrix, e.g. a gel matrix, which may be referred to as 3-D. In other embodiments the hSkM are cultured on a flat plate, referred to as a 2-D culture.

The hSC, or hSC-hSkM can be functionally integrated with human cerebral cortical spheroids (hCSs), which include pyramidal glutamatergic neurons of all cortical layers. The resulting assembled spheroid forms corticospinal projections and provides for functional integration of muscles, motor neurons, interneurons and cortical neurons. Using a combination of viral tracing, calcium imaging and electrophysiological methods, evidence is provided herein for the formation of an in vitro generated human corticospinal-muscular circuit, which provides useful modeling of injury, disease, and therapy.

These and other objects, advantages, and features of the invention will become apparent to those persons skilled in the art upon reading the details of the subject methods and compositions as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1M. Characterization of hSC spheroids. FIG. 1A, Scheme showing the generation of hSC from hiPSC. FIG. 1B. Gene expression of key spinal cord transcription factor markers over time (all markers relative to GAPDH). FIG. 1C, Immunostaining of the progenitor marker OLIG2 in hSC neurons at day 20 of differentiation. FIG. 1D, Example of SMI-32 and CHAT immunostaining in a hSC motor neuron at day 30 of differentiation. FIG. 1E, Gene expression analysis of neuronal subtypes in hSC or hSC+D. Markers shown represent different spinal cord domains (i.e. V3, MN, V2c, V2b, V2a, V1, V0) at day 30 of differentiation. FIG. 1F, Example immunostaining of NEUN, GAD67 and CHAT highlighting different neuronal subtypes in a hSC at day 45 of differentiation. FIG. 1G, Immunostaining showing axons (TAU) positioned on the outside and cell bodies (NEUN) positioned on the inside of a hSC+D at day 45 of differentiation.

FIG. 1H, 3D reconstruction using iDISCO showing motor neurons (SMI-32) and astrocytes (GFAP) in a hSC+D at day 60 of differentiation. FIG. 1I, Immunostaining showing neurons (SMI-32), astrocytes (GFAP) and oligodendrocytes (MBP) together in a hSC+D at day 75 of differentiation. FIG. 1J, Co-culture of hSkM in 2D and a hSC derived from a GFP-tagged TUBA1B hiPSC line showing projections from the hSC to hSkM. FIG. 1K, Calcium imaging in hSkM co-cultured with hSC. Traces are from hSkM fiber delineated in FIG. 1J. FIG. 1L, Immunostaining showing neuromuscular junction (BTX puncta) in Desmin-positive multinucleated hSkM fibers that were co-cultured with hSC. FIG. 1M, hSC derived from GFP-tagged TUBA1B hiPSC line that has been assembled with a 3-D hSkM spheroid for 10 days.

FIG. 2A-2F. Assembly of hCS and hSC to form assembled corticospinal spheroids (hCS-hSC). FIG. 2A, Schematic showing assembly. FIG. 2B, SYN-1 YFP-labeled hCS-derived neurons projecting into hSC 6, 12 and 17 days after assembly. FIG. 2C, Quantification of the projections over time represented as a percentage of pixels that are SYN-1 positive over the total hSC area. FIG. 2D, Schematic illustrating viral tracing assay. Before assembly hCS is labeled with AAV-DIO-mCherry and hSC is labeled with AG Rabies-eGFP+Cre+AAV-G. FIG. 2E, Representative immunostaining of corticospinal viral tracing. hSC cells are labeled with GFP, and hCS neurons that project to hCS will be labeled with GFP and mCherry once AG Rabies-eGFP is retrogradely transported and Cre-recombination takes place. FIG. 2F, Immunostaining showing $CTIP2^+$ corticospinal projecting neurons in hCS.

FIG. 3A-3K. Assembly of cortico-spinal-muscle spheroids. FIG. 3A, Schematic showing assembly of hCS-hSC and hSkM in 3D. FIG. 3B, Cortico-spinal-muscle assembled spheroids. hCS is labeled with SYN-YFP. hSkM are embedded in a gel matrix. FIG. 3C, Quantification showing the number of spontaneous contractions over a two minute period in hSC-hSkM or hCS-hSC-hSkM. FIG. 3D, 3E, Examples of spontaneous contractions in fields of hSC-hSkM or hCS-hSC-hSkM, respectively. Quantification was done using the MUSCLEMOTION macro for ImageJ that is based on pixel deviation for movement quantification. FIG. 3F, Schematic showing hCS-hSC-hSkM assembloid glutamate uncaging on hSC. FIG. 3G, Contractions over time before and after uncaging of glutamate on hSC. Red stars show the uncaging events. FIG. 3H, Contractions over time before and after uncaging of glutamate on hSC in the presence of the acetylcholine receptor blocker tubocurarine. Red stars show the uncaging events. FIG. 3I, Schematic showing hCS-hSC-hSkM assembloid glutamate uncaging on hCS.

FIG. 3J, 3K, Contractions over time before and after uncaging of glutamate on hCS. Red stars show the uncaging events.

FIG. 5. Characterization of cortico-spinal projections using a retrograde viral tracing approach a, Scheme detailing retrograde viral tracing experiment. hCS and hSpS are separately infected before assembly. b, Immunocytochemistry of hCS-hSpS assembloid 31 days after fusion (daf) showing expression of GFP in hSpS and co-expression of GFP and mCherry on the hCS side. c, Immunocytochemistry of hCS-hSpS assembloid at 31 daf showing expression of mCherry and the neuronal marker MAP2. d, Quantification of the percentage (%) of GFP positive and mCherry positive cells on the hCS side of hCS-hSpS assembloids that co-express the neuronal marker MAP2 or the glial marker GFAP (n=10 assembloids from 3 hiPS cell lines, with 2-3 cryosections quantified per assembloid). 10 e, f, Representative immunocytochemistry image for the cortico-fugal marker CTIP2 (e) or the callosal marker BRN2 (f) on the hCS side of hCS-hSpS assembloids at 31 daf. g, Quantification of the percentage (%) of GFP positive and mCherry positive cells on the hCS side of hCS-hSpS assembloids that co-express either CTIP2 or BRN2 (n=10 assembloids derived from 3 hiPS cell lines, with 2-3 cryosections quantified per assembloid). h, Quantification of the percentage (%) of CTIP2$_+$ or BRN2$_+$ among all Hoechst+cells in hCS at this stage (n=6 assembloids derived from 3 hiPS cell lines, with 2-3 cryosections quantified per assembloid). Data represent mean±s.e.m. Scale bars, 50 μm (b, c, e, f).

FIG. 7. Cortical activity modulates muscle function in hCS-hSpS-hSkM assembloids a, b, Schemes showing hCS-hSpS-hSkM assembloid set-up. hCS-hSpS-hSkM assembloids are generated by assembly of intact hCS, hSpS and 3D hSkM on 6-well transwells (or culture inserts). c, Representative image showing intact hCS-hSpS-hSkM assembloid. 11 d, Quantification of spontaneous contractions in assembloids over a 2-minute period showing the median number of events in subfields per field (n=10 fields from 5 assembloids for hSkM, n=12 fields from 6 assembloids for hCS-hSkM, n=14 fields from 7 assembloids for hSpS-hSkM, n=19 fields from 11 assembloids for hCS-hSpS-hSkM; Kruskal-Wallis test P<0.0001, with Dunn's multiple comparison test: *P=0.01 for hSpS-hSkM versus hSkM, *P=0.0002 for hCS-hSpS-hSkM versus hSkM). Box plot shows mean±s.e.m. and whiskers show 90th and 10th percentiles. e, f, Glutamate uncaging in hCS-hSpS-hSkM assembloid. UV light (405 nm) uncages glutamate on hCS (e). Two trials with the same stimulation site are shown. Muscle contraction upon cortical stimulation stops after addition of curare (100 μM). Displacement normalized to baseline over time is shown for 3 subfields for each trial (f). g, Quantification of displacement normalized to baseline in different glutamate uncaging experiments. Values of the last frame before stimulation (Pre stim) and the highest of the first 3 frames after stimulation (Post stim) are plotted per field (subfields per field are averaged; n=10 fields from 7 assembloids derived from 3 hiPS cell lines; Wilcoxon test P=0.002). h, i, Optogenetic stimulation in hCS-hSpS-hSkM assembloids. hCS were infected with AAVhSYN1—ChrimsonR-tdT (Chrim) before assembly. Five pulses of light (625 nm, 68 ms in duration each and 68 seconds apart) were delivered using a fiber-coupled LED directed towards the hCS (h). Traces of whole-field muscle displacement are shown after normalization to the pre-stimulation baseline. Light-induced muscle displacement is abolished following exposure to NBQX (50 μM) and APV (50 μM) (i). j, Quantification of displacement (normalized to pre-stimulation baseline) per assembloid in the presence or absence of NBQX and APV (50 μM). Pre stim represents the highest value of displacement in the 20 frames (1.36 seconds) before stimulation. Post stim represents the average across 5 pulses of the highest value in the 20 frames immediately following stimulation (left: n=7 assembloids derived from 3 hiPS cell lines; Wilcoxon matched pairs test *P=0.01; right: n=6 assembloids derived from 3 hiPS cell lines; two-tailed paired ttest *P=0.94).

FIG. 8. Combinatorial analysis of developmental cues to determine hSpS culture conditions a, b, Schemes illustrating marker gene expression along the rostro-caudal (a) and dorsoventral (b) axes of the spinal cord. c, Scheme detailing the 12 conditions in the combinatorial growth factor matrix and the molecules and concentrations they receive. d, e, g, Gene expression analysis of genes expressed along the rostro-caudal (d) and dorsoventral (e, g) axes in the 12 conditions of the combinatorial matrix at day 20 of in vitro differentiation. Each condition shows 3 colored bars representative of n=3 hiPS cell lines (Kruskal-Wallis test P=0.002 for HOXA2, P=0.008 for HOXB4, P=0.003 for HOXC9, P=0.002 for HOXC9, P=0.0008 for PAX7, P=0.02 for PAX6, P=0.001 for OLIG2, P=0.002 for NKX6-1, P=0.0006 for LHX1, P=0.007 for CHX10, P=0.06 for HB9; one-way ANOVA P=0.002 for HOXC5, P=0.001 for IRX3, P<0.0001 for FOXA2, P<0.0001 for EVX1, P=0.01 for ISL1). f, Immunocytochemistry in cryosections of hSpS conditions #4 and #8 showing dorsal-like and ventral-like identities. Scale bar, 100 μm (f).

FIG. 10. Characterization of hSpS differentiation a, Scheme detailing differentiation conditions used for deriving hSpS with or without DAPT. b, Scheme illustrating spinal cord neuronal domains, their corresponding marker genes and their neurotransmitter identities. c, Gene expression analysis of neuronal cell type markers in hSpS at day 30 of in vitro differentiation (n=5 hiPS cell lines; two-tailed t-test: **P<0.0001 for ISL1, P=0.001 for 13 HB9, *P=0.0001 for GATA3, *P=0.0008 for EVX1; Mann-Whitney test: P=0.003 for SIM1, P=0.02 for CHX10, *P=0.0001 for EN1). d, Immunocytochemistry in hSpS cryo-sections at day 45 of in vitro differentiation showing expression of different neuronal domain marker genes. e, Gene expression analysis of neuronal cell type markers in hSpS at day 30 of in vitro differentiation (n=5 hiPS cell lines; two-tailed t-test: **P<0.0001 for CHAT, *P=0.0009 for GLYT1; Mann-Whitney test: P=0.9 for VGLUT2, *P=0.01 for GAD1, *P=0.0009 for GLYT2). f, Immunocytochemistry in hSpS cryo-sections at day 45 of in vitro differentiation showing expression of different neuronal and neurotransmitter identity markers. g, Gene expression analysis of glial progenitor markers in hSpS at day 30 of in vitro differentiation (n=5 hiPS cell lines; Mann-Whitney test, **P<0.0001 for FABP7, P=0.1 for SOX10). h, Immunocytochemistry in hSpS cryosections at day 75 of in vitro differentiation showing expression of the astrocyte marker GFAP and the oligodendrocyte marker MBP. Data represent mean±s.e.m. Scale bars, 10 μm (insets in h), 50 μm (d), 100 μm (f, h).

FIG. 12. Neuronal projections in cortico-spinal (hCS-hSpS) assembloids a, Representative images of intact hCS-hSpS assembloid showing hCS-derived hSYN1::eYFP projections 6, 12 and 17 days after fusion (daf). b, Images of intact hCS-hSpS assembloids 20 days after fusion (daf) showing hCS-derived hSYN1::eYFP projections. c, d, Representative image of intact hCS-hCS assembloid (c) and quantification of the extent of projection of hSYN1::eYFP (d) (n=3 hiPS cell lines; Kruskal-Wallis test interaction P=0.01, with Dunn's multiple comparison test: P>0.9 for 10 versus 5 daf, P=0.06 for 20 versus 5 daf). See FIG. 4m for quantification of the projection in hCS-hSpS assembloids. 14 e, Representative image of intact hCS-hSpS assembloid where hCS was infected with AAVhSYN1::eYFP and hSpS with lenti-Hb9::mCherry. No hSpS-derived Hb9::mCherry projections are observed in hCS (similar results were observed in 15 assembloids from 2 differentiations and 3 hiPS cell lines). f, Representative immunocytochemistry image of hCS-hSpS assembloid in retrograde viral tracing experiment at 31 daf showing GFP expression in hSpS and colocalization of GFP and mCherry in hCS. mCherry projections from hCS to hSpS can also be seen. g, Representative immunocytochemistry image of GFP, mCherry and the glial marker GFAP on the hCS side of hCS-hSpS assembloid at 31 daf. Scale bars, 100 μm (a, f, g), 200 μm (b, c, e).

DETAILED DESCRIPTION OF THE INVENTION

Figure 1F:
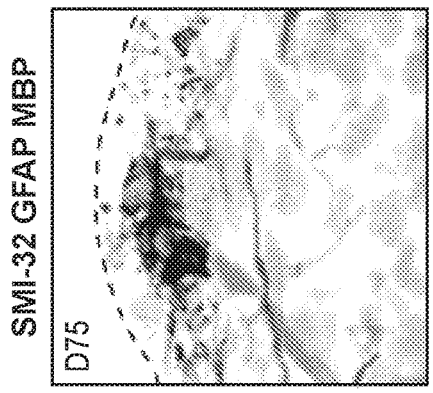

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "pluripotency" and pluripotent stem cells it is meant that such cells have the ability to differentiate into all types of cells in an organism. The term "induced pluripotent stem cell" encompasses pluripotent cells, that, like embryonic stem cells (hESC), can be cultured over a long period of time while maintaining the ability to differentiate into all types of cells in an organism. hiPSC have a human hESC-like morphology, growing as flat colonies containing cells with large nucleo-cytoplasmic ratios, defined borders and prominent nuclei. In addition, hiPSC express pluripotency markers known by one of ordinary skill in the art, including but not limited to alkaline phosphatase, SSEA3, SSEA4, SOX2, OCT3/4, NANOG, TRA-1-60, TRA-1-81, etc. In addition, the hiPSC are capable of forming teratomas and are capable of forming or contributing to ectoderm, mesoderm, or endoderm tissues in a living organism.

Pluripotent stem cells may be obtained from patient or carrier cell samples, e.g. adipocytes, fibroblasts, keratinocytes, blood cells and the like. Various somatic cells find use as a source of hiPSCs; of particular interest are adipose-derived stem cells, fibroblasts, and the like. The use of hiPSCs from individuals of varying genotypes, particularly genotypes potentially associated with neurologic and neuromuscular disorders are of particular interest.

As used herein, "reprogramming factors" refers to one or more, i.e. a cocktail, of biologically active factors that act on a cell, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, OCT3/4; SOX2; KLF4; c-MYC; NANOG; and LIN-28.

Somatic cells are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector. The somatic cells may be fibroblasts, adipocytes, stromal cells, and the like, as known in the art. Somatic cells or hiPSC can be obtained from cell banks, from normal donors, from individuals having a neurologic or psychiatric disease of interest, etc.

Following induction of pluripotency, hiPSC are cultured according to any convenient method, e.g. on irradiated feeder cells and commercially available medium. The hiPSC can be dissociated from feeders by digesting with protease, e.g. dispase, preferably at a concentration and for a period of time sufficient to detach intact colonies of pluripotent stem cells from the layer of feeders. The spheroids can also be generated from hiPSC grown in feeder-free conditions, by dissociation into a single cell suspension and aggregation using various approaches, including centrifugation in plates, etc.

Genes may be introduced into the somatic cells or the hiPSC derived therefrom for a variety of purposes, e.g. to replace genes having a loss of function mutation, provide marker genes, etc. Alternatively, vectors are introduced that express antisense mRNA, siRNA, ribozymes, etc. thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as BCL-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

Disease-associated or disease-causing genotypes can be generated in healthy hiPSC through targeted genetic manipulation (CRISPR/CAS9, etc) or hiPSC can be derived from individual patients that carry a disease-related genotype or are diagnosed with a disease. Moreover, neural and neuromuscular diseases with less defined or without genetic components can be studied within the model system. A particular advantage of this method is the fact that edited hiPSC lines share the same genetic background as their corresponding, non-edited hiPSC lines. This reduces variability associated with line-line differences in genetic background. Conditions of neurodevelopmental and neuropsychiatric disorders and neural diseases that have strong genetic components or are directly caused by genetic or genomic alterations can be modeled with the systems of the invention.

Disease relevance. The effect of genetics, drugs, injury and pathogens on neurons, including motor neurons, cortical neurons and neuromuscular junctions is of particular interest, where efficacy and toxicity may rest in sophisticated analysis of neuronal projection, migratory and electrical interactions with neurons and non-neuronal cells, or the ability of neurons to form functional networks with muscles, rather than on simple viability assays. The discrepancy between the number of lead compounds in clinical development and approved drugs may partially be a result of the methods used to generate the leads and highlights the need for new technology to obtain more detailed and physiologically relevant information on cellular processes in normal and diseased states.

As well as understanding development, this system is useful to model disorders of the cortico-spinal/motor unit. Some of these include injuries of the spinal cord, neurodevelopmental and neurodegenerative disorders that affect the corticospinal tract like spinal muscular atrophy (SMA) and amyotrophic lateral sclerosis (ALS), or disorders with a neuroimmune component like myasthenia gravis, Lambert Eaton or multiple sclerosis (MS).

Motor neuron diseases. The systems of the present invention provide unique opportunities to study diseases of the spinal cord and motor neurons. Motor neuron diseases (MNDs) are classified according to whether they are inherited or sporadic, and to whether degeneration affects upper motor neurons, lower motor neurons, or both. In adults, the most common MND is amyotrophic lateral sclerosis (ALS), which affects both upper and lower motor neurons. It has inherited and sporadic forms and can affect the arms, legs, or facial muscles.

Amyotrophic lateral sclerosis (ALS) is a progressive, ultimately fatal disorder that disrupts signals to all voluntary muscles. Approximately 75 percent of people with classic ALS will develop weakness and wasting of the bulbar muscles (muscles that control speech, swallowing, and chewing). Muscle weakness and atrophy occur on both sides of the body. When muscles of the diaphragm and chest wall fail to function properly, individuals lose the ability to breathe without mechanical support. Most individuals with ALS die from respiratory failure, usually within 3 to 5 years from the onset of symptoms. Most cases of ALS occur sporadically, and family members of those individuals are not considered to be at increased risk for developing the disease. Familial forms of ALS account for 10 percent or less of cases of ALS, with more than 10 genes identified to date. The most common familial forms of ALS in adults are caused by mutations of the superoxide dismutase gene, or SOD1, located on chromosome 21. There are also rare juvenile-onset forms of familial ALS.

Progressive bulbar palsy, also called progressive bulbar atrophy, involves the brain stem. Symptoms include pharyngeal muscle weakness (involved with swallowing), weak jaw and facial muscles, progressive loss of speech, and tongue muscle atrophy.

Pseudobulbar palsy, which shares many symptoms of progressive bulbar palsy, is characterized by degeneration of upper motor neurons that transmit signals to the lower motor neurons in the brain stem. Affected individuals have progressive loss of the ability to speak, chew, and swallow.

Primary lateral sclerosis (PLS) affects the upper motor neurons of the arms, legs, and face. It occurs when specific nerve cells in the motor regions of the cerebral cortex gradually degenerate, causing the movements to be slow and effortful. PLS is sometimes considered a variant of ALS, but the major difference is the sparing of lower motor neurons, the slow rate of disease progression, and normal lifespan.

Progressive muscular atrophy is marked by slow but progressive degeneration of only the lower motor neurons. Weakness is typically seen first in the hands and then spreads into the lower body, where it can be severe. Other symptoms may include muscle wasting, clumsy hand movements, fasciculations, and muscle cramps. The disease develops into ALS in many instances.

Spinal muscular atrophy (SMA) is a hereditary disease affecting the lower motor neurons. It is an autosomal recessive disorder caused by defects in the gene SMN1, which protein is important for the survival of motor neurons. In SMA, insufficient levels of the SMN protein lead to degeneration of the lower motor neurons, producing weakness and wasting of the skeletal muscles. SMA in children is classified into three types, based on ages of onset, severity, and progression of symptoms. SMA type I, also called Werdnig-Hoffmann disease, is evident by the time a child is 6 months old. Symptoms may include hypotonia (severely reduced muscle tone), diminished limb movements, lack of tendon reflexes, fasciculations, tremors, swallowing and feeding difficulties, and impaired breathing. Symptoms of SMA type II, the intermediate form, usually begin between 6 and 18 months of age. Symptoms of SMA type III (Kugelberg-Welander disease) appear between 2 and 17 years of age and include abnormal gait; difficulty running, climbing steps, or rising from a chair; and a fine tremor of the fingers. The lower extremities are most often affected. Complications include scoliosis and joint contractures-chronic shortening of muscles or tendons around joints, caused by abnormal muscle tone and weakness, which prevents the joints from moving freely. Individuals with SMA type III may be prone to respiratory infections, but with care may have a normal lifespan.

Congenital SMA with arthrogryposis is a rare disorder. Manifestations include severe contractures, scoliosis, chest deformity, respiratory problems, unusually small jaws, and drooping of the upper eyelids.

Kennedy's disease, also known as progressive spinobulbar muscular atrophy, is an X-linked recessive disease caused by mutations in the gene for the androgen receptor. Daughters of individuals with Kennedy's disease are carriers and have a 50 percent chance of having a son affected with the disease. The onset of symptoms is variable and the disease may first be recognized between 15 and 60 years of age. Symptoms include weakness and atrophy of the facial, jaw, and tongue muscles, leading to problems with chewing, swallowing, and changes in speech. Individuals with Kennedy's disease also develop sensory loss in the feet and hands.

Post-polio syndrome (PPS) is a condition that can strike polio survivors decades after their recovery from poliomyelitis. Polio is an acute viral disease that destroys motor neurons. Many people who are affected early in life recover and develop new symptoms many decades later. Symptoms include fatigue, slowly progressive muscle weakness, muscle atrophy, fasciculations, cold intolerance, and muscle and joint pain.

Cells and Structures

Spinal cord. The spinal cord extends caudally from the medulla at the foramen magnum and terminates at the upper lumbar vertebrae, usually between L1 and L2, where it forms the *conus medullaris*. In the lumbosacral region, nerve roots from lower cord segments descend within the spinal column in a nearly vertical sheaf, forming the *cauda equina*.

The white matter at the cord's periphery contains ascending and descending tracts of myelinated sensory and motor nerve fibers. The central H-shaped gray matter is composed of cell bodies and nonmyelinated fibers. The anterior (ventral) horns of the "H" contain lower motor neurons, which receive impulses from the motor cortex via the descending corticospinal tracts and, at the local level, from internuncial neurons and afferent fibers from muscle spindles. The axons of the lower motor neurons are the efferent fibers of the spinal nerves. The posterior (dorsal) horns contain sensory fibers that originate in cell bodies in the dorsal root ganglia. The gray matter also contains many internuncial neurons that carry motor, sensory, or reflex impulses from dorsal to ventral nerve roots, from one side of the cord to the other, or from one level of the cord to another.

Spinal cord disorders cause various patterns of deficits depending on which nerve tracts within the cord or which spinal roots outside the cord are damaged. Disorders affecting spinal nerves, but not directly affecting the cord, cause sensory or motor abnormalities or both only in the areas supplied by the affected spinal nerves. Corticospinal tract lesions cause upper motor neuron dysfunction. Acute, severe lesions (e.g., infarction, traumatic lesions) cause spinal shock with flaccid paresis (decreased muscle tone, hyporeflexia, and no extensor plantar responses). After days or weeks, upper motor neuron dysfunction evolves into spastic paresis (increased muscle tone, hyperreflexia, and clonus). Extensor plantar responses and autonomic dysfunction are present. Flaccid paresis that lasts more than a few weeks suggests lower motor neuron dysfunction (e.g., due to Guillain-Barré syndrome).

A motor neuron is a neuron whose cell body is located in the motor cortex, brainstem or the spinal cord, and whose axon projects to the spinal cord or outside of the spinal cord to directly or indirectly control effector organs, mainly muscles. Axons from upper motor neurons synapse onto interneurons in the spinal cord and occasionally directly onto lower motor neurons. The axons from the lower motor neurons are efferent nerve fibers that carry signals from the spinal cord to the effectors.

Skeletal muscle is a tissue composed of muscle cells (often multinucleated) that contain neatly packed actin and myosin filaments; these filaments are arranged in cylindrical bundles called myofibrils. In each cell, the myofibrils are all aligned in the same direction and are parceled into longitudinal blocks (called sarcomeres) of similar lengths. Skeletal muscle is innervated by somatic motor axons at a synaptic structure sometimes referred to as a motor endplate, where acetylcholine is the neurotransmitter. Most skeletal muscles can be controlled consciously.

The adult cerebral cortex contains two main classes of neurons: glutamatergic cortical neurons (also known as pyramidal cells) and GABAergic interneurons. Pyramidal cells are generated in the pallium—the roof of the telencephalon (dorsal forebrain)—and reach their final position by radial migration. In contrast, cortical interneurons are born in the subpallium—the base of telencephalon (ventral forebrain)—and reach the cerebral cortex through a long tangential migration.

The layers of the cerebral cortex are generated in an "inside-out" sequence, with deep layers being generated first and superficial layer neurons being generated last. In parallel to this process, GABAergic interneurons migrate to the cortical plate, where they disperse tangentially via highly stereotyped routes in the marginal zone (MZ), subplate (SP), and lower intermediate zone/subventricular zone (IZ/SVZ). Interneurons then switch from tangential to radial migration to adopt their final laminar position in the cerebral cortex.

The movement of cortical interneurons is saltatory. First, the cell extends a leading process. Second, the nucleus translocates towards the leading process, a step referred to as nucleokinesis and leads to the net movement of the cell.

The translocation of the nucleus into the leading process is the mechanism that best defines this type of saltatory neuronal migration. First, a cytoplasmic swelling forms in the leading process, immediately proximal to the nucleus. The centrosome, which is normally positioned in front of the nucleus, moves into this swelling. The centrosome is accompanied by additional organelles, including the Golgi apparatus, mitochondria, and the rough endoplasmic reticulum. Second, the nucleus follows the centrosome. These two steps are repeated producing the typical saltatory movement of migrating neurons.

Tangentially migrating neurons do not always follow radial glial fibers. In general, tangentially migrating cells can move in clusters or individually. Cellular interactions also differ depending on the nature of the substrate. They can be homotypic, when interactions occur between cells of the same class, or heterotypic, when migrating cells rely on the contact with other cell types for their migration or their substrates. In the most common scenario, neurons respond to cues present in the extracellular matrix or in the surface of other cells to achieve directional migration.

GABAergic interneurons are inhibitory neurons of the nervous system that play a vital role in neural circuitry and activity. They are so named due to their release of the neurotransmitter gamma-aminobutyric acid (GABA). An interneuron is a specialized type of neuron whose primary role is to modulate the activity of other neurons in a neural network.

There are interneuron subtypes categorized based on the surface markers they express, including parvalbumin (PV)-expressing interneurons, somatostatin (SST)-expressing interneurons, VIP-expressing, serotonin receptor 5HT3a (5HT3aR)-expressing interneurons, etc. Although these interneurons are localized in their respective layers of the cerebral cortex, they are generated in various subpallial locations.

Morphologically speaking, cortical interneurons may be described with regard to their soma, dendrites, axons, and the synaptic connections they make. Molecular features include transcription factors, neuropeptides, calcium-binding proteins, and receptors these interneurons express, among many others. Physiological characteristics include firing pattern, action potential measurements, passive or subthreshold parameters, and postsynaptic responses, to name a few.

The PV interneuron group represents approximately 40% of the GABAergic cortical interneuron population. This population of interneurons possesses a fast-spiking pattern, and fire sustained high-frequency trains of brief action potentials. Additionally, these interneurons possess the lowest input resistance and the fastest membrane time constant of all interneurons. Two types of PV-interneurons make up the PV interneuron group: basket cells, which make synapses at the soma and proximal dendrite of target neurons, and usually have multipolar morphology and chandelier cells, which target the axon initial segment of pyramidal neurons.

The SST-expressing interneuron group is the second-largest interneuron group. SST-positive interneurons are known as Martinotti cells, and possess ascending axons that arborize layer I and establish synapses onto the dendritic tufts of pyramidal neurons. Martinotti cells are found throughout cortical layers II-VI, but are most abundant in layer V. These interneurons function by exhibiting a regular adapting firing pattern but also may initially fire bursts of two or more spikes on slow depolarizing humps when depolarized from hyperpolarized potentials. In contrast to PV-positive interneurons, excitatory inputs onto Martinotti cells are strongly facilitating.

The third group of GABAergic cortical interneurons is designated as the 5HT3aR interneuron group. VIP-expressing interneurons are localized in cortical layers II and Ill. VIP interneurons generally make synapses onto dendrites, and some have been observed to target other interneurons. Relative to all cortical interneurons, VIP interneurons possess a very high input resistance. In general they possess a bipolar, bitufted and multipolar morphology. Irregular spiking interneurons possess a vertically oriented, descending axon that extends to deeper cortical layers, and have an irregular firing pattern that is characterized by action potentials occurring irregularly during depolarizations near threshold, and express the calcium-binding protein calretinin (CR). Other subtypes include rapid-adapting, fast-adapting neurons IS2, as well as a minor population of VIP-positive basket cells with regular, bursting, or irregular-spiking firing patterns. Of the VIP-negative 5HT3aR group, nearly 80% express the interneuron marker Reelin. Neurogliaform cells are a type of cortical interneuron that belongs to this category: they are also known as spiderweb cells and express neuropeptide Y (NPY), with multiple dendrites radiating from a round soma.

Glutamatergic neurons. The mature cerebral cortex harbors a heterogeneous population of glutamatergic neurons, organized into a highly intricate histological architecture. So-called excitatory neurons are usually classified according to the lamina where their soma is located, specific combinations of gene expression, by dendritic morphologies, electrophysiological properties, etc.

Based on the differences in connections, pyramidal neurons are classified as projection neurons with long axons that connect different cortical regions or project to subcortical targets. Cortical projection neurons can be further classified by hodology in associative, commissural and corticofugal subtypes. Associative projection neurons extend axons within a single hemisphere, whereas commissural projection neurons connect neurons in the two cortical hemispheres either through the corpus callosum or the anterior commissure. Corticofugal projection neurons send axons to target areas outside the cerebral cortex, such as the thalamus (corticothalamic neurons), pons (corticopontine neurons (CPN), spinal cord (costicospinal neurons), superior colliculus (corticotectal neurons) and striatum (corticostriatal neurons).

The terms "astrocytic cell," "astrocyte," etc. encompass cells of the astrocyte lineage, i.e. glial progenitor cells, astrocyte precursor cells, and mature astrocytes, which for the purposes of the present invention arise from a non-astrocytic cells (i.e., glial progenitors). Astrocytes can be identified by markers specific for cells of the astrocyte lineage, e.g. GFAP, ALDH1 L1, AQP4, EAAT1 and EAAT2, etc. Markers of reactive astrocytes include S100, VIM, LCN2, FGFR3 and the like. Astrocytes may have characteristics of functional astrocytes, that is, they may have the capacity of promoting synaptogenesis in primary neuronal cultures; of accumulating glycogen granules in processes; of phagocytosing synapses; and the like. A "astrocyte precursor" is defined as a cell that is capable of giving rise to progeny that include astrocytes.

Astrocytes are the most numerous and diverse neuroglial cells in the CNS. An archetypal morphological feature of astrocytes is their expression of intermediate filaments, which form the cytoskeleton. The main types of astroglial intermediate filament proteins are glial fibrillary acidic protein (GFAP) and vimentin; expression of GFAP, ALDH1 L1 and/or AQP4P are commonly used as a specific marker for the identification of astrocytes.

The terms "oligodendrocyte," "oligodendrocyte progenitor cell," etc. can encompass cells of the oligodendrocyte lineage, i.e. neural progenitor cells that ultimately give rise to oligodendrocytes, oligodendrocyte precursor cells, and mature and myelinating oligodendrocytes, which for the purposes of the present invention arise from a non-oligodendrocyte cell by experimental manipulation. Oligodendrocytes can be identified by markers specific for cells of the oligodendrocyte lineage as discussed below. Oligodendrocytes may have functional characteristics, that is, they may have the capacity of myelinating neurons; and the like. An "oligodendrocyte precursor" or "oligodendrocyte progenitor cell" is defined as a cell that is capable of giving rise to progeny that include oligodendrocytes. Oligodendrocytes are present in the assembled spheroids.

Oligodendrocytes are the myelin-forming cells of the central nervous system. An oligodendrocyte extends many processes which contact and repeatedly envelope stretches of axons. Subsequent condensation of these wrapped layers of oligodendrocyte membrane form the myelin sheath. One axon may contain myelin segments from many different oligodendrocytes.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

Methods of the Invention

Methods are provided for the development and use of in vitro Compositions and methods are provided for in vitro generation of functional human cortico-spinal-muscle assembled spheroids, which may be generated at least in part from human pluripotent stem cells (hPSCs). Complete cortico-spinal-muscle spheroids (hCS-hSC-hSkM) are assembled from component cultured cell systems, where each cultured cell system is designed to provide specific sets of neural and/or muscle cells, and which components are functionally integrated in the assembled spheroid. Functionally integrated cells interact in a physiologically relevant manner, e.g. forming synapses or neuromuscular junctions, transmitting signals, inducing muscle contractions, forming multicellular structures, and the like.

The methods comprise an initial step of differentiating pluripotent cells, including without limitation induced human pluripotent stem cells (hiPSC), into the component structures of (i) spinal cord spheroids (hSC) comprising motor neurons, and interneurons, which can be functionally integrated with skeletal muscle cells (hSkM) differentiated from pluripotent cells or from primary muscle progenitor cells to generate hSC-hSkM spheroids; and (ii) a cerebral cortical, or dorsal pallium structure (hCS) comprising glutamatergic neurons. The spheroids may also comprise neural progenitor cells, astrocytes, oligodendrocytes and the like.

Following the initial differentiation into the component spheroids, and integration of muscle cells and spinal cord, the hSC-hSkM spheroids and cortical spheroid(s) (hCS) are placed adjacent to each other in culture under conditions permissive for fusion or assembly of the two spheroids and generation of the integrated corticospinal system with new properties. In this case, the assembled hSC-hSkM-hCS spheroids comprises functionally integrated neurons of excitatory and inhibitory types, motor neurons and muscle, which provides a platform for analysis of the effect of agents on brain and spinal cord structure and function.

In some embodiments the neural cells are differentiated from induced human pluripotent stem cells (hiPSC). In some embodiments the hiPSC are derived from somatic cells obtained from neurologically normal individuals. In other embodiments the hiPSC are derived from somatic cells obtained from an individual comprising at least one allele encoding a mutation associated with a neural disease.

Generation of the component spheroids and cells comprised therein utilizes a multi-step process. Initially, hiPSC can be obtained from any convenient source, or can be generated from somatic cells using art-recognized methods. The hiPSC are dissociated from feeders (or if grown in feeder free, aggregated in spheroids of specific sizes) and grown in suspension culture in the absence of FGF2, preferably when dissociated as intact colonies. In certain embodiments the culture are feeder layer free, e.g. when grown on vitronectin coated vessels. The culture may further be free on non-human protein components, i.e. xeno-free, where the term has its usual art-recognized definition, for example referring to culture medium that is free of non-human serum.

To generate the spinal cord spheroids, hiPSCs are dissociated and grown in suspension; then induced to a neural fate by SMAD inhibitors, e.g. dorsomorphin at a concentration of from about 1 to 50 µM, about 2 to 25 µM, and may be around about 5 µM; and SB-431542 at a concentration of from about 2 to 100 µM, about 5 to 50 µM, and may be around about 10 µM. The cells are cultured in this medium for periods of from about 2 to about 5 days, and may be about 4 days; after which time the medium is supplemented with a GSK-3 inhibitor, e.g. CHIR 99021 at a concentration of from about 1 to 50 µM, about 2 to 25 µM, and may be around about 3 µM. The cells are maintained in the medium for an addition 1 to 3 days, and may be maintained for 2 days. CHIR may be maintained until day 18, or may be removed after day 6.

The cells are then moved to neural medium in the presence of retinoic acid at a concentration of from about 10 to 1 µM, from about 50 to 150 nM, and may be about 100 nM, FGF2 at a concentration of from about 0 to 50 ng/ml, from about 2.5 to 25 ng/ml and may be about 10 ng/ml; and EGF at a concentration of from about 1 to 50 ng/ml, from about 2.5 to 25 ng/ml and may be about 20 ng/ml, for a period of from about 3 to 7 days, and may be around about 5 days. The medium is then supplemented with an SHH pathway agonist, e.g. smoothened agonist (SAG) at a concentration of from about 0 to 1 µM, from about 50 to 150 nM, and may be about 100 nM. After about 5 to 9 days, e.g. after about 7 days, the medium is optionally supplemented with gamma secretase inhibitor, e.g. DAPT at a concentration of from about 1 to 25 µM, about 2 to 10 µM, and may be around about 2.5 µM, which supplement may be provided one, two, three or more times at intervals of from about 1 to 3 days. This completes the fate specification stage. Concentrations of RA and FGF2 may be titrated to achieve different rostro-caudal positions within the spinal cord (which may be determined by expression of HOX genes, with HOX4-HOX8 being cervical/brachial and HOX9-HOX11 being thoracic/lumbar). Concentrations of SAG may be titrated to achieve different dorso-ventral positions within the spinal cord (which may be determined by expression of PAX3 and OLIG2, among others).

The spheroids may then be maintained in culture in neural medium supplemented with BDNF at a concentration of from about 1 to 50 ng/ml, from about 2.5 to 25 ng/ml and may be about 20 ng/ml; IGF at a concentration of from about 1 to 50 ng/ml, from about 2.5 to 25 ng/ml and may be about 10 ng/ml, L-ascorbic acid at a concentration of from about 10 to 500 nM, from about 50 to 250 nM, and may be about 200 nM; and cAMP at a concentration of from about 10 to 500 nM, from about 50 to 150 nM, and may be about 62.5 nM. After such culture, the spheroids can be maintained for extended periods of time in neural medium in the absence of growth factors, e.g. for periods of 1, 2, 3, 4, 5, 6, 7, 8, 9, 10, 11, 12, 24, 36 months or longer.

Ventral spinal cord spheroids (hSC) comprise functional human cholinergic motor neurons; and excitatory and inhibitory interneurons. The relative proportion of these types of neurons can be shifted by modulating the Notch pathway through the optional inclusion of DAPT in the medium as described above. These functional motor neurons have the ability to promote muscle contractions in skeletal muscle cells.

Human skeletal muscle cells can be functionally integrated with hSC to generate hSC-hSkM spheroids through co-culture, where neuromuscular junctions are formed between the motor neurons and the muscle cells. The skeletal muscle cells can be cultured from various sources, e.g. from hPSCs, from primary skeletal myoblasts, etc. In some embodiments the hSkM are cultured in a 3-dimensional matrix, e.g. a gel matrix, which may be referred to as 3-D. In other embodiments the hSkM are cultured on a matrix-coated flat plate, referred to as a 2-D culture. The muscles cells are grown in skeletal muscle cell growth medium, and differentiate into long multi-nucleated fibers within about 5 to about 10 days.

The hSC and skeletal muscle cells are co-cultured in contact with each other, using either 2D or 3D muscle cell cultures in medium supplemented with L-ascorbic acid at a concentration of from about 10 to 500 nM, from about 50 to 250 nM, and may be about 200 nM; and cAMP at a concentration of from about 10 to 500 nM, from about 50 to 150 nM, and may be about 62.5 nM. The co-cultures have functional integration after about 5 days, about 7 days, or longer.

The hSC, or hSC-hSkM can be functionally integrated with separately cultured human cerebral cortical spheroids (hCSs), which include pyramidal glutamatergic neurons of all cortical layers. The resulting assembled spheroid forms corticospinal projections and provides for functional integration of muscles, motor neurons, interneurons and cortical neurons.

The hCS may be generated by the methods previously described, for example in Pasca et al. (2015) Nat. Methods 12(7):671-678, entitled "Functional cortical neurons and astrocytes from human pluripotent stem cells in 3D culture", herein specifically incorporated by reference.

For example, a suspension culture of hiPSC is induced to a neural fate. For neural induction, an effective dose of an inhibitor of BMP, and of TGFβ pathways is added to the medium, for a period at least about 2 days, at least about 3 days, at least about 4 days, at least about 5 days, and up to about 10 days, up to about 9 days, up to about 8 days, up to about 7 days, up to about 6 days, up to about 5 days. For example, dorsomorphin (DM) can be added at an effective dose of at least about 0.1 µM, at least about 1 µM, at least about 5 µM, at least about M, at least about 50 µM, up to about 100 M concentration, which inhibits bone morphogenetic protein (BMP) type I receptors (ALK2, ALK3 and ALK6). Other useful BMP inhibitors include, without limitation, A 83-01; DMH-1; K 02288; ML 347; SB 505124; etc. SB-431542 can be added at an effective dose of at least about 0.1 µM, at least about 1 µM, at least about 5 µM, at least about 10 µM, at least about 50 µM, up to about 100 µM concentration, which inhibits TGFβ signaling but has no effect on BMP signaling. An effective dose of a wnt inhibitor may be included in the culture medium, for example at a concentration of from about 0.1 µM to about 100 µM, and may be from about 1 µM to about 25 µM, depending on the activity of the inhibitor that is selected.

After about 5 days, about 6 days, about 7 days, about 8 days, about 9 days, about 10 days in suspension culture, the floating spheroids are moved to neural media to differentiate neural progenitors. The media is supplemented with an effective dose of FGF2 and EGF. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml.

To promote differentiation of neural progenitors into neurons, after about 1 week, about 2 weeks, about 3 weeks, about 4 weeks after FGF2/EGF exposure the neural medium is changed to replace the FGF2 and EGF with an effective dose of BDNF and NT3. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml.

The cortical spheroids are co-cultured with the hSC-hSkM spheroids in medium comprising BDNF, NT3, L-ascorbic acid and cAMP at the concentrations disclosed above. Assembly may be performed with spheroids after around about 30 days, about 60 days, about 90 days, about 120 days, about 150 days, about 180 days, about 210 of culture for the hCS spheroids; and after about 15 days, after about 25 days, after about 35 days, after about 45 days after about 50 days of culture for the hSC-hSkM spheroids. The resulting assembled spheroids are demonstrated to have a functional circuit from cortical neurons, motor neurons, and skeletal muscle.

Screening Assays

In screening assays for the small molecules, the effect of adding a candidate agent to functional assembled spheroids, i.e. hSC; hSC-hSkM; and hCS-hSC-hSkM and including without limitation at the initiation of fusion between the spinal cord, muscle and cortical spheroid components to determine the effect on neuronal projection, migration, neuromuscular junctions, synapse formation, cell death or survival (for neurodegeneration related assays) etc. in culture is tested with one or a panel of cellular environments, where the cellular environment includes one or more of: electrical stimulation including alterations in ionicity, stimulation with a candidate agent of interest, contact with other cells including without limitation neurons and neural progenitors, contact with infectious agents, e.g. rabies virus, polio virus, Zika virus, and the like, and where cells may vary in genotype, in prior exposure to an environment of interest, in the dose of agent that is provided, etc. Usually at least one control is included, for example a negative control and a positive control. Culture of cells is typically performed in a sterile environment, for example, at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free. The effect of the altering of the environment is assessed by monitoring multiple output parameters, including morphological, functional and genetic changes.

Examples of analytic methods comprise, for example, assessing the integration of motor neurons and muscles, and include various assays of muscle function, for example fatigue resistance measurement assay can be used to measure a muscle's resistance to fatigue and recovery time; lengthening and contraction protocol assessment measures the capability of a muscle to resist injury by measuring the contractile force before, during and after extending the muscle beyond its optimal length; contraction strength, specific force measurements; etc. Synaptic integration of neurons to neurons and to muscle can be assessed by using array tomography to detect pre- and post-synaptic proteins in hCS before and after fusion, such as the presence of PSDH95 or GPHN, which are postsynaptic proteins. To further examine these synaptic puncta 'synaptograms' consisting of a series of high-resolution sections through a single synapse may be obtained. Whole-cell voltage clamp recordings of synaptic responses can be performed on slices on the functional assembled spheroids, and to distinguish between excitatory postsynaptic currents (EPSCs, downward deflecting) and IPSCs (upward deflecting), a low Cl-solution may be used in the patch pipette with cells held at −40 mV.

Live imaging of cells may be performed and cells modified to express a detectable marker. Calcium sensitive dyes can be used, e.g. Fura-2 calcium imaging; Fluo-4 calcium imaging, Cal-590 calcium imaging, GCaMP6 calcium imaging, voltage imaging using voltage indicators such as voltage-sensitive dyes (e.g. di-4-ANEPPS, di-8-ANEPPS, and RH237) and/or genetically-encoded voltage indicators (e.g. ASAP1, Archer) can be used on the intact spheroids, assembled spheroids (including hSkM), or on cells isolated therefrom.

Methods of analysis at the single cell level are also of interest, e.g. as described above: live imaging (including confocal or light-sheet microscopy), single cell gene expression or single cell RNA sequencing, calcium imaging, immunocytochemistry, patch-clamping, flow cytometry and the like. Various parameters can be measured to determine the effect of a drug or treatment on the functional assembled spheroids or cells derived therefrom.

Parameters are quantifiable components of cells, particularly components that can be accurately measured, desirably in a high throughput system. A parameter can also be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorically determined epitopes associated with heterodimeric integrins. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, New York, (1996), Ninth edition, under the sections: Drugs Acting at Synaptic and Neuroeffector Junctional Sites; Cardiovascular Drugs; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome, for example using CRISPR mediated genomic engineering (see for example Shmakov et al. (2017) Nature Reviews Microbiology 15:169). Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; RNAi, encode a dominant negative mutation, or dominant or constitutively active mutations of native sequences; altered regulatory sequences, etc.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-5-5'-O-phosphorothioate, 3'-CH2-5-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs.

Agents are screened for biological activity by adding the agent to at least one and usually a plurality of cells, in one or in a plurality of environmental conditions, e.g. following stimulation with an agonist, following electric or mechanical stimulation, etc. The change in parameter readout in response to the agent is measured, desirably normalized, and the resulting screening results may then be evaluated by comparison to reference screening results, e.g. with cells having other mutations of interest, normal astrocytes, astrocytes derived from other family members, and the like. The reference screening results may include readouts in the presence and absence of different environmental changes, screening results obtained with other agents, which may or may not include known drugs, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to fluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

Neuronal activity parameters. Of interest for the functional assembled spheroids screening system are parameters related to the electrical properties of the neurons and muscle cells and therefore directly informative about function and activity. Methods to measure activity may sense the occurrence of action potentials (spikes), and contractions, or twitches. The characteristics of the occurrence of a single spike or multiple spikes either in timely clustered groups (bursts) or distributed over longer time (spike train) of a single neuron or a group of neurons indicate neuronal activation patterns and thus reflect functional neuronal properties, which can be described my multiple parameters. Such parameters can be used to quantify and describe changes in neuronal activity in the systems of the invention.

Neuronal activity parameters include, without limitation, total number of spikes (per recording period); mean firing rate (of spikes); inter-spike interval (distance between sequential spikes); total number of bursts (per recording period); burst frequency; number of spikes per burst; burst duration (in milliseconds); inter-burst interval (distance between sequential bursts); burst percentage (the portion of spikes occurring within a burst); total number of network bursts (spontaneous synchronized network activity); network burst frequency; number of spikes per network burst; network burst duration; inter-network-burst interval; inter-spike interval within network bursts; network burst percentage (the portion of bursts occurring within a network burst).

Quantitative readouts of neuronal activity parameters may include baseline measurements in the absence of agents or a pre-defined genetic control condition and test measurements in the presence of a single or multiple agents or a genetic test condition. Furthermore, quantitative readouts of neuronal activity parameters may include long-term recordings and may therefore be used as a function of time (change of parameter value). Readouts may be acquired either spontaneously or in response to or presence of stimulation or perturbation of the complete neuronal network or selected components of the network. The quantitative readouts of neuronal activity parameters may further include a single determined value, the mean or median values of parallel, subsequent or replicate measurements, the variance of the measurements, various normalizations, the cross-correlation between parallel measurements, etc. and every statistic used to a calculate a meaningful and informative factor.

Comprehensive measurements of neuronal activity using electrical or optical recordings of the parameters described herein may include spontaneous activity and activity in response to targeted electrical or optical stimulation, including, for example, ChR2 delivered through lentiviruses, AAVs or pseudo rabies viruses, Neurotransmitter uncaging such glutamate uncaging, GABA uncaging, nicotine uncaging, etc) of all neuronal cells or a subpopulation of neuronal cells within the integrated spheroids. Furthermore, spontaneous or induced neuronal activity can be measured in the self-assembled functional environment and circuitry of the neural culture or under conditions of selective perturbation or excitation of specific subpopulations of neuronal cells as discussed above.

In the provided assays, comprehensive measurements of neuronal activity can be conducted at different time points along neuronal maturation and usually include a baseline measurement directly before contacting the neural culture with the agents of interest and a subsequent measurement under agent exposure. Moreover, long-term effects of agents on neural maturation and development can be assessed by contacting the immature neural culture at an early time point with agents of interest and acquiring measurements of the same cultures after further maturation at a later time point compared to control cultures without prior agent exposure.

The system has applications towards modeling spinal cord injury, for example by severing corticospinal tract and testing drugs for regeneration or for reducing glial scar response. For certain experiments, hSC can be co-cultured with mouse developing limb (for example for specificity of axon pathfinding studies). Moreover, assembled hCS-hSC-hSkM or parts of it can be combined with neural crest-like cells to get Schwann cells for potential myelination of corticospinal projecting tract, can be combined with e.g. DRG-like spheroids and dorsal spinal cord for modeling of sensory circuit (e.g. pain research), can be paired with left-right ventral spinal cord for left-right locomotion modeling, to test drug responses in patients with myasthenia gravis, Lambert-Eaton disorders and other autoimmune disorders of the cortico-spinal tracts (GAD antibodies, NMDA receptor antibodies, etc) and related disorders. Lastly, the system can be used to identify muscle-derived survival factors for motor neurons, which can then be used to treat neurodegenerative disorders.

In some embodiments, standard recordings of neuronal activity of mature neural cultures are conducted after about 2 weeks, after about 3 weeks, after about 4 weeks, after about 6 weeks, after about 8 weeks following fusion (i.e. after mixing the different subdomain components of the culture). Recordings of neuronal activity may encompass the measurement of additive, synergistic or opposing effects of agents that are successively applied to the cultures, therefore the duration recording periods can be adjusted according to the specific requirements of the assay. In some embodiments the measurement of neuronal activity is performed for a predetermined concentration of an agent of interest, whereas in other embodiments measurements of neuronal activity can be applied for a range of concentrations of an agent of interest.

In some embodiments the provided assays are used to assess maturation of the neural culture or single components including motor neurons, GABAergic interneurons, glutamatergic neurons, astrocytes, oligodendrocytes, etc. Maturation of neuronal cells can be measured based on morphology, by optically assessing parameters such as neuromuscular junctions, dendritic arborization, axon elongation, total area of neuronal cell bodies, number of primary processes per neuron, total length of processes per neuron, number of branching points per primary process as well as density and size of synaptic puncta stained by synaptic markers such as synapsin-1, synaptophysin, bassoon, PSD95, anti-BTX antibodies (for neuromuscular junctions) and Homer. Moreover, general neuronal maturation and differentiation can be assessed by measuring expression of marker proteins such as MAP2, TUJ-1, NeuN, Tau, PSA-NCAM, and SYN-1 alone or in combination using FACS analysis, immunoblotting, or fluorescence microscopy imaging, patch clamping. Maturation and differentiation of neuronal subtypes can further be tested by measuring expression of specific proteins. For excitatory neuronal cells this includes staining for e.g. VGLUT1/2, GRIA1/2/3/4, GRIN1, GRIN2A/B, GPHN etc. For inhibitory neuronal cells this includes staining for e.g. GABRA2, GABRB1, VGAT, and GAD67. For cholinergic motor neurons this includes staining for e.g. CHAT and VACHT.

The results of an assay can be entered into a data processor to provide a dataset. Algorithms are used for the comparison and analysis of data obtained under different conditions. The effect of factors and agents is read out by determining changes in multiple parameters. The data will include the results from assay combinations with the agent(s), and may also include one or more of the control state, the simulated state, and the results from other assay combinations using other agents or performed under other conditions. For rapid and easy comparisons, the results may be presented visually in a graph, and can include numbers, graphs, color representations, etc.

The dataset is prepared from values obtained by measuring parameters in the presence and absence of different cells, e.g. genetically modified cells, cells cultured in the presence of specific factors or agents that affect neuronal function, as well as comparing the presence of the agent of interest and at least one other state, usually the control state, which may include the state without agent or with a different agent. The parameters include functional states such as synapse formation and calcium ions in response to stimulation, whose levels vary in the presence of the factors. Desirably, the results are normalized against a standard, usually a "control value or state," to provide a normalized data set. Values obtained from test conditions can be normalized by subtracting the unstimulated control values from the test values, and dividing the corrected test value by the corrected stimulated control value. Other methods of normalization can also be used; and the logarithm or other derivative of measured values or ratio of test to stimulated or other control values may be used. Data is normalized to control data on the same cell type under control conditions, but a dataset may comprise normalized data from one, two or multiple cell types and assay conditions.

The dataset can comprise values of the levels of sets of parameters obtained under different assay combinations. Compilations are developed that provide the values for a sufficient number of alternative assay combinations to allow comparison of values.

A database can be compiled from sets of experiments, for example, a database can contain data obtained from a panel of assay combinations, with multiple different environmental changes, where each change can be a series of related compounds, or compounds representing different classes of molecules.

Mathematical systems can be used to compare datasets, and to provide quantitative measures of similarities and differences between them. For example, the datasets can be analyzed by pattern recognition algorithms or clustering methods (e.g. hierarchical or k-means clustering, etc.) that use statistical analysis (correlation coefficients, etc.) to quantify relatedness. These methods can be modified (by weighting, employing classification strategies, etc.) to optimize the ability of a dataset to discriminate different functional effects. For example, individual parameters can be given more or less weight when analyzing the dataset, in order to enhance the discriminatory ability of the analysis. The effect of altering the weights assigned each parameter is assessed, and an iterative process is used to optimize pathway or cellular function discrimination.

The comparison of a dataset obtained from a test compound, and a reference dataset(s) is accomplished by the use of suitable deduction protocols, AI systems, statistical comparisons, etc. Preferably, the dataset is compared with a database of reference data. Similarity to reference data involving known pathway stimuli or inhibitors can provide an initial indication of the cellular pathways targeted or altered by the test stimulus or agent.

A reference database can be compiled. These databases may include reference data from panels that include known agents or combinations of agents that target specific pathways, as well as references from the analysis of cells treated under environmental conditions in which single or multiple environmental conditions or parameters are removed or specifically altered. Reference data may also be generated from panels containing cells with genetic constructs that selectively target or modulate specific cellular pathways. In this way, a database is developed that can reveal the contributions of individual pathways to a complex response.

The effectiveness of pattern search algorithms in classification can involve the optimization of the number of parameters and assay combinations. The disclosed techniques for selection of parameters provide for computational requirements resulting in physiologically relevant outputs. Moreover, these techniques for pre-filtering data sets (or potential data sets) using cell activity and disease-relevant biological information improve the likelihood that the outputs returned from database searches will be relevant to predicting agent mechanisms and in vivo agent effects.

For the development of an expert system for selection and classification of biologically active drug compounds or other interventions, the following procedures are employed. For every reference and test pattern, typically a data matrix is generated, where each point of the data matrix corresponds to a readout from a parameter, where data for each parameter may come from replicate determinations, e.g. multiple individual cells of the same type. As previously described, a data point may be quantitative, semi-quantitative, or qualitative, depending on the nature of the parameter.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

Classification rules are constructed from sets of training data (i.e. data matrices) obtained from multiple repeated experiments. Classification rules are selected as correctly identifying repeated reference patterns and successfully distinguishing distinct reference patterns. Classification rule-learning algorithms may include decision tree methods, statistical methods, naive Bayesian algorithms, and the like.

A knowledge database will be of sufficient complexity to permit novel test data to be effectively identified and classified. Several approaches for generating a sufficiently encompassing set of classification patterns, and sufficiently powerful mathematical/statistical methods for discriminating between them can accomplish this.

The data from cells treated with specific drugs known to interact with particular targets or pathways provide a more detailed set of classification readouts. Data generated from cells that are genetically modified using over-expression techniques and anti-sense techniques, permit testing the influence of individual genes on the phenotype.

A preferred knowledge database contains reference data from optimized panels of cells, environments and parameters. For complex environments, data reflecting small variations in the environment may also be included in the knowledge database, e.g. environments where one or more factors or cell types of interest are excluded or included or quantitatively altered in, for example, concentration or time of exposure, etc.

For further elaboration of general techniques useful in the practice of this invention, the practitioner can refer to standard textbooks and reviews in cell biology, tissue culture, embryology, stem cell biology, human development and neurobiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Example 1

Generation of Functional Cortico-Spinal Assembled Spheroids from Human Pluripotent Stem Cells Described herein is a novel approach to study human cortico-spinal-muscle development using three-dimensional (3D) cultures generated from human pluripotent stem cells (hPSCs). We first generated hPSC-derived ventral spinal cord spheroids (hSCs), which include functional, cholinergic motor neurons able to promote muscle contraction when co-cultured with human skeletal muscle (hSkM) that are cultured either in 2D or 3D. Fusion of human cerebral cortical spheroids (hCSs), which include pyramidal glutamatergic neurons of all cortical layers, with hSC-hSkM in cortico-spinal-muscle assembled spheroids results in the formation of corticospinal projections. Using a combination of viral tracing, calcium imaging and electrophysiological methods we present evidence of the formation of the first in vitro model of the human cortico-spinal-muscular circuit, which is useful as a platform for modeling CNS injury and disease and for testing therapeutics.

Generation of human ventral spinal cord spheroids (hSC). Human pluripotent stem cells (hPSCs) were cultured on inactivated mouse embryonic fibroblast feeders (Embryo-Max PMEF) in hPSC medium containing DMEM/F12, knockout serum (20%), non-essential amino-acids (1 mM), GlutaMax (1:200), β-mercaptoethanol (0.1 mM), penicillin and streptomycin (1:100), and supplemented with FGF2 (100 ng/ml). To generate hSC, intact hPSC colonies were lifted from the culture plates using dispase and transferred into ultralow-attachment plates in hPSC medium supplemented with the SMAD inhibitors dorsomorphin (5 μM) and SB-431542 (10 μM). After day 1, cell medium was changed every day and supplemented with dorsomorphin and SB-431542.

From day 4 in suspension, cultures were supplemented with the GSK-3 inhibitor CHIR 99021 (3 μM). On day 6, spheroids were transferred to neural medium containing neurobasal-A, B-27 supplement without vitamin A, Gluta-Max (1:100), penicillin and streptomycin, and supplemented with retinoic acid (RA, 100 nM), EGF (20 ng/ml) and FGF-2 (10 ng/ml). On day 11 of differentiation spheroids were supplemented with the SHH pathway agonist Smoothened Agonist (SAG, 100 nM), in addition to the compounds described above. From day 7 onwards, media was changed every other day. For the hSC+D condition, spheroids received the gamma-secretase inhibitor DAPT (2.5 μM) on days 19, 21 and 23. From day 19, once the initial fate specification stage is finalized, hSCs were transferred to neural medium containing neurobasal-A, B-27 supplement without vitamin A, N-2 supplement, GlutaMax (1:100), penicillin and streptomycin (1:100), and supplemented with BDNF (20 ng/ml), IGF (10 ng/ml), L-Ascorbic Acid (AA, 200 nM) and cAMP (62.5 nM). A schematic showing the different recipes is presented in FIG. 1A.

Generation of muscle cultures and neuromuscular assembled spheroids (hSC-hSkM). Human skeletal myoblasts were obtained from Thermo Fisher Scientific (A12555) and maintained in an undifferentiated state with Skeletal Muscle Cell Growth Medium (Lonza or PromoCell). Human muscle cells can also be generated from hPSC.

For generation of 2D muscle cultures, 30,000 hSkM were plated on Geltrex-coated 24-well tissue culture plates. Skeletal Muscle Cell Growth Medium was changed to Skeletal Muscle Cell Differentiation Medium (PromoCell) once hSkM were 90% confluent (2-3 days after plating). With medium changes every other day, hSkM differentiate into long multi-nucleated fibers within 5-10 days. For generation of 3D muscle cultures, 1-3×10$^5$ hSkM were plated into silicone wells (80369, Ibidi) with 50 μl Geltrex. Wells containing hSkM and Geltrex were placed in the incubator for 30 minutes to allow Geltrex gelling and later placed in 6-well tissue culture plates with Skeletal Muscle Cell Growth Medium. The next day, silicone wells containing hSkM were placed into 6-well ultralow-attachment plates, and medium was changed every 2-3 days. After approximately one week, medium was changed to Skeletal Muscle Cell Differentiation Medium to allow for differentiation of hSkM for ~two weeks with medium changes every 2-3 days.

In order to generate neuromuscular assembled spheroids, hSC were co-cultured with differentiated 2D or 3D hSkM in medium containing DMEM/F12, non-essential amino-acids (1 mM), Insulin-Transferrin-Selenium (ITS, 1:100), and penicillin and streptomycin (1:100), and supplemented with L-Ascorbic Acid (AA, 200 nM) and cAMP (62.5 nM). For co-culture with 2D hSkM, hSC were placed on top of hSkM in 24-well plates and allowed to attach for 2 days before changing medium. For co-culture and assembly with 3D hSkM, both hSkM 3D constructs (removed from silicone wells) and hSC were placed on top of tissue culture inserts (353090, Fisher Scientific) so that they were in contact with one another and allowed to fuse. Media was changed every other day.

Generation of cortico-spinal assembled spheroids. In order to generate cortico-spinal (hCS-hSC) assembled spheroids, hCS and hSC were generated separately, and later assembled by placing them in close proximity with each other in 1.5 ml microcentrifuge tubes for 3 days in an incubator. Neural cell media used for assembly contained neurobasal-A, B-27 supplement without vitamin A, Gluta-Max (1:100), penicillin and streptomycin (1:100), and was supplemented with BDNF (20 ng/ml), NT3 (20 ng/ml), L-Ascorbic Acid (AA, 200 nM) and cAMP (62.5 nM). Media was carefully changed on day 2, and on the third day, assembled spheroids were placed in 24-well ultralow attachment plates in the neural medium described above using a cut P1000 pipette tip. After this, media was changed every 3-4 days. hCS was generated by previously described methods (Pasca et al., 2015; Birey et al., 2017). Assembly was performed between days (d) 60 and 130 of hCS and between d25 and d50 of hSC. For some experiments hCS were virally labeled with AAV-DJ1-hSYN1::YFP seven to ten days prior to assembly.

For tracing experiments with AG Rabies, hCS were labeled with AAV-DJ1-DIO-mCherry and hSC were labeled with AG Rabies-eGFP-Cre and AAV-DJ1-EF1a-CVS-G-WPRE-pGHpA. Seven days after viral infection, hCS and hSC were assembled and maintained in culture with media changes every 3-4 days for 30 days. After 30 days, assembled spheroids were fixed with 4% paraformaldehyde and processed for immunostaining.

For cortico-spinal-muscle assembled spheroids, hCS-hSC assembled spheroids were placed on tissue culture inserts and positioned so that hSC was in contact with the 3D hSkM constructs. Media was changed every other day.

For glutamate uncaging experiments, MNI-caged-L-glutamate was used at a final concentration of 3.3 mM. The FRAP module of the Leica SP8 confocal microscope was used to uncage glutamate using UV light. Quantification of the speed of contraction was done with the ImageJ plugin Musclemotion (Sala & van Meer et al., 2017).

Results

Generation of functional ventral spinal cord spheroids (hSC). To specify spheroids resembling ventral spinal cord, human pluripotent stem cell (hPSC) colonies lifted with dispase were first patterned by double SMAD inhibition towards neuroectoderm and later exposed to CHIR, retinoic acid (RA) and the SHH agonist SAG (FIG. 1A). Gene expression analysis of key transcription factors in spinal cord patterning and development show hSC transition from a neuroectoderm signature at days 5 and 10 (high SOX1 and high PAX6) to a ventral spinal cord identity starting on day 12 (high OLIG2, NKX6.1 and IRX3, low PAX6 and SOX1) (FIG. 1B). By day 20, OLIG2, the motor neuron domain marker in the ventral spinal cord, is highly expressed throughout hSC when examined by immunocytochemistry (FIG. 1C).

Motor neurons, which are responsible for muscle contraction and are typically characterized by expression of the neurofilament marker SMI-32 and the acetylcholine synthesizing enzyme CHAT, are generated from the motor neuron (MN) OLIG2+ domain of the ventral spinal cord during development. In hSC, SMI-32+ CHAT+ motor neurons can be observed early on after specification (FIG. 1D).

Other than the MN domain containing cholinergic motor neurons, the ventral spinal cord is composed of V0-V3 domains containing excitatory and inhibitory interneurons, so the presence of these cells in hSC was next examined. Analysis of V0-V3 markers by qPCR showed that all ventral domains of the spinal cord are represented in hSC (FIG. 1E, and an example of the different neuron populations in hSC at d45 is shown in FIG. 1F). Moreover, by modulating the Notch pathway with the gamma-secretase DAPT, the relative proportion of each of these domains could be shifted, with higher expression of the MN markers ISL1 and HB9 and lower expression of some interneuron markers (GATA3, EN1, EVX1) in the DAPT+condition (FIGS. 1A and 1E).

Figure 1G:
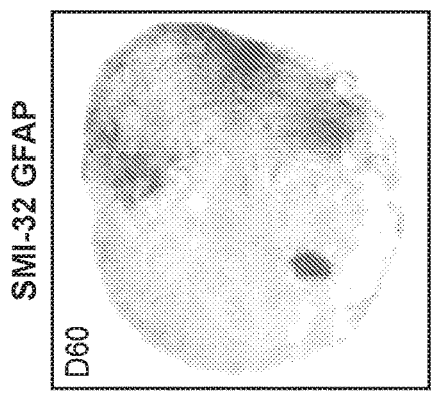
Figure 1H:
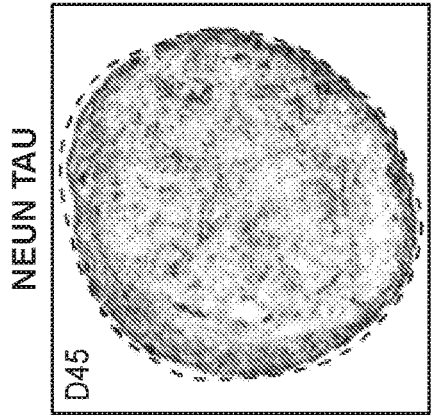
Figure 1I:
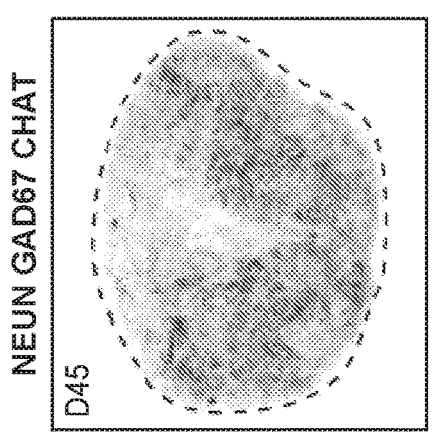

Next, the cytoarchitecture of hSC was examined by immunocytochemistry and noticed that in the DAPT+hSC condition, cell bodies were found on the inside of the spheroid, while axons were found on the outside of hSC (FIG. 1G), an architecture reminiscent of the mammalian spinal cord. From day 60, astrocytes were found in both hSC conditions (FIG. 1H), while oligodendrocytes were observed from day 75 (FIG. 1I).

Figure 1J:
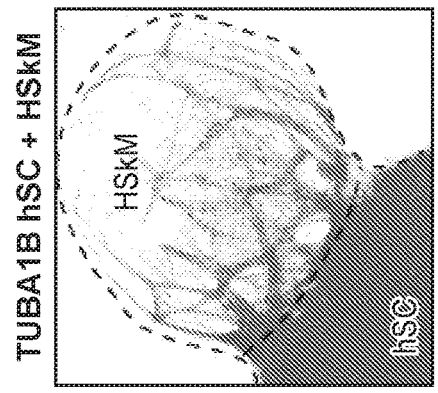
Figure 1K:
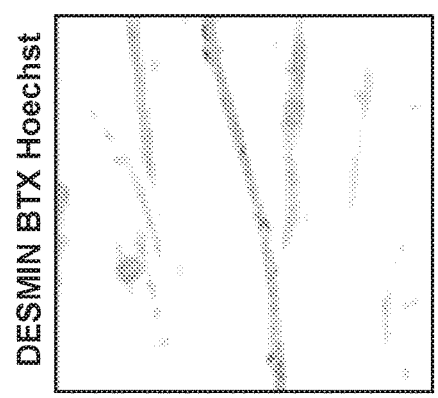
Figure 1L:
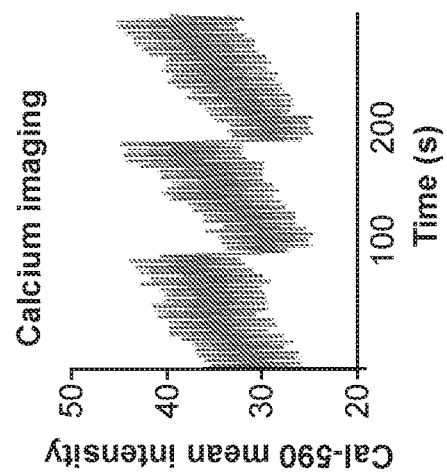
Figure 1M:
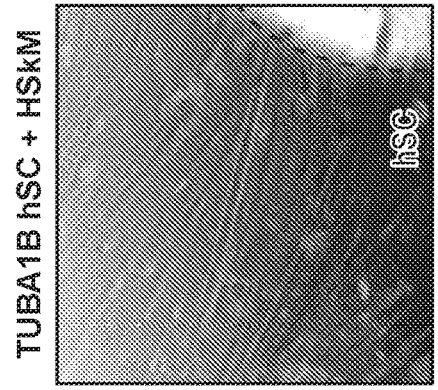

Next, in order to explore the functional properties of hSC, these spheres were co-cultured with 2D differentiated primary human skeletal myoblasts (hSkM). After seven days of co-culture, extensive projections from the hSC to the hSkM were observed using a TUBA1B GFP-tagged hiPSC line (FIG. 1J). Loading of hSkM with the calcium dye Cal-590 showed dynamic intracellular calcium transients only if hSkM were cultured with hSC (FIG. 1K). Moreover, labeling of hSkM that had been co-cultured with hSC with α-Bungarotoxin (BTX) showed the sites where neuromuscular junctions were formed (FIG. 1L). Finally, hSC can also be assembled with 3D hSkM to create hSC-hSkM assembled spheroids (FIG. 1M).

Generation of cortico-spinal-muscle assembled spheroids (hCS-hSC-hSkM). To develop a model to study the development and function of the cortico-spinal tract, hCS were virally labeled using AAV-DJ1-hSYN1::YFP and 7 to 10 days later they were assembled with hSC (FIG. 2A). Live imaging in intact hCS-hSC assembled spheroids over time showed hCS-derived hSYN-YFP cells projecting to hSC (FIG. 2B,C) with little migration. Next, in order to explore what cell types project from hCS to hSC, a viral tracing strategy using ΔG Rabies was employed. hSC was labeled with a G-deleted rabies vector that contained eGFP and Cre, as well as AAV-G to allow transneuronal transfer of ΔG Rabies-eGFP-Cre. hCS, in turn, was labeled with an AAV-DIO-mCherry that could only be expressed upon Cre recombination. After hCS-hSC assembly, hCS neurons projected to hSC, where they received ΔG Rabies-eGFP-Cre from hSC neurons. If recombination was successful, hCS started expressing mCherry. In this way, all hCS neurons that projected to hSC could be labeled with mCherry (FIG. 2D,E). Moreover, immunocytochemistry for cortical markers could tell us which cells projected. CTIP2, a marker for layer V corticospinal neurons during development, was expressed in a significant number of GFP+mCherry+hCS cells (FIG. 2F).

The next step to create the complete cortico-spinal circuit was to assemble hCS-hSC with 3D hSkM (FIG. 3A). This was done using tissue culture inserts to provide hSkM with a firm substrate. After assembly, hCS Syn-YFP-labeled neurons projected to hSC, hSC extended projections to hSkM, and hSkM could be seen to spontaneously contract (FIG. 3B). Quantification of the number of contractions over a two minute period in hSC-hSkM or hCS-hSC-hSkM showed that hSkM in assembled spheroids that included a hCS contracted significantly more than hSkM in assembled spheroids that only included a hSC (FIG. 3C-E), suggesting that hCS modulate muscle contraction in a cortico-spinal-muscle circuit model.

In order to confirm this, we used glutamate uncaging to stimulate specific areas of the hCS-hSC-hSkM assembloid. First, glutamate was uncaged on the hSC (FIG. 3F) and robust contractions of hSkM were observed (FIG. 3G). This contraction could be blocked with the acetylcholine receptor blocker tubocurarine (100 μM, FIG. 3H). Next, glutamate was uncaged on the hCS (FIG. 3I), and in this case contractions were either accelerated or stopped (FIG. 3J,K), which demonstrated that hCS activity can control and modulate muscle contraction through its spinal cord connections.

Significance and Applications

This is the first time where the complete, functional cortico-spinal/motor unit could be assembled in vitro using human-derived cells. We now have a model that we can use to study the interactions between the components of this circuit and what goes wrong when these interactions are disrupted during injury or disease in a human context.

This model is useful in study of the development of the cortico-spinal tract in humans as well as the formation of neuromuscular junctions and motor units. As well as understanding development, this system is useful to model disorders of the cortico-spinal/motor unit. Some of these include injuries of the spinal cord, neurodevelopmental and neurodegenerative disorders that affect the corticospinal tract like spinal muscular atrophy (SMA) and amyotrophic lateral sclerosis (ALS), or disorders with a neuroimmune component like myasthenia gravis, Lambert Eaton or multiple sclerosis (MS). This system has the advantage of providing the unique opportunity of using patient-derived iPS cells. In this way, assembled spheroids can be generated combining control and patient cells (e.g. Ctrl-hCS with patient-hSC) to piece apart their specific contributions to the system. In addition, this model is useful as a platform for large-scale drug screening for disease-relevant targets, or as a platform for large-scale viral screening for circuit-specific gene therapy.

Example 2

One of the main functions of the central nervous system is to direct the interaction of the body with the environment by controlling motor output. To achieve this, neurons projecting from the cerebral cortex control neurons in the spinal cord to stimulate muscles and generate movement. Injury or degeneration of this cortico-spinal-muscle circuit results in severe motor dysfunction. While components of this pathway have been generated and studied in isolation or using rodent explants, the in vitro derivation and assembly of this three-part system has not yet been achieved with human cells.

Here, we show the generation of three dimensional spheroids from human pluripotent stem cells that resemble the spinal cord and include a diversity of cell types including motor neurons. Fusion of spinal spheroids with spheroids resembling the cerebral cortex results in specific corticofugal projections extending from the cortical to the spinal component as assessed by retrograde viral tracing. Intact three-dimensional cortico-spinal spheroids can also be connected with three dimensional human skeletal muscle. This preparation, called a cortico-spinal-muscle assembloid, enables the formation of in vitro circuits that can be readily probed using glutamate uncaging and optogenetic approaches. Neuronal stimulation of cortical cells in three-component assembloids reliably results in muscle contraction via activation of spinal spheroids. This system will enable in vitro modeling of muscle activation by cortico-spinal networks and will allow for the interrogation of cortico-spinal-motor pathways and other circuits in human disease.

The main function of the cortico-spinal circuit is to control spinal cord activity and motor output. During development, glutamatergic neurons in deep layers of the cerebral cortex innervate the spinal cord where they modulate local circuits and ultimately control muscle contraction (FIG. 1a). We have previously developed an approach to model complex cellular interactions during human brain development by specifying region-specific organoids called spheroids and then fusing them in vitro to generate three-dimensional (3D) assembloids. However, in vitro derivation and assembly of a functional multi-synaptic circuit from human cells has not been achieved. Here, we leverage this approach to generate and assemble a three-component corticospinal-muscle circuit that includes long-range projections between spheroids resembling the cerebral cortex and the spinal cord, and that can be manipulated in vitro to control human muscle contraction.

Figure 4G:
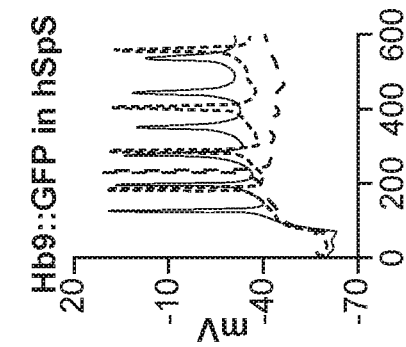
FIG. 4. Generation of hSpS and hCS-hSpS assembloids from hiPS cells a, Scheme illustrating the main cellular components of the cortico-spinal-muscle system. b, Scheme illustrating the generation of human cortical spheroids (hCS) and human spinal spheroids (hSpS) from hiPS cells. c, Gene expression of neuroectoderm (PAX6, SOX1) and ventral spinal cord-related (OLIG2, NKX6-1) gene markers at 5, 10, 12 and 18 days (D) of hSpS in vitro differentiation (n=3 hiPS cell lines; two-way ANOVA, interaction $F(9, 32)=3.29$, $P=0.005$). d, Immunocytochemistry in cryosections of hSpS showing ventral spinal cord progenitor markers OLIG2 and NKX6-1 at day 18 of in vitro differentiation. e, t-SNE visualization of single cell gene expression of hSpS at day 45 of in vitro differentiation (n=7,888 cells; $BD_{TM}$ Rhapsody system) showing 10 main clusters that include a spinal motor neuron (MN) cluster. f, Boxplots for neurotransmitter-related genes enriched in each of the single cell clusters (VGAT also called SLC32A1, GLYT2 also called SLC6A5, CHT1 also called SLC5A7, VACHT also called SLC18A3, VGLUT2 also called SLC17A6). g, h, Immunocytochemistry in cryosections of hSpS showing motor neuron markers at day 30 of in vitro differentiation. i, Immunocytochemistry showing a *Lenti*-Hb9::GFP neuron in an hSpS cryosection. j, Whole-cell current-clamp recording from an Hb9::GFP cell showing action potential generation in response to depolarizing current injections. k, Scheme illustrating the fusion of hCS and hSpS to form hCS-hSpS assembloids. Cells in hCS are labeled with AAV-hSYN1::eYFP before assembly. l, Immunocytochemistry of hCS-hSpS assembloid cryosections 30 days after fusion (daf). m, Quantification of hCS-derived eYFP coverage in hSpS area at 5, 10 and 20 daf in hCShSpS assembloids (n=3 hiPS cell lines, Kruskal-Wallis test P<0.0001 with Dunn's multiple test comparison: P=0.009 for 10 daf versus 5 daf, **P<0.0001 for 20 daf versus 5 daf). Data represent mean±s.e.m. Scale bars, 10 μm (g, i), 20 μm (h), 50 μm (d, l).
Figure 4H:
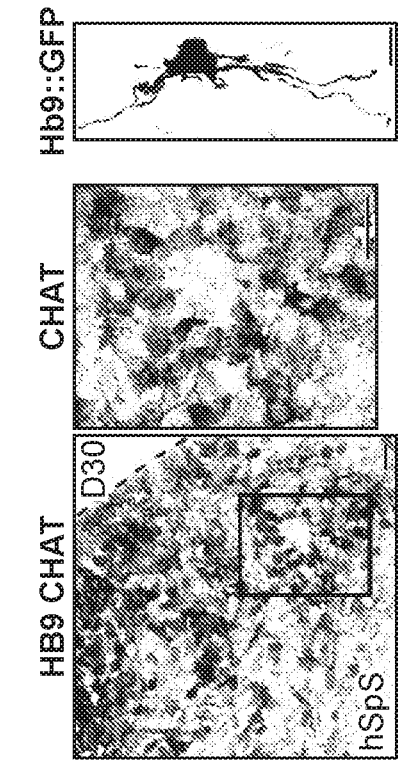
Figure 9A:
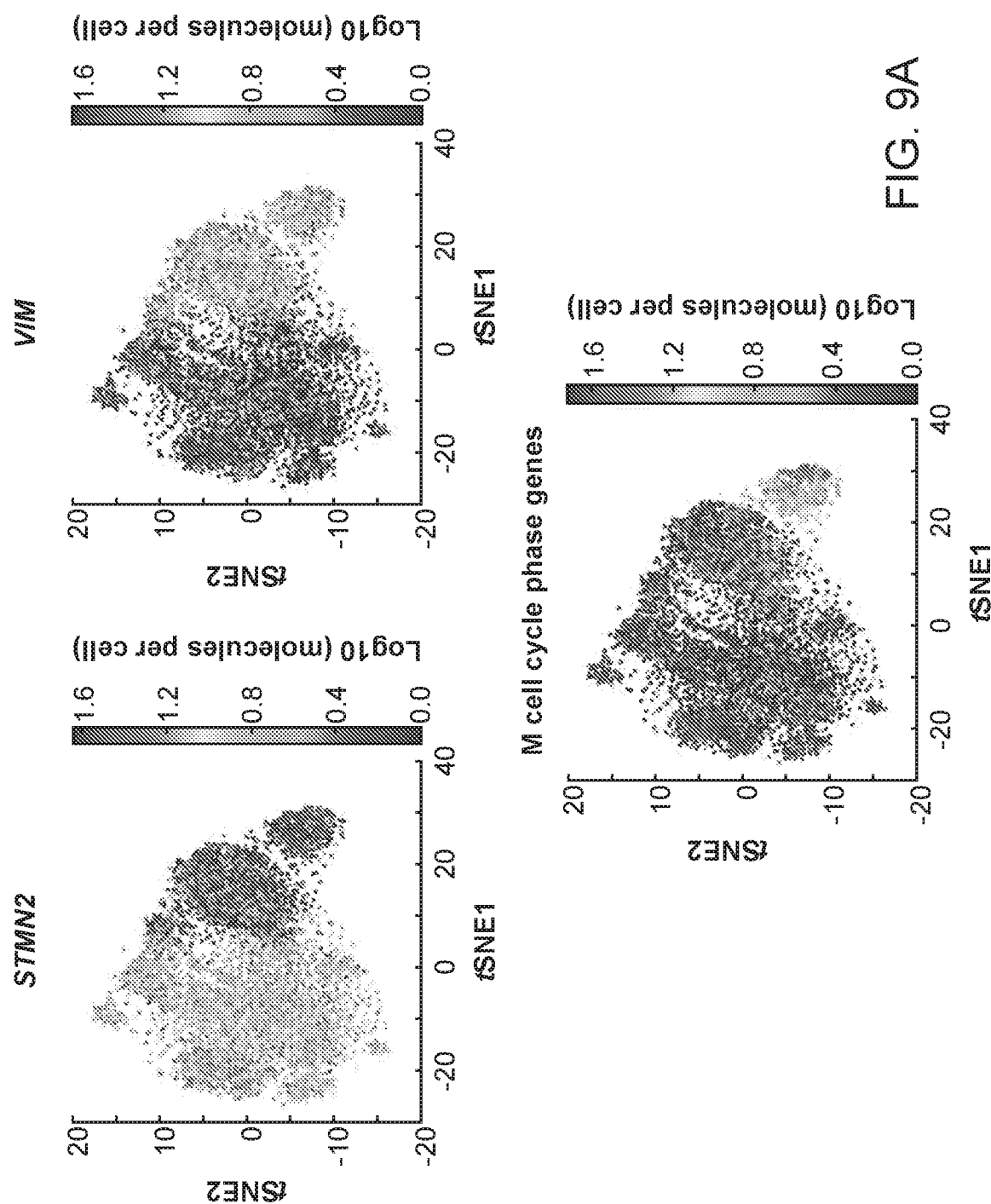
FIG. 9. Single-cell gene expression of hSpS at day 45 of differentiation a, t SNE visualization of single cell gene expression of hSpS at day 45 of in vitro differentiation (n=7,888 cells; $BD_{TM}$ Rhapsody system) showing the distribution of expression of the neuronal marker STMN2, the progenitor marker VIM and of a set of genes associated with the M cell cycle phase (AURKA, AURKB, TPX2, UBE2C, HMMR, TOP2A, HMGB2, CCNB1, NUSAP1, NUF2, CDC6, HIST1H4C, BIRC5, CKS2). b, Top genes in each of the ten clusters shown in FIG. 4e (proportion of molecules per cells). c, Box plots for genes enriched in each t SNE cluster shown in FIG. 1e. d, Distribution of cells in conditions hSpS and hSpS (−DAPT) in t-SNE plot. e, Correlation of hSpS and hSpS (−DAPT) conditions ($R_2$=0.85, P<0.0001). f, Proportion of cells per condition in each of the ten clusters ($X^2$ test, hSpS versus hSpS (−DAPT); P<0.0001).

To generate cortico-spinal assembloids, we first generated human spinal spheroids (hSpS) starting from hiPS cells (FIG. 4b). In the developing spinal cord, signaling gradients along the rostro-caudal and dorso-ventral axes specify the fate of neural progenitors and instruct their neuronal identify (FIG. 9a, b). More specifically, rostrocaudal fates are controlled by the WNT, retinoic acid (RA) and FGF pathways, while ventral fates, including the specification of spinal motor neurons, are regulated by sonic hedgehog (SHH).

Figure 9B:
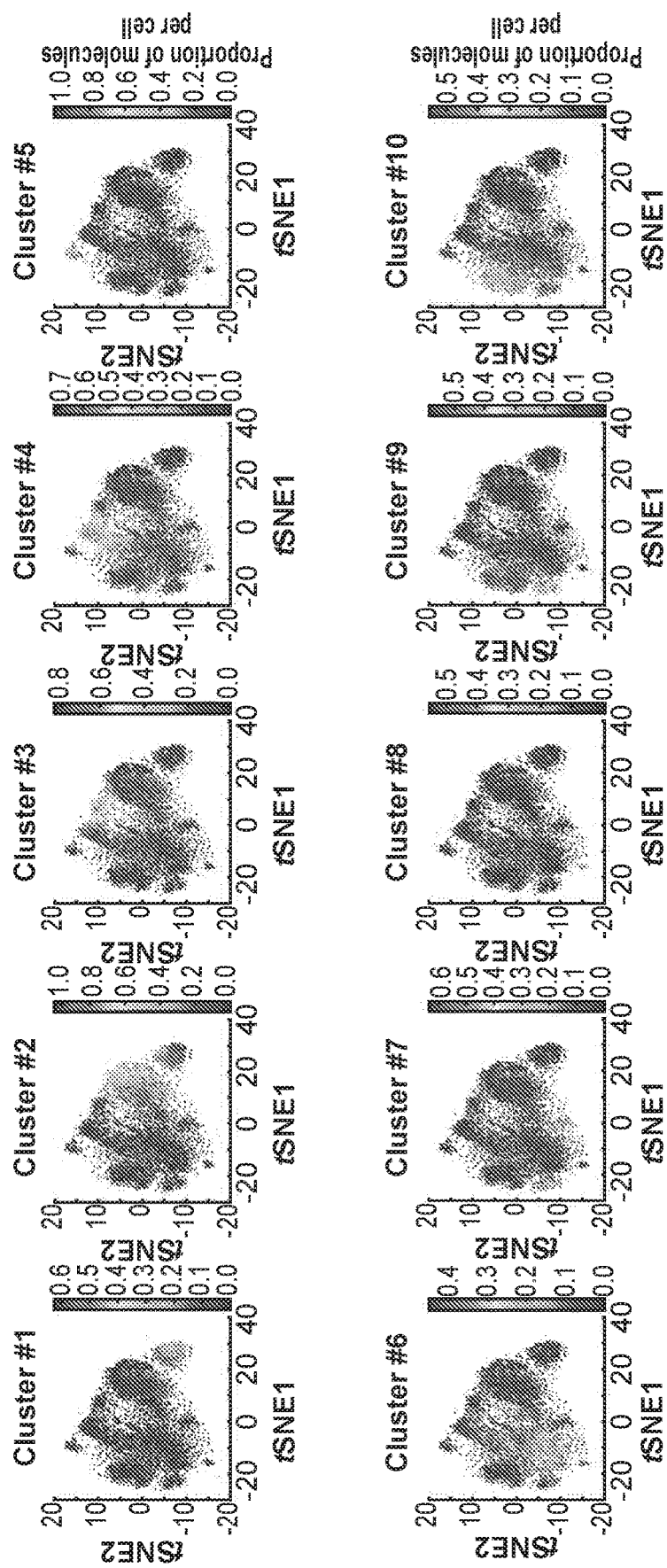
Figure 9C:
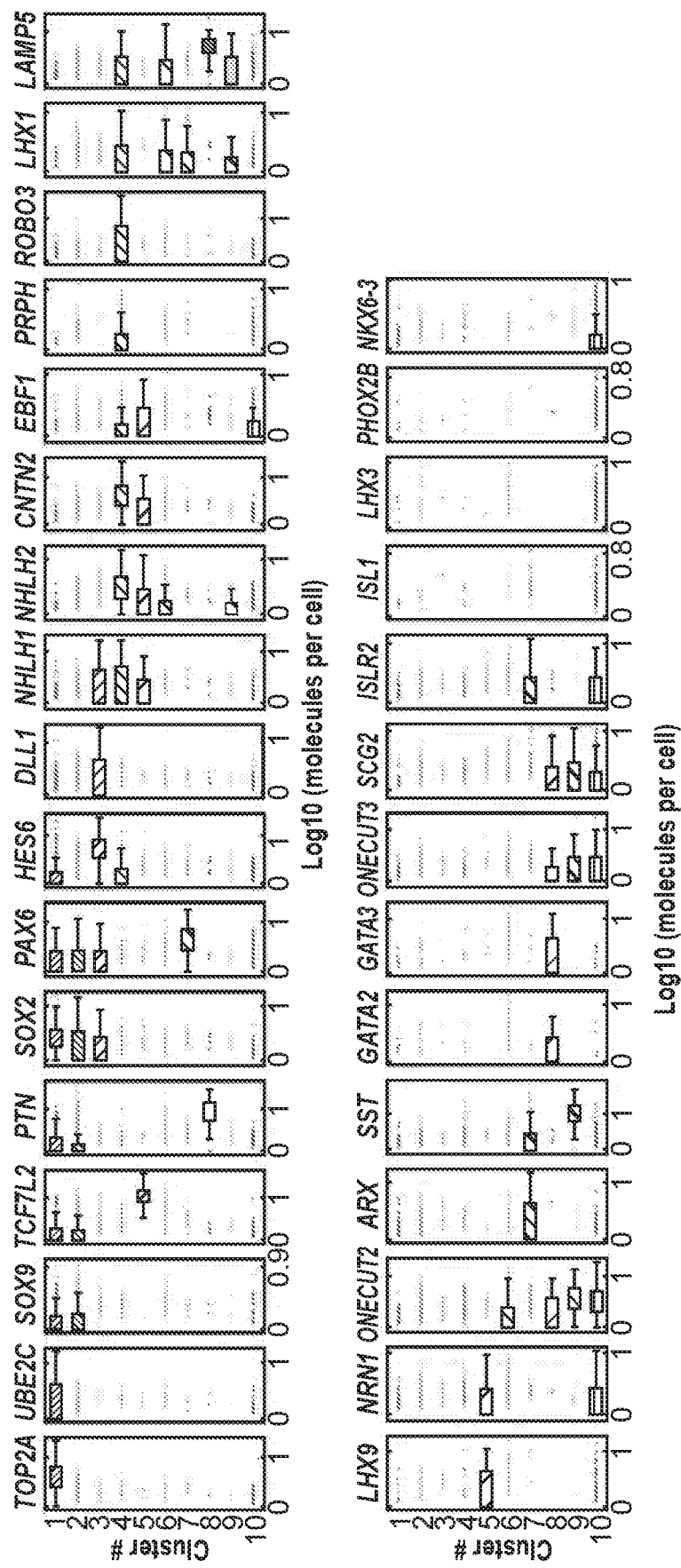

To establish hSpS differentiation conditions, we designed a combinatorial approach, where we used FGF-2, RA, and WNT and SHH modulators at varying concentrations following neural ectoderm specification of early spheroids. The combination of these factors resulted in 12 differentiation conditions (FIG. 9c). Briefly, hiPS cell colonies were lifted from plates using the enzyme dispase, moved to ultra-low attachment plates to form spheroids and exposed to dual SMAD inhibition as we have previously described. Starting on day 4 of in vitro differentiation, neural spheroids were exposed to 3 µM of the WNT activator CHIR-99021, and to 20 ng/ml EGF from day 6 onward. Neural spheroids also received a combination of RA (0.01 or 0.1 µM) and FGF-2 (0, 10 or 20 ng/ml) from day 6, and the SHH activator smoothened agonist (SAG; 0, 0.01, 0.1 or 1 µM) from day 11.

To determine the fate of the resulting spheroids in each of the 12 conditions, we assessed gene expression of 16 markers at day 20 of in vitro differentiation (FIG. 9d-g). We found that exposure to high levels of RA and low levels of FGF-2 results in more rostral fates, as shown by the expression pattern of HOXA2 (FIG. 9d; P=0.002). In contrast, exposure to low levels of RA and high levels of FGF-2 yields more caudal fates, as illustrated by expression of HOXC9 (FIG. 9d; P=0.002). High SAG exposure is associated with higher expression of ventral progenitor marker genes such as OLIG2, NKX6-1 and FOXA2 and the post-mitotic markers CHX10 and ISL1 (FIG. 9e, f; P=0.001 for Olig2, P=0.002 for NKX6-1, P<0.0001 for FOXA2, P=0.007 for CHX10, and P=0.01 for ISL1). Ventral identity was also confirmed by immunocytochemistry in hSpS 4 cryo-sections (FIG. 9f).

Based on this, we chose to pursue condition #8 for further experiments. Condition #8, which we refer to as hSpS from now on, included 0.1 µM RA, 0.1 µM SAG and 10 ng/ml FGF-2. In this condition, the neuroectodermal markers SOX1 and PAX6 peaked at day 10 of differentiation, followed by an increase in the expression of the spinal cord-related genes OLIG2 and NKX6-1 (FIG. 4c, d; interaction P=0.005, gene P<0.0001, time P=0.01). To explore cell diversity in hSpS, we performed single-cell transcriptional profiling using stochastic barcoding, as we have previously done in brain region-specific spheroids. We examined day 45 hSpS that were differentiated in the presence or absence of DAPT, a Notch modulator known to promote cell cycle exit in motor neuron progenitors22 (FIG. 10a) (n=7,888 cells; BD Rhapsody system; FIG. 4e).

Analysis of cells using the t-distributed stochastic neighbor embedding (tSNE) approach showed that the expression of the neuronal marker STMN2 was restricted to cells on the left side of tSNE space while cells on the right side expressed the progenitor marker VIM and genes associated with mitotically active cells (FIG. 9a). Further examination identified several subdomains, including clusters of actively dividing progenitor cells expressing TOP2A and progenitors expressing SOX2, PAX6 and NEUROG1 (clusters #1-3; FIG. 9b, c); several groups of GABAergic, glycinergic and glutamatergic interneurons (FIG. 4f; #4, 5, 7, 8, 9), including cells expressing the V2b marker genes GATA2 and GATA3 (#8) or the interneuron markers SST and PENK(#9); a mixed neuronal cluster (#6); and a motor neuron cluster expressing the transcription factors ISL1, PHOX2B, and LHX3 and the choline transporter gene SLC5A7 (also known as CHT1; cluster #10) (FIG. 4f). The diversity of cell types in hSpS reflects some of the cell diversity described in the spinal cord$_2$ (FIG. 10b).

When differentiated in the presence of DAPT, although overall similar to the unexposed condition (hSpS$_{(-)DAPT}$; R$_2$=0.85, P<0.0001), hSpS contained an approximately three-fold increase in the proportion of motor neurons (FIG. 9d-f). For this reason, the hSpS condition that included DAPT exposure was used for the rest of the experiments.

To further validate the presence of these neuronal identities and assess differentiation reliability in several hiPS cell lines, we performed RT-qPCR for a set of domain-specific markers, including glial lineage-related genes, and then confirmed expression by immunocytochemistry in cryosections (FIG. 10c-h). Lastly, we confirmed the presence of cholinergic motor neurons by immunocytochemistry for the enzyme that catalyzes the biosynthesis of the neurotransmitter acetylcholine (CHAT), the neurofilament SMI-32 and the transcription factor HB9 (FIG. 4g, h), and by electrophysiological recordings using an Hb9::GFP reporter (FIG. 4i, j).

Figure 11A:
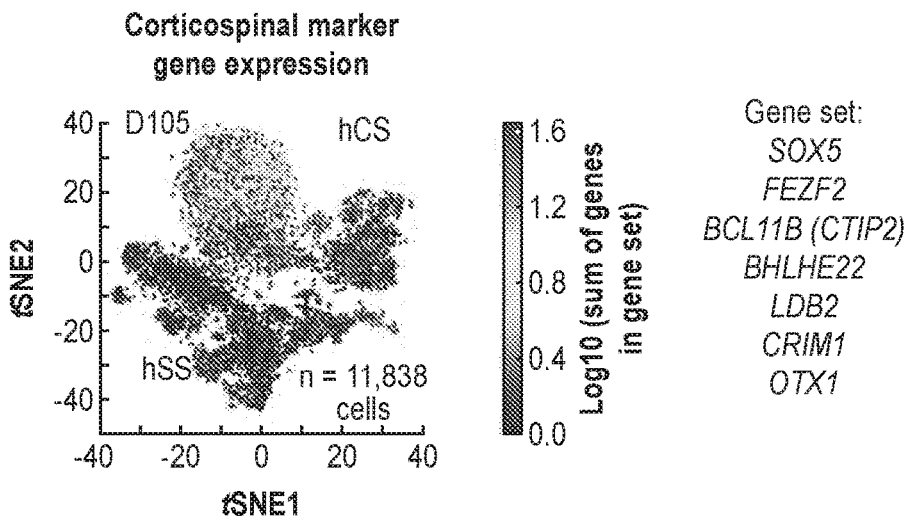
FIG. 11. Characterization of hCS cortico-spinal neurons a, t SNE visualization of single cell gene expression of hCS and hSS (human subpallial spheroids) at day 105 of differentiation (n=11,838 cells; $BD_{TM}$ Resolve system, from Birey et al.[11]) showing the distribution of expression of a set of genes associated with corticospinal neuronal identity (SOX5, FEZF2, BCL11B or CTIP2, BHLHE22, LDB2, CRIM1 and OTX1). b, Gene expression analysis of cortico-spinal-related genes in hCS over time (n=4-6 hiPS cell lines; one-way ANOVA interaction: P=0.001 for FEZF2, P<0.0001 for BCL11B, P=0.5 for OTX1, P<0.0001 for LDB2; Kruskal-Wallis test interaction: P=0.002 for SOX5, P=0.006 for CR/M1). c, d, Immunocytochemistry in hCS cryo-sections at day 130 of in vitro differentiation showing expression of cortico-spinal markers CTIP2 and OTX1 (c). Antibodies were validated in slices of human cortical tissue at post-conception week 17 (PCW17, d). Data represent mean±s.e.m. Scale bars, 50 μm (c), 500 μm (d).
Figure 11B:
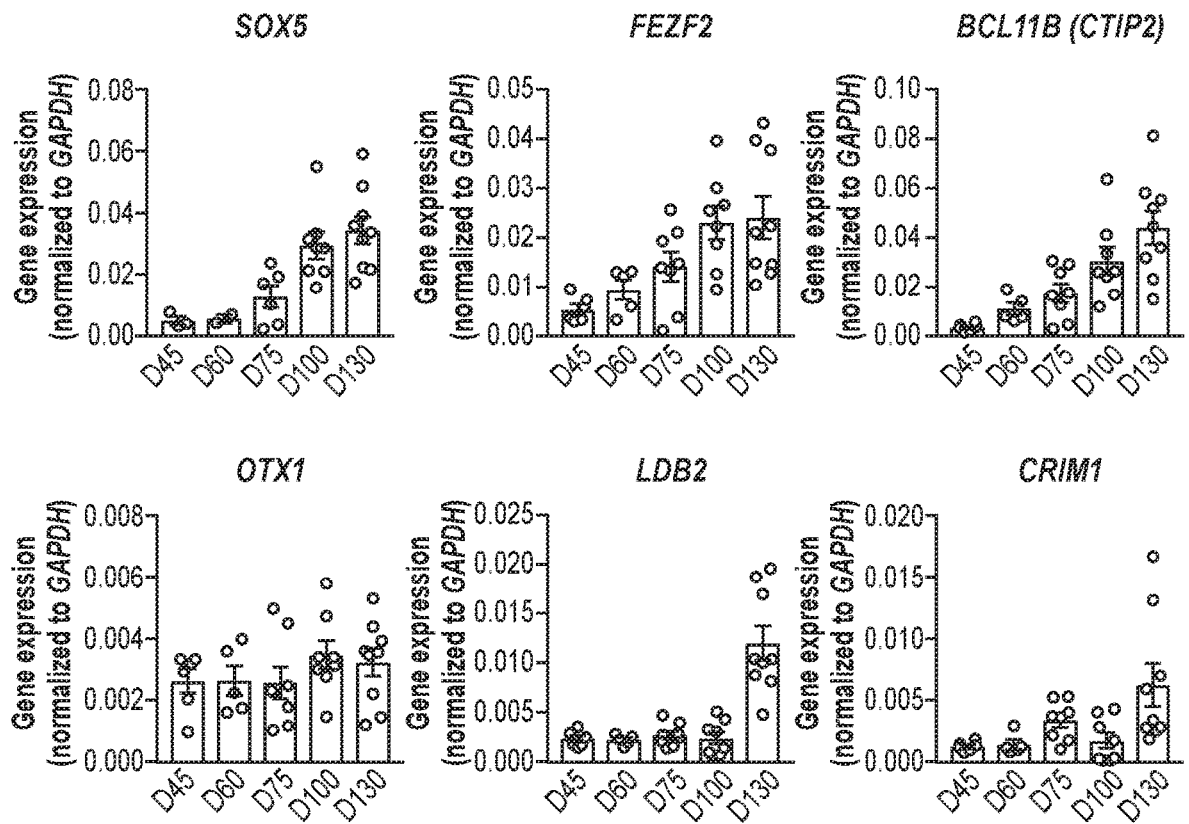
Figure 11C:
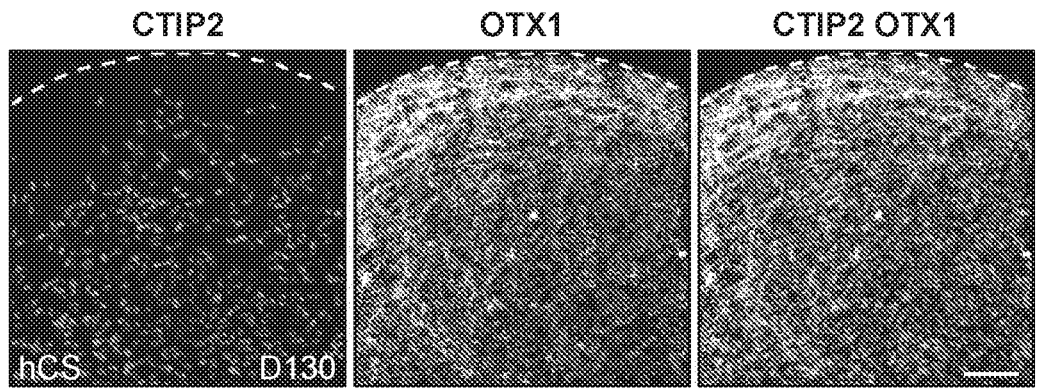
Figure 11D:
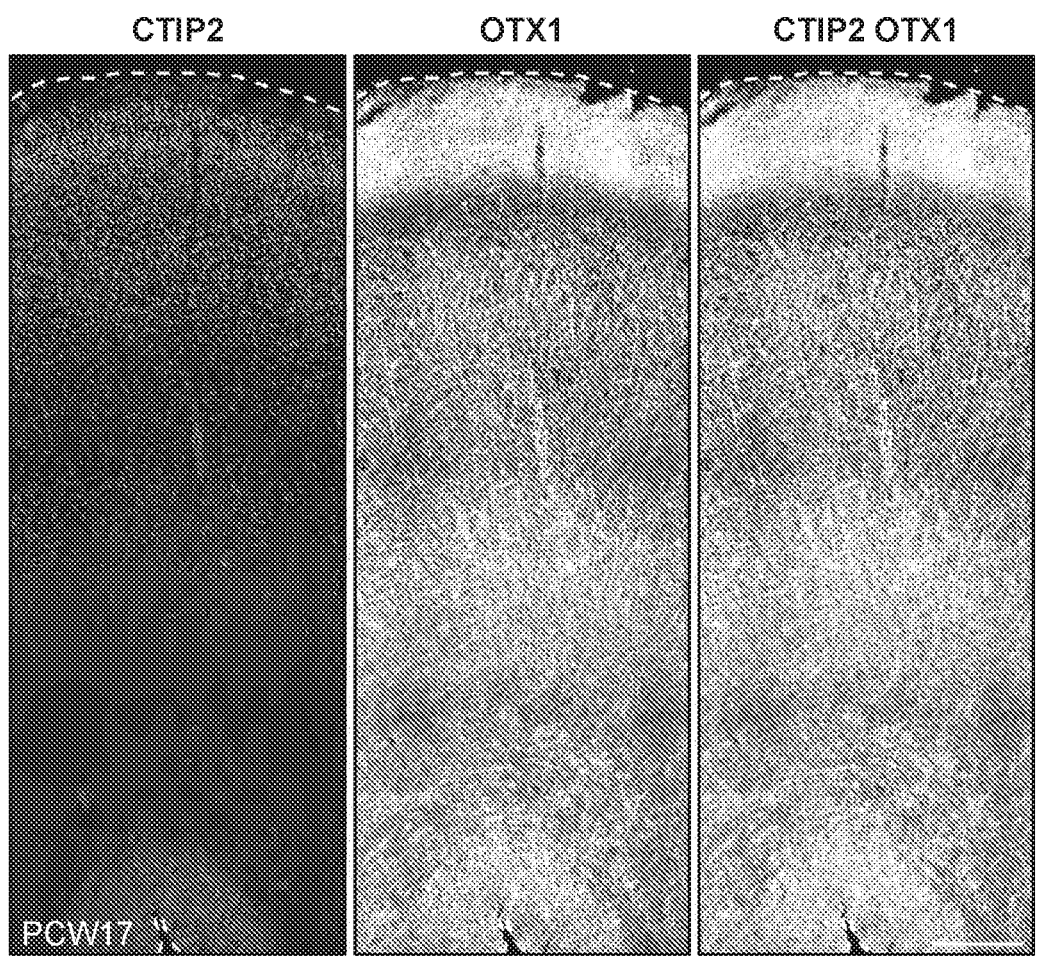

We previously described the reliable generation of 3D neural spheroids resembling the cerebral cortex (human cortical spheroids, hCS), which contain deep and superficial glutamatergic neurons. We verified expression of corticospinal-related markers in hCS, including FEZF2, BCL11B (also known as CTIP2) and SOX5, using single cell profiling of hCS and found a population of cells co-expressing these genes in the glutamatergic neuron cluster but not in a subpallial-derived GABAergic cluster or in other ventral forebrain populations (FIG. 11a). Moreover, we confirmed the expression of this set of corticospinal-related genes by RT-qPCR from day 45 to day 130 in vitro (FIG. 11b), as well as by immunocytochemistry in cryo-sections with antibodies that we validated in slices of human cortical tissue at post-conception week 17 (PCW17, FIG. 11c, d).

Figure 4K:
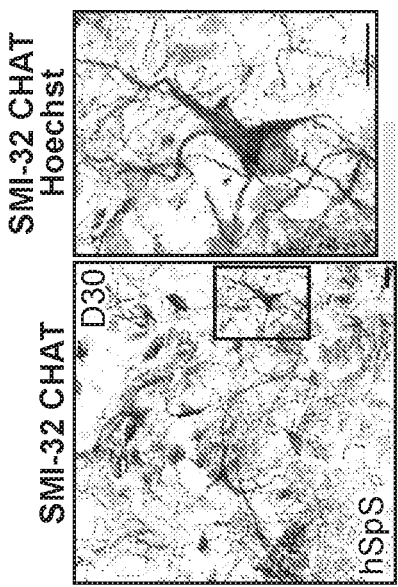
Figure 4I:
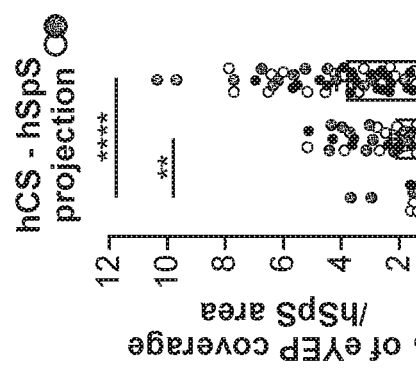
Figure 4J:
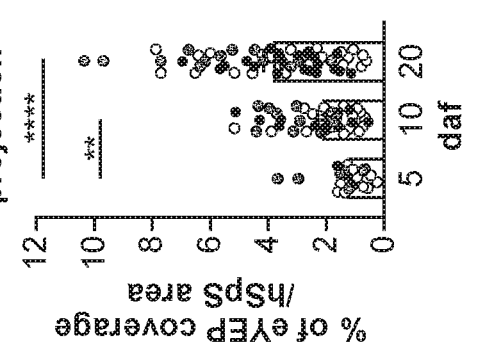
Figure 4L:
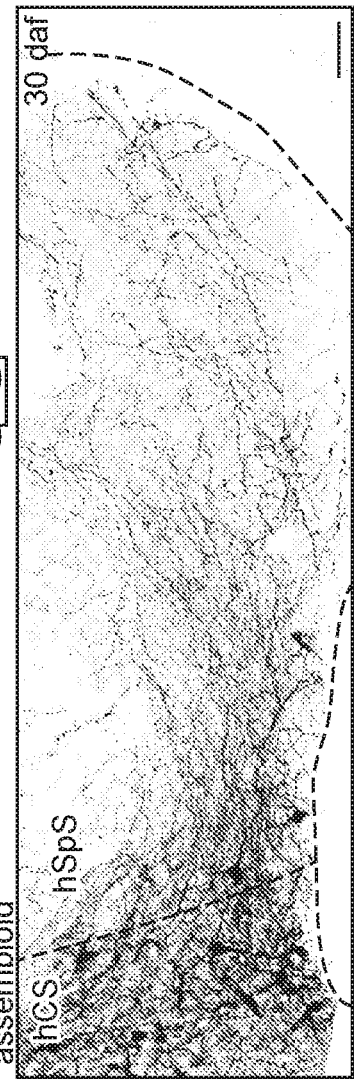
Figure 4M:
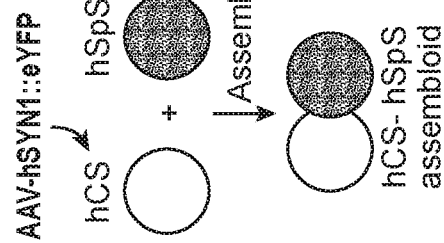

To generate cortico-spinal assembloids, we fused hCS that had been infected with an AAV-hSYN1::eYFP reporter with hSpS (FIG. 4k). Live imaging at 5 days after fusion (daf) showed processes derived from cells in the hCS extending into hSpS. At 30 days after assembly, immunocytochemistry for YFP in cryo-sections showed extensive hCS-derived YFP projections into hSpS (FIG. 4l). Quantification of the eYFP$^+$-covered area in hSpS in intact hCS-hSpS assembloids showed a progressive increase of eYFP over time (5 daf versus 10 daf P=0.009; 5 daf versus 20 daf P<0.0001; FIG. 4m and Fig. a; and FIG. 12b for examples of hCS-hSpS assembloids 20 daf), and this was not observed to the same extent in hCS-hCS assembloids (5 daf versus 10 daf P>0.9; 5 daf versus 20 daf P=0.06; FIG. 12c, d). At the same time, we did not observe hSpS-derived cells moving into hCS in hCS-hSpS assembloids where hSpS had been infected with Hb9::mCherry (FIG. 12e).

To further characterize hCS projections into hSpS, we used a retrograde rabies tracing approach (FIG. 2a). We separately infected hSpS with a AG-rabies virus carrying Cre-eGFP recombinase and with an AAV carrying the rabies glycoprotein (G) required for the transsynaptic spread within the nervous system28,29, and hCS with an AAV encoding mCherry under a double-floxed inverse orf (DIO-mCherry). After 6-7 days of infection, hCS and hSpS were assembled and expression of GFP and mCherry was examined at 31 daf. We predicted infected neurons in hSpS would express GFP from the rabies-Cre virus, and hCS neurons would co-express GFP and mCherry following rabies-Cre retrograde transport and Flip exchange of the mCherry transgene. We observed extensive expression of GFP in hSpS and cells co-expressing GFP and mCherry in the cortical side of the assembloid (FIG. 5b; FIG. 12f). We found that ~95% of the GFP+/mCherry+cells in hCS coexpressed the neuronal marker MAP2 and fewer than 4% expressed the glial lineage related marker GFAP (FIG. 5c, d; FIG. 12g).

Corticofugal projection neurons, which include corticospinal projecting cells, express the marker CTIP2 (also known as BCL11B) and are mainly located in deep layers of the cerebral cortex, while neurons located in superficial layers express BRN2 (also known as POU3F2) project through the corpus callosum to the contra-lateral cortex. To verify the type of GFP+/mCherry+cells in hCShSpS assembloids, we quantified the proportion of these that co-expressed either CTIP2 or BRN2. We found that almost 60% of all GFP+/mCherry+cells co-expressed the corticofugal marker CTIP2 and only ~12% co-expressed BRN2 (FIG. 5e-g), although the relative proportions of these cell types were not different in hCS at this in vitro stage (FIG. 5h). The functional output of the cortico-spinal circuit is muscle contraction through motor neuron activity.

Figure 13A:
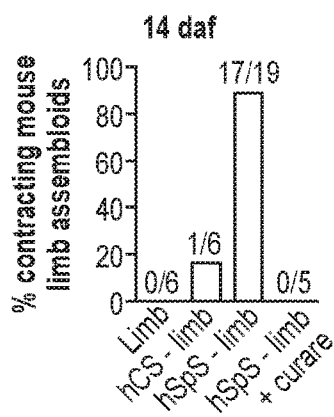
FIG. 13. Functional characterization of hSpS a, Quantification of the proportion of contracting limb, hCS-limb or hSpS-limb assembloids 14 days after fusion (daf). Contraction of hSpS-limb assembloids was completely blocked by curare (100 μM; n=3 hiPS cell lines; $X^2$ test, P=0.02). b, c, Characterization of human skeletal myoblast (hSkM) differentiation. hSkM differentiate upon removal of FBS from the culture medium (b). immunocytochemistry images for desmin (DES), titin (TTN) and the heavy myosin chain (MyHC) show differentiation of myoblasts over time (c). d, Distribution and mean number of Hoechst. nuclei in desmin cells at day 0 and day 15 of hSkM differentiation. Data represent mean±s.e.m. (n=1,031 desmin+cells at day 0, and n=190 desmin+cells at day 15; data was collected in each case from 5 fields within a culture well in 2 hSkM differentiation replicates; Mann-Whitney test **P<0.0001). e, Representative calcium imaging for hSkM and hSpS-hSkM. Images show average (avg) intensity projections of Cal-590 AM in a field (average intensity projections were used to delineate cells for quantification). Traces show examples of active and inactive hSkM cells in either hSkM alone or hSpS-hSkM cultures. AF/F indicates the fluorescence intensity over baseline fluorescence. Arrows show cells analyzed. f, Scheme detailing hSkM analyzed for calcium imaging experiment. Spontaneous calcium activity was recorded in 6-9 fields per culture well. Of these fields some were within 1 mm of the spheroid, and some were further than 1 mm from the spheroid. g, Quantification of spontaneous calcium imaging activity in hSkM over a period of 2 minutes. Fields were separated according to their distance from the spheroid (hCS or hSpS). Data represent mean±s.e.m. (n=2 hiPS cell lines; one-way ANOVA P=<0.0001, with Dunnett's multiple comparison test **P<0.0001). Scale bars, 200 μm (c, e), 400 μm (b).

To probe the ability of hSpS to mediate muscle contraction, we dissected mouse limb buds at embryonic day 11.5 (E11.5), which precedes spinal cord innervation, and assembled them with hSpS derived from a TUBA1B-mEGFP hiPS cell line. We observed extensive projections from the hSpS into the limb bud upon assembly (FIG. 6a). Moreover, limb buds displayed spontaneous contractions when assembled with hSpS, but not when kept in isolation or when assembled with hCS ($X^2$ test, P=0.02; FIG. 6b). Activity in hSpS-limb assembloids persisted for at least two weeks in vitro and was completely blocked by addition of the acetylcholine receptor antagonist curare (100 μM; $X^2$ test, P=0.02, FIG. 13a).

Figure 13B:
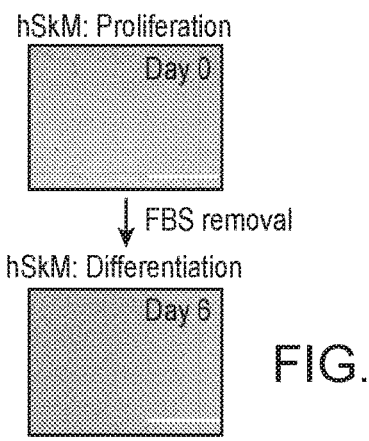
Figure 13C:
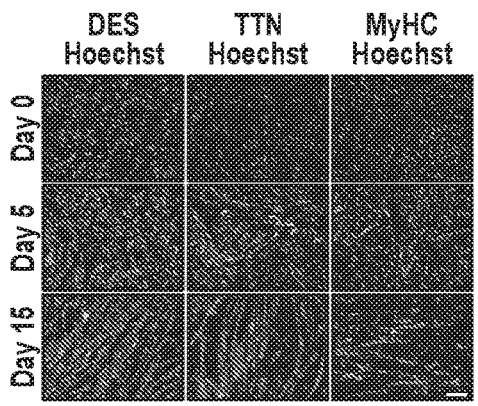
Figure 13D:
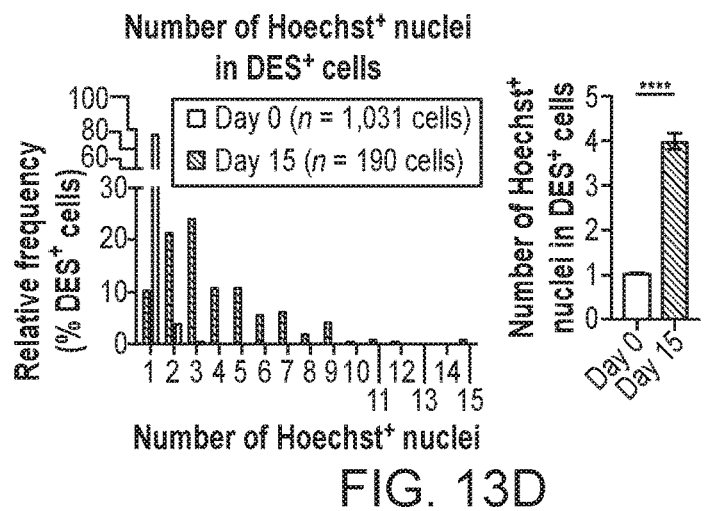

To confirm the presence of neuromuscular junctions (NMJ) in hSpS-limb assembloids, we used immunocytochemistry to identify human motor neurons co-expressing SMI-32 and the cholinergic related marker CHAT that projected into the limb explant (FIG. 6c). These neurons sometimes ended in regions that were labeled with bungarotoxin (BTX), a peptide toxin that binds with high affinity to nicotinic acetylcholine receptors at NMJs (FIG. 6d). Next, we probed the ability of hSpS to modulate the activity of human muscle cells. To achieve this, we used human skeletal myoblasts (hSkM) derived from adult muscle biopsies. These cells proliferate in culture when grown in fetal bovine serum (FBS) but can differentiate into myotubes upon removal of FBS (FIG. 13b). Differentiated myotubes express markers of mature skeletal muscle, such as desmin (DES), titin (TTN) and the heavy chain myosin (MyHC), and become multinucleated (day 0 versus day 15 of differentiation P<0.0001; FIG. 13c, d).

Figure 6H:
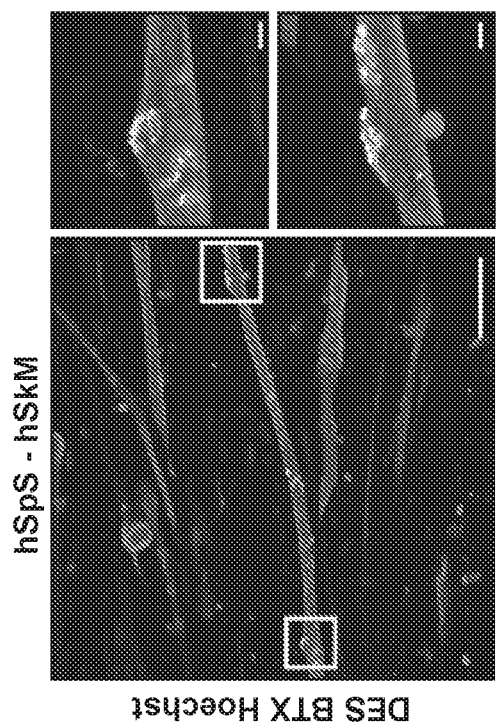
FIG. 6. hSpS control of muscle activity a, Image of intact assembloid showing hSpS derived from TUBA1B-mEGFP projecting into mouse limb. b, Quantification of the proportion of contracting limb, hCS-limb or hSpS-limb assembloids 7 days after fusion (daf; n=3 hiPS cell lines; $X^2$ test, P=0.02). c, d, Representative immunocytochemistry image of hSpS-limb assembloids showing cholinergic neurons and BTX binding at 11 days after fusion (daf). e, Scheme showing the co-culture of 2D human skeletal myoblasts (hSkM) and spheroids (hCS or hSpS). f, Immunocytochemistry of 2D hSkM 7 days after co-culture with hCS or hSpS. g, Quantification of spontaneous calcium activity in hSkM (Cal-590 AM) in either hSkM alone or after co-culture with hCS, hSpS or hSpS+curare (100 μM). Active generated at least 1 calcium event over a 2-minute period. Graph on the left shows % of active hSkM per field recorded (n=2 hiPS cell lines; Kruskal-Wallis test P<0.0001, with Dunn's multiple comparison test ****P<0.0001). Graph on the right shows % of active hSkM per co-culture experiment (in this case all fields imaged in one experiment are combined; n=2 hiPS cell lines; Kruskal-Wallis test P=0.02, with Dunn's multiple comparison test *P=0.01). h, Representative immunocytochemistry image showing BTX binding in hSkM that had been co-cultured with hSpS. Data represent mean±s.e.m. Scale bars, 10 μm (insets in d, h), 20 μm (c, d), 100 μm (a, h), 200 μm (f).
Figure 6G:
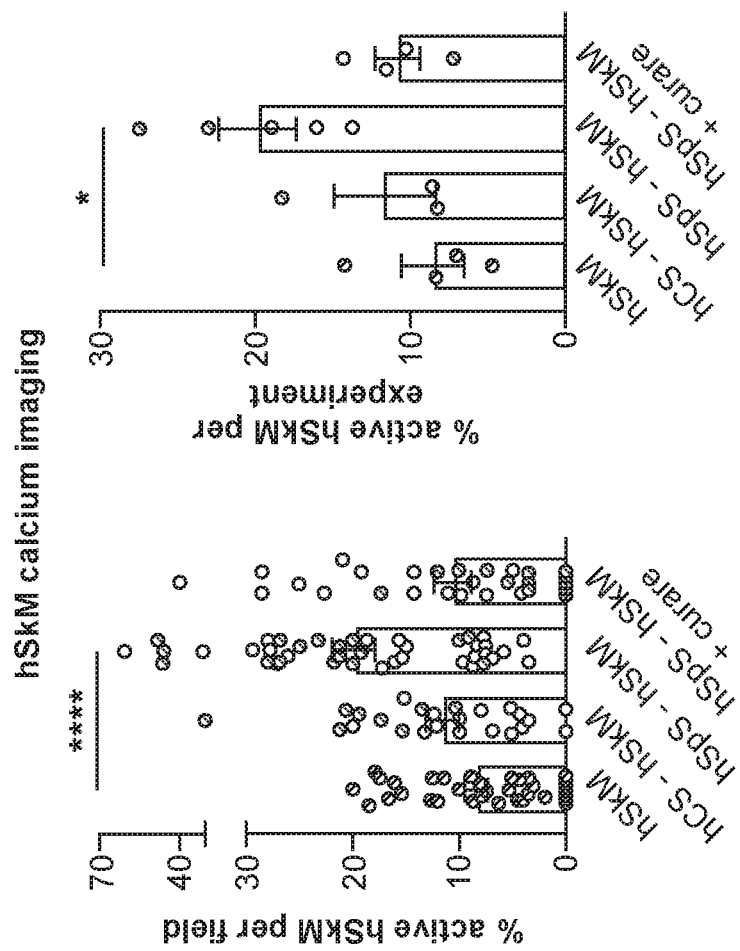
Figure 13E:
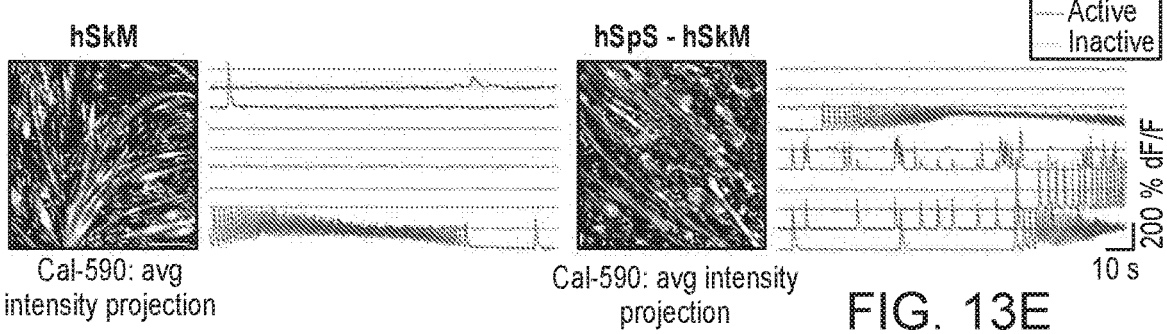
Figure 13F:
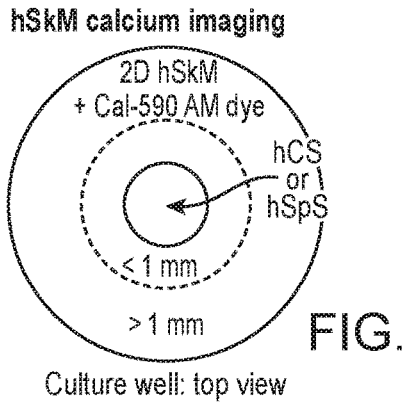
Figure 13G:
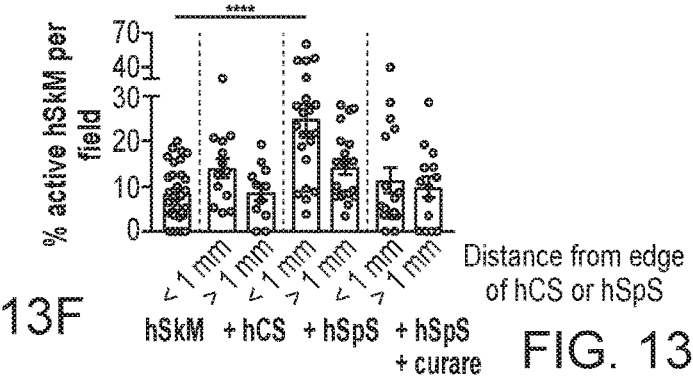

We placed hSpS on top of hSkM grown in adherent cultures (FIG. 6e), and within a week hSpS projected out to cover muscle cells (FIG. 6f). Using live imaging with the calcium indicator Cal-590, we found that the proportion of active hSkM doubled in hSpS-hSkM in comparison to hSkM in isolation or hCShSkM, and this effect was blocked by curare (hSpS-hSkM versus hSkM P=0.01; FIG. 6g; FIG. 13e). Further analyses revealed that it was mainly hSkM within 1 mm of hSpS whose activity increased following co-culture (hSkM versus hSpS-hSkM <1 mm, P<0.0001; FIG. 13f, g), and immunocytochemistry of hSkM after co-culture with hSpS revealed BTX binding (FIG. 6h).

Lastly, to assemble a cortico-spinal-muscle unit, we fused intact hCS to hSpS and to 3D hSkM (FIG. 7a). To achieve this, we first generated 3D hSkM by combining dissociated proliferative hSkM with Geltrex™ in a silicone well. After differentiation, the 3D hSkM formed a spheroid (FIG. 14a). We then placed an hCS, an hSpS and a 3D hSkM in close proximity on top of a transwell insert in a 6-well cell culture plate (FIG. 8b, c; FIG. 14a). Using spheroids derived from the TUBA1B-mEGFP hiPS cell line, we noticed that, by 12 daf, hSpS sent out abundant projections to the 3D hSkM (FIG. 14b). Moreover, 3D hSkM displayed spontaneous contractions before and after assembly. To quantify these contractions, we looked at displacement of pixels over time in imaging fields (1.8 mm by 1.8 mm in size, subdivided into 16 subfields) (FIG. 14c).

Figures 14D, 14E:
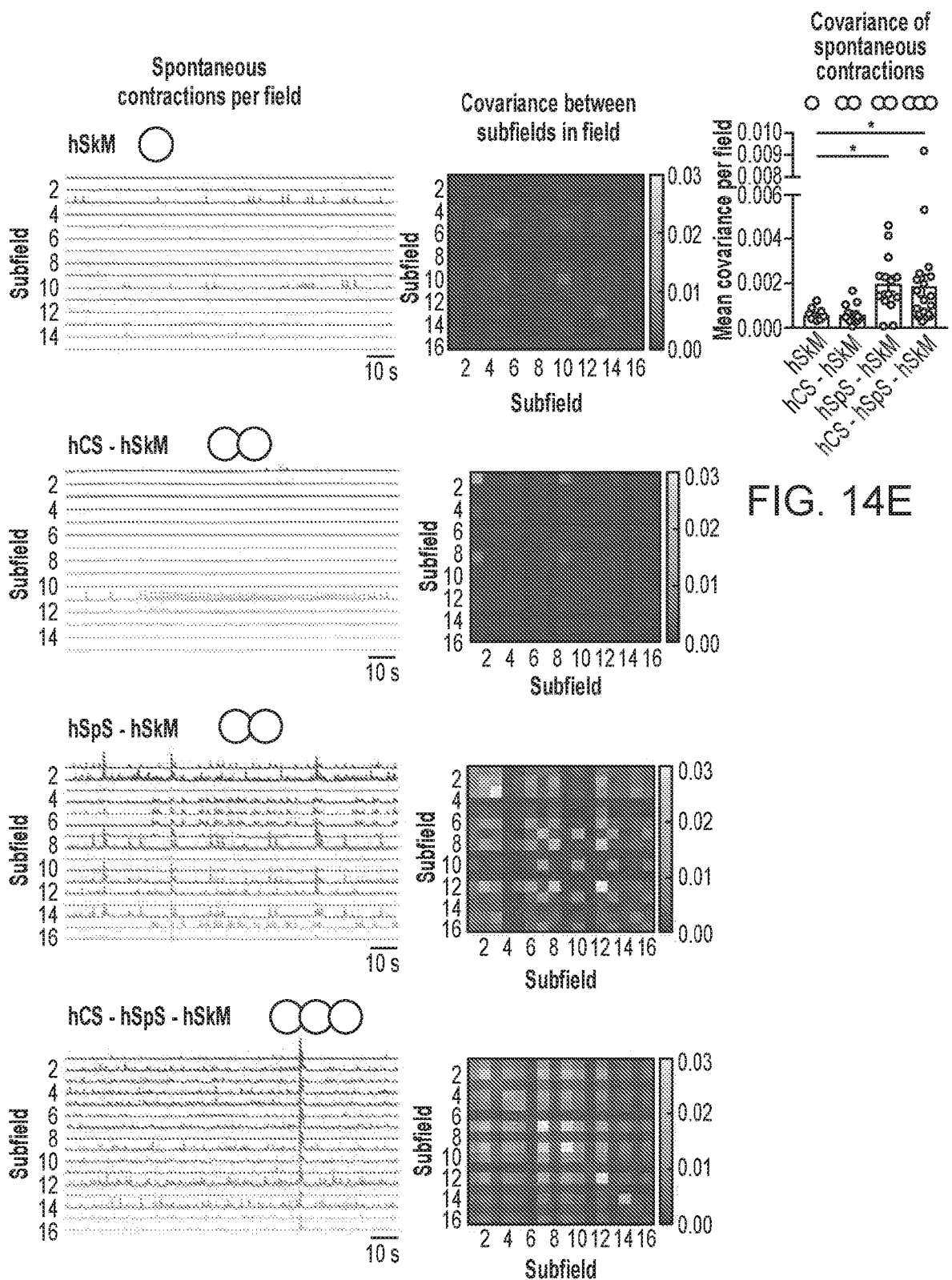
FIG. 14. Spontaneous contractions in hCS-hSpS-hSkM assembloids a, Images showing the generation of 3D hSkM and the assembly with hCS and hSpS. (1.) Dissociated hSkM are resuspended in Geltrex™ and placed in silicone wells, (2.) Next day silicone wells are placed in ultra-low attachment plates in hSkM growth medium, After 15 7-10 days in growth medium, hSkM growth medium is switched to differentiation medium, and after ~2 weeks (wk) in culture 3D hSkM will be formed. (4.) After 2-3 weeks, 3D hSkM can be co-cultured with hSpS and/or hCS. For this, 3D hSkM and spheroids are placed on insert wells with 2 ml of medium per well. b, Representative images of 3D hSkM that has been assembled with hCS or hSpS derived from a TUBA1B-mEGFP hiPS cell line showing projection of hSpS cells into 3D hSkM. c, Imaging fields (1.8 mm×1.8 mm in size) are divided into 16 subfields for analysis. Only subfields containing hSkM are analyzed. d, e, Representative spontaneous contraction traces in subfields of hSkM, hCS-hSkM, hSpS-hSkM or hCS-hSpS-hSkM assembloids (d, left). The correlation of displacements between subfields in a field is quantified using covariance analysis (d, right, e). Data represent mean±s.e.m. (n=10 fields from 5 assembloids for hSkM, n=12 fields from 6 assembloids for hCS-hSkM, n=14 fields from 7 assembloids for hSpS-hSkM, n=19 fields from 11 assembloids for hCS-hSpS-hSkM; Kruskal-Wallis test P=0.001, with Dunn's multiple comparison test: *P=0.01 for hSpS-hSkM versus hSkM, *P=0.03 for hCS-hSpShSkM versus hSkM). Scale bars, 200 µm (b, c).
Figure 15A:
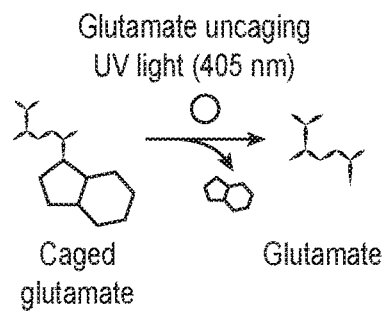
FIG. 15. Glutamate uncaging in hSpS-hSkM and hCS-hSpS-hSkM assembloids a, Scheme illustrating the glutamate uncaging approach. Caged glutamate is added to the culture medium, and uncaged upon UV light stimulation (405 nm). b-d, Glutamate uncaging of hSpS in hSpS-hSkM assembloid. Displacement normalized to baseline over time is shown for 3 subfields in the presence (c) or absence (d) of caged glutamate in the medium. e, f, Glutamate uncaging of hSpS in hCS-hSpS-hSkM assembloid. Displacement normalized to baseline over time is shown for 4 subfields in the presence of caged glutamate in the medium. g, h, Glutamate uncaging of hCS in hCS-hSpS-hSkM assembloid. Displacement normalized to baseline over time is shown for 3 subfields in the absence of caged glutamate in the medium (see FIG. 4h, i for glutamate uncaging in this field in the presence of caged glutamate). i, j, Glutamate uncaging of hCS in hCS-hSkM assembloid. Displacement normalized to baseline over time is shown for 4 subfields in the presence of caged glutamate in the medium. Scale bars, 200 µm (c, f, h, j).

We found that hSpS-hSkM and hCS-hSpS-hSkM assembloids displayed ~5× more spontaneous contractions than hSkM alone or hCS-hSkM assembloids (P=0.01 for hSpS-hSkM versus hSkM; P=0.0002 for hCS-hSpS-hSkM versus hSkM; FIG. 7d). Moreover, we found that spontaneous activity in hSpS-hSkM and hCS-hSpS-hSkM assembloids was more coordinated across fields as assessed by analysis of the covariance between subfields in an imaging field (P=0.01 for hSpS-hSkM versus hSkM, P=0.03 for hCS-hSpS-hSkM versus hSkM; FIG. 14d, e). We next wanted to manipulate contraction of muscle cells by selectively stimulating parts of an assembloid. We used 405 nm photostimulation while applying MNI-caged glutamate to the culture medium to rapidly and locally release (or uncage) glutamate (FIG. 15a).

Figure 15B:
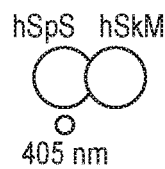
Figures 15C, 15D:
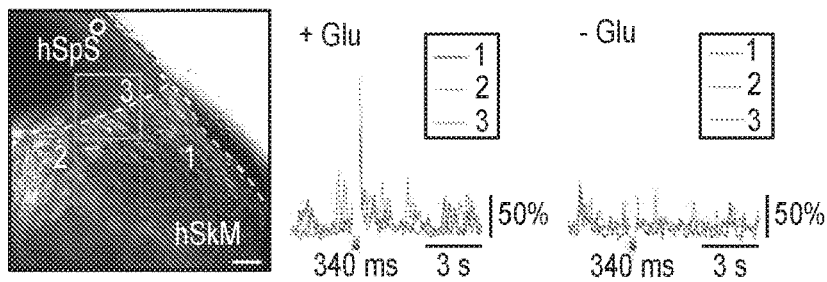
Figure 15E:
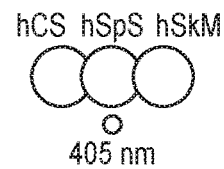
Figure 15F:
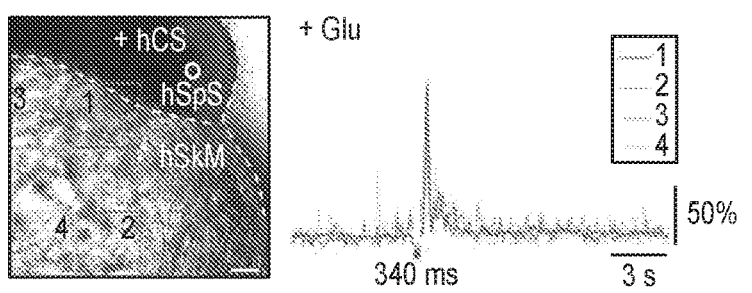
Figure 15G:
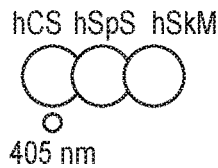
Figure 15H:
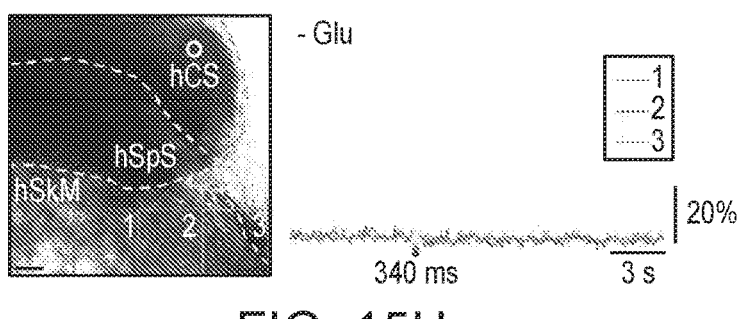
Figure 15I:
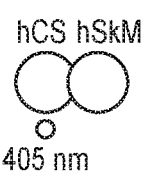
Figure 15J:
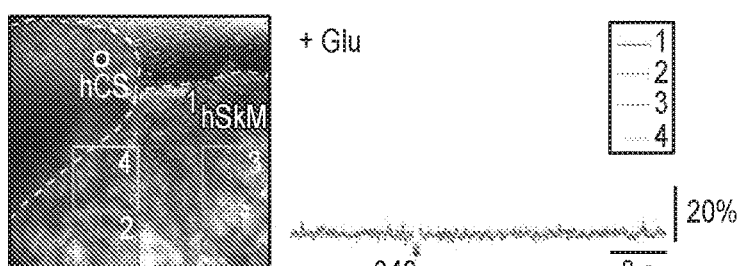

Photostimulation of hSpS in hSpS-hSkM assembloids resulted in hSkM contraction in the presence, but not in the absence, of MNI-caged glutamate (FIG. 15b-d). Similarly, stimulation of hSpS in hCS-hSpS-hSkM assembloids was coupled with hSkM contraction (FIG. 15e, f). Importantly, uncaging in hCS in hCS-hSpS-hSkM 7 assembloids resulted in robust muscle contraction (P=0.002; FIG. 7e-g), suggesting functional assembly of a cortico-spinal-muscle functional unit. This contraction was blocked by treatment with 100 μm curare (FIG. 7f) and was not related to UV exposure since photostimulation in the absence of MNI-caged glutamate did not result in contraction (FIG. 15g, h). Moreover, glutamate uncaging of hCS in hCS assembled with hSkM did not elicit a response (FIG. 15i, j), showing that muscle contraction upon cortical stimulation is dependent on the presence of the hSpS.

Figure 16A:
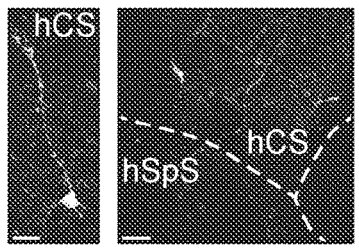
FIG. 16. Optogenetic stimulation in hCS-hSpS-hSkM assembloids a, Image showing ChrimsonR-tdT+cells in hCS infected with AAV-hSYN1-ChrimsonR-tdT. b, Histogram illustrating the success rate of optogenetic stimulation (out of 5 consecutive pulses for each assembloids; n=15 trials of 5 pulses in 7 assembloids). 16 c, d, Representative example of optogenetic stimulation in hCS-hSpS-hSkM assembloids (five 68 ms pulses). hCS were infected with AAV-hSYN1-ChrimsonR-tdT (Chrim). Traces of displacement in the whole field in c are shown normalized to the pre-stimulation baseline. Two trials for the same assembloid are shown. Addition of NBQX (50 µM) and APV (50 µM) abolished muscle contraction upon light-induced hCS stimulation (d). e, f, Optogenetic stimulation in hCS-hSkM assembloid (five 68 ms pulses). hCS were infected with AAV-hSYN1-ChrimsonR-tdT. Displacement over time normalized to prestimulation baseline is shown for the whole field in e. Scale bars, 40 µm (a), 200 µm (c, e).
Figure 16B:
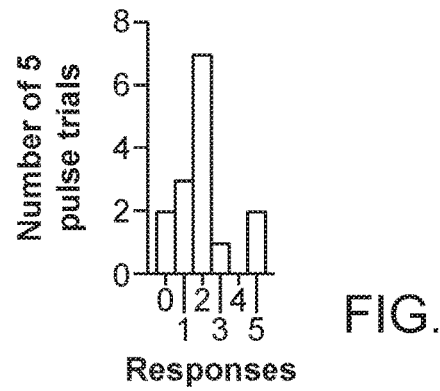
Figure 16C:
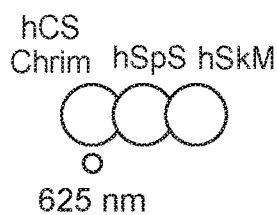
Figure 16D:
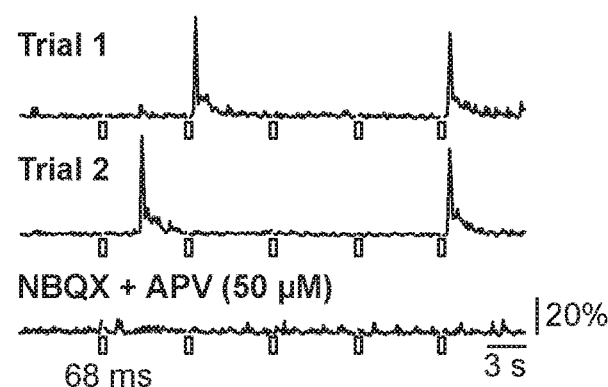
Figure 16E:
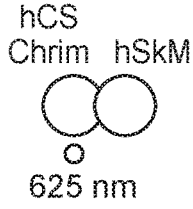
Figure 16F:
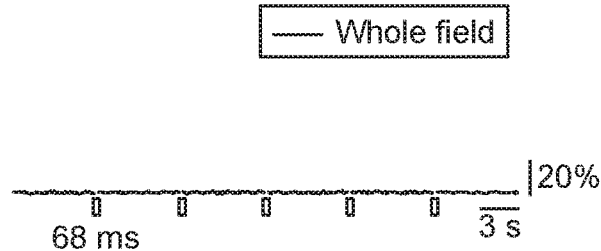

Because both hCS and hSpS can respond to glutamate, it is possible for glutamate molecules to diffuse from hCS to hSpS and stimulate neurons in other parts of the assembloid. Therefore, to validate cortical activation of muscle in hCS-hSpS-hSkM assembloids and achieve broader stimulation we used optogenetics. We used an AAV virus to deliver the light-sensitive opsin Chrimson (Chrim, AAV-hSYN1-ChrimsonR-tdT31) into hCS before assembly (FIG. 16a). To probe connectivity, we then used light stimulation (68 ms at 625 nm, 5 pulses, 100 frames or 68 seconds apart each) at 20-30 days after hCS-hSpS-hSkM assembly. Activation of Chrim-expressing hCS induced global contractions in hSkM in 85.7% of tested assembloids (P=0.01; FIG. 7h-j) and 40% of pulses (FIG. 16b shows the distribution of successful stimulation and FIG. 16c, d shows example where muscle contraction is induced in only 2 of the 5 light pulses), while stimulation of Chrim-expressing hCS in hCS-hSkM did not trigger a response (FIG. 16e, f).

To test whether this response was mediated by glutamatergic transmission, we added the NMDA and AMPA receptor blockers NBQX (50 μM) and APV (50 μM), which completely abolished light induced responses (FIG. 7i-j).

Taken together, these results demonstrate that the assembly of intact 3D human cultures resembling the cerebral cortex, spinal cord and skeletal muscle enables the formation of neural circuits that can be readily manipulated in vitro to model cortical control of muscle contraction. Cell reprograming and the subsequent derivation of human neurons from patients holds great promise for studying brain disorders. However, modeling of complex cell-cell interactions and circuit assembly in vitro remains a challenge. We previously showed the potential of using region-specific spheroids as a modular approach to study human interneuron migration and to identify disease phenotypes. Here we leveraged this approach to generate an intact, three-component cortico-spinal muscle circuit in which cortical neural activation modulates muscle contraction via activation of spinal spheroids. This represents a significant advance beyond prior models in which individual components of motor circuits have been generated in simple 2D co-cultures.

Our platform is also different from a recent method that uses sliced human cortical organoids co-cultured with rodent spinal cord explants. Firstly, we use human-derived components that are assembled in a 3D preparation, and we achieved this reliably using multiple hiPS cells lines. Secondly, we build assembloids from intact, 3D cultures that have been patterned to resemble specific brain regions. This allows greater cell diversity while leveraging the ability of specific neural populations to form circuits. Thirdly, we are showing the generation, from three components, of a human neural circuit that contains at least two synaptic contacts. Moreover, to probe the functionality of this novel 3D human preparation, we implemented rabies virus tracing, glutamate uncaging and optogenetic stimulation of various components of the circuit.

Moving forward, there are a number of applications for this cellular platform that can be used to gain insights into the evolution, development and disorders of the corticospinal-muscle circuit. For instance, primates possess direct monosynaptic cortico-spinal connections that control fine motor movements, and a better understanding of the developmental steps underlying cortico-spinal assembly could bring insights into the unique primate aspects of this circuit. Moreover, patient-derived cells could be used to dissect cell autonomous effects and cell-specific vulnerabilities in the context of amyotrophic lateral sclerosis or spinal muscular atrophy. Co-culture with autologous immune cells may reveal the cellular cross-talk underlying multiple sclerosis and other autoimmune conditions. These applications greatly benefit from further improvements such as advanced maturation, astrogenesis and myelination to study neurodegeneration, traumatic injury and scar formation, or assembly of other cell types, such as dorsal root ganglia neurons to model sensory input and local modulation of spinal circuits. Assembloids of various parts of the central nervous system bring insights into understanding differences in connectivity between neuronal cell types and into identifying therapeutic strategies.

Materials and Methods

Culture of hiPS cells. The hiPS cell lines used in this study were validated using standard methods as previously described. A total of seven hiPS cell lines derived from fibroblasts collected from six healthy subjects were used for experiments. hiPS cell lines TUBA1B-mEGFP and LMNB1-mEGFP were derived by the Allen Institute and obtained from Coriell. Cultures were tested and maintained *mycoplasma* free. hiPS cells were cultured on inactivated mouse embryonic fibroblast feeders (EmbryoMax PMEF) in hiPS cell medium containing DMEM/F12, knockout serum (20%), non-essential amino-acids (1:100, Life Technologies), GlutaMax (1:200, Life Technologies), β-mercaptoethanol (0.1 mM, Sigma-Aldrich), penicillin and streptomycin (1:100, Life Technologies), and supplemented with FGF-2 (10 ng ml-1; R&D Systems). Approval for using these lines was obtained from the Stanford IRB panel and informed consent was obtained from all subjects.

Generation of hCS and hSpS from hiPS cells. The generation of hCS from hiPS cells was performed as previously described. Briefly, hiPS cell colonies were lifted from the plates using dispase (0.35 mg ml-1) and transferred into ultralow-attachment plastic dishes (Corning) in hiPS cell medium supplemented with the two SMAD inhibitors dorsomorphin (5 μM, Sigma-Aldrich) and SB-431542 (10 μM, Tocris). This medium was replaced daily for the first five days. On the sixth day in suspension, neural spheroids were transferred to neural medium containing neurobasal-A (Life Technologies, 10888), B-27 supplement without vitamin A (Life Technologies, 12587), GlutaMax (1:100, Life Technologies), penicillin and streptomycin (1:100, Life Technologies) and supplemented with the growth factors EGF (20 ng ml-1; R&D Systems) and FGF-2 (20 ng ml-1; R&D Systems) until day 24. From day 25 to 42, the neural medium was supplemented with the growth factors BDNF (20 ng ml-1, Peprotech) and NT3 (20 ng ml-1, Peprotech) with medium changes every other day. From day 43 onwards hCS were maintained in neural medium with medium changes every four to six days.

To generate hSpS, hiPS cell medium was supplemented with dual SMAD inhibitors until day 5 and the WNT activator CHIR 99021 (3 μM, Selleckchem) from day 4 to day 18. On day 6, spheroids were transferred to neural medium supplemented with RA (0.1 μM, Sigma-Aldrich), EGF (20 ng ml-1; R&D Systems) and FGF-2 (10 ng ml-1; R&D Systems), with addition of the SHH modulator smoothened agonist (SAG, 0.1 μM, Millipore) from day 11.

From day 7, the medium was changed every other day. On day 19, hSpS were transferred to neural medium supplemented with N-2 supplement (Life Technologies, 17502048), BDNF (20 ng ml-1, Peprotech), IGF-1 (10 ng ml-1, Peprotech), L-Ascorbic Acid (AA; 200 nM, Wako) and cAMP (50 nM, Sigma-Aldrich). For hSpS, the Notch inhibitor DAPT (2.5 µM, STEMCELL technologies) was added on days 19, 21 and 23. From day 43 onwards, the medium was changed every four to five days. A schematic detailing the hSpS recipe is shown in FIG. 10a.

For the combinatorial growth factor matrix, small molecules were added on the same days as described above, and the concentrations for dual SMAD inhibitors, CHIR 99021 and EGF were the same as above. Concentrations tested for RA, FGF-2 and SAG are shown in FIG. 8c. From day 7, the neural medium was changed every other day until day 20, when spheres were collected. No DAPT was added for this experiment.

Generation of hCS-hSpS assembloids. To generate cortico-spinal (hCS-hSpS) assembloids, hCS and hSpS were generated separately, and later assembled by placing them in close proximity with each other in 1.5 ml microcentrifuge tubes for 3 days in an incubator. The neural medium used for assembly was supplemented with BDNF (20 ng ml-1, Peprotech), NT3 (20 ng ml-1, Peprotech), LAscorbic Acid (AA; 200 nM, Wako) and cAMP (50 nM, Sigma-Aldrich). Media was carefully changed on day 2 after assembly, and placed in a 24-well ultralow attachment plate (Corning) using a cut P1000 pipette tip on the third day. Medium was changed every 3-4 days thereafter. Assembly was performed between days (D) 60 and D120 of hCS and between D30 and D50 of hSpS. For hCS-hCS assembloids, one hCS was D60-D75 and the second hCS was D45 (to match the hSpS age).

Culture of hSkM. Human skeletal myoblasts (hSkM) were obtained from Thermo Fisher Scientific (A12555, Lot #1837192) and maintained in an undifferentiated state with Skeletal Muscle Cell Growth Medium (ready to use, Promocell) in 10-cm plates (Primaria Cell Culture Dish, Corning). Medium was changed every 2-3 days, and hSkM were passaged using Trypsin (Trypsin-EDTA, 0.25%, phenol red; Life Technologies) when they reached ~80% confluency. hSkM from passages 1 to 4 were used for experiments. For analysis of hSkM differentiation ability, hSkM were plated on wells of 24-well plates (Corning) that had been coated with Geltrex™ (1:50 diluted in DMEM/F12, 1 hour at 37° C.; Life Technologies, A1413202). 30,000 hSkM were plated on day 0 in Skeletal Muscle Cell Growth Medium. Medium was replaced the day after plating and every other day after that. When hSkM reached ~90% confluency (2-3 days after plating), Skeletal Muscle Cell Growth Medium was replaced with Skeletal Muscle Cell Differentiation Medium (ready to use, Promocell). On days 0, 5 and 15, hSkM were washed with PBS once and fixed for 10 minutes with 4% paraformaldehyde (PFA).

Generation of 3D hSkM. For the generation of 3D hSkM cultures, hSkM were dissociated using Trypsin (Trypsin-EDTA, 0.25%, phenol red; Life Technologies) and resuspended in Geltrex™ (Life Technologies) at a density of 3,000 hSkM per µl. Fifty µl of this viscous cell suspension were aliquoted into silicone wells (80369, Ibidi) located inside 6-well tissue culture plates (Corning), and incubated for 30 minutes at 37° C. to allow Geltrex™ gelling, at which point 4 ml of Skeletal Muscle Cell Growth Medium was added. The next day, silicone wells containing hSkM were placed into 6-well ultralow-attachment plates, and medium was changed every 2-3 days. After 7-10 days, medium was changed to Skeletal Muscle Cell Differentiation Medium to allow for differentiation of hSkM with medium changes every 2-3 days. 3D hSkM were used for assembloid generation 10 to 25 days after the switch to differentiation medium. FIG. 15a shows pictures of the 3D hSkM set-up.

Generation of hSpS-hSkM or hCS-hSpS-hSkM assembloids. To generate neural-muscle assembloids, 3D hSkM that had been in differentiation medium for at least 10 days (see above) were removed from the silicone wells and placed on top of cell culture inserts (0.4 µm pore size; 353090, Corning) that were positioned in 6-well plates containing 2 ml of DMEM/F12 medium supplemented with 1% Non-Essential Amino Acids (NEAA, Life Technologies), 1% Insulin-Transferrin-Selenium (ITS, Life Technologies), 1% penicillin and streptomycin (Life Technologies), L-Ascorbic Acid (AA; 200 nM, Wako) and cAMP (50 nM, Sigma-Aldrich). Next, spheroids (either hSpS or hCS) were placed on the inserts containing 3D hSkM and arranged so that they were in contact with one another and were allowed to interact.

For hCS-hSpS-hSkM assembloids, hSpS-hSkM was assembled first, and hCS was added 1-2 days later. For this combination, sometimes more than one (1-3) hSpS were added. hSpS tend to be smaller in size than hCS, and adding more than one hSpS avoids hCS being in direct contact with hSkM. Only one assembloid was maintained per insert, and half medium changes were performed every other day. FIG. 8b shows a schematic detailing this set-up, and FIG. 15a shows pictures of the generation of 3D hSkM and the insert set-up. Imaging of 3D hSkM spontaneous contractions was performed under environmentally controlled conditions (37° C., 5% CO2) using a 5× objective in a confocal microscope (Leica SP8). Assembloids, still in transwells, were incubated in the environmentally controlled chamber for 20-30 minutes before imaging, and they were imaged for 2 minutes at a frame rate of 14.7 frames/sec. 1-2 fields were imaged per assembloid.

Human fetal tissue. Human tissue was obtained under a protocol approved by the Research Compliance Office at Stanford University. PCW17 forebrain tissue was delivered overnight on ice and immediately processed after arrival. Cortical tissue was fixed overnight in 4% PFA, washed three times with PBS and embedded as described below.

Co-culture of mouse limb and spheroids. For mouse co-culture experiments, timed-pregnant females were sacrificed at E11.5, embryos were collected, and limb buds dissected (both forelimbs and hindlimbs were used for this experiment). Limbs and spheroids (at D25) were then assembled together by placing them in close proximity in a 1.5 ml microcentrifuge tube for 3 days in an incubator. One limb and one spheroid were placed per tube. On day 2 medium was carefully changed. Neural medium supplemented with N-2 supplement (Life Technologies, 17502048) was used. After assembly, mouse-spheroid cultures were placed in 24-well ultralow-attachment plates (Corning), and medium was changed every other day. For contraction quantification, assembloids were visualized using brightfield illumination in an EVOS FL Cell Imaging System (Life Technologies), and they were deemed to be contracting if they moved within a time-window of 30 seconds. Approval for mouse experiments was obtained from the Stanford University's Administrative Panel on Laboratory Animal Care (APLAC).

Viral labeling and rabies-ΔG tracing. Viral labeling of neural spheroids was performed as previously described19. In brief, spheroids were placed in a 1.5 ml microcentrifuge tube containing 250 µl neural medium with the desired virus and incubated overnight. Fresh medium was added the following day, and spheroids were transferred to ultralow-attachment plates (Corning) the next day. The viruses used for this study are: AAV-DJ1-hSYN1::eYFP, lenti-Hb9::GFP or lenti-Hb9::mCherry42, rabies-ΔG-Cre-eGFP, AAV-DJ1-EF1a-CVS-G-WPRE-pGHpA (Addgene, Plasmid #67528) 43, AAV-DJ1-DIO-mCherry and AAV1-hSYN1-ChrimsonR-tdT (Addgene, #59171-AAV1). Lentivirus was generated in-house by transfecting HEK 293T cells with Lipofectamine 2000 (Thermo Fisher Scientific) and concentrating the supernatant with Lenti-X concentrator (Clontech) 72 h later. AAVs were generated at the Stanford Gene Vector and Virus Core at Stanford University School of Medicine or acquired from Addgene. Rabies-ΔG viruses were obtained from the Salk institute Viral Vector Core. For viral tracing experiments with rabies-ΔG, ~D80 hCS were labeled with AAV-DJ1-DIO-mCherry and -D40-50 hSpS separately labeled with both rabies-ΔG-Cre-eGFP and AAV-DJ1-EF1a-CVS-G-WPRE-pGHpA. Six to seven days after viral infection, hCS and hSpS were thoroughly washed with neural medium, assembled, and maintained in culture with media changes every 3-4 days. After 31 days of fusion, assembloids were fixed with 4% paraformaldehyde and processed for immunocytochemistry as described below.

Projection imaging in intact hCS-hSpS assembloids. The projection of hCS-derived AAV-DJ1-hSYN1::eYFP into hSpS was imaged under environmentally controlled conditions (37° C., 5% CO2) in intact, assembled hCS-hSpS using a confocal microscope with a motorized stage (Leica SP8). Assembloids were transferred to a glass-bottom 96-well plate (Corning) with 200 µl of neural medium, and incubated in the environmentally controlled chamber for 20-30 minutes before imaging. Images were taken using a 10× objective to capture the entire hSpS side at a depth of 50-150 µm. For longterm live imaging of hCS-derived AAV-DJ1-hSYN1::eYFP, the same set-up was used, and hCS-hSpS were imaged for 8-12 hours at a rate of 10 min per frame.

hSkM calcium imaging. For calcium imaging co-culture experiments, hSkM were plated on 24-well plates as described above and differentiated with Skeletal Muscle Cell Differentiation Medium. After 6-7 days of exposure to differentiation medium, hSkM were co-cultured with hSpS or hCS. Skeletal Muscle Cell Differentiation Medium was replaced with DMEM/F12 supplemented with 1% Non-Essential Amino Acids (NEAA, Life Technologies), 1% Insulin-Transferrin-Selenium (ITS, Life Technologies), 1% penicillin and streptomycin (Life Technologies), LAscorbic Acid (AA; 200 nM, Wako) and cAMP (50 nM, Sigma-Aldrich). hSpS or hCS were placed in the middle of the 24-well plate, taking care not to disrupt the hSkM. One hSpS or hCS were placed per well. hSkM-spheroid co-cultures were left undisturbed for two days, and half medium was carefully replaced every other day thereafter. Calcium imaging was performed after 6-7 days of co-culture. Cultures were incubated with Cal-590 AM (10 µM, AAT Bioquest) and PowerLoad (1:100, Invitrogen) for 30 minutes at 37° C., washed once for 10 minutes with full medium and then imaged. A Leica SP8 confocal microscope with a resonant scanner was used for imaging. Spontaneous calcium activity was recorded for 2 min (10 frames per second) in 6-9 fields per well, and for each field the distance from the spheroid was measured. (+)-tubocurarine chloride pentahydrate (curare; Sigma-Aldrich) was used at a final concentration of 100 µM.

Glutamate uncaging and optogenetic stimulation. Intact assembloids were imaged under environmentally controlled conditions (37° C., 5% CO2) using a 5× objective in a confocal microscope (Leica SP8). Assembloids, still in transwells, were incubated in the environmentally controlled chamber for 20-30 minutes before imaging. For glutamate uncaging experiments, MNI-caged-L-glutamate (1490, Tocris) was used at a final concentration of 3.3 mM in culture medium (see above). The FRAP software module of the Leica SP8 confocal microscope was used to uncage glutamate using UV light (405 nm). At a frame rate of 14.7 frames/sec, a typical stimulation experiment consisted of 500 frames acquired during pre-stimulation, 5 frames of UV stimulation (in specified region of interest, ROI) and 200 frames acquired during poststimulation. For optogenetic stimulation, five pulses of light (625 nm, 68 ms in duration each and ~68 seconds apart) were delivered using an optical fiber-coupled LED (400 µmdiameter, 13.2 mW; Thorlabs) that was directed towards the hCS. Pulses were generated by a CYCLOPS LED driver coupled with the Leica SP8. (+)-tubocurarine chloride pentahydrate (curare; Sigma-Aldrich) was used at a final concentration of 100 µM. NBQX (Tocris) and APV (Tocris) were used at a final concentration of 50 µM each.

Cryopreservation and immunohistochemistry. Cryopreservation and immunocytochemistry in hCS and hSpS was performed as previously described. Briefly, neural spheroids were fixed in 4% paraformaldehyde (PFA in PBS, Electron Microscopy Sciences) for 2 hours. Early spheroids (>25 days) were fixed for 30 minutes. Fixation was followed by three PBS washes, sucrose cryopreservation (30% sucrose in PBS for 24-48 hours), embedding in 1:1, 30% sucrose:OCT (Tissue-Tek OCT Compound 4583, Sakura Finetek) and freezing. For immunocytochemistry, 16 µm thick sections were cut using a cryostat (Leica). PCW17 cryosections were 30 µm thick. Cryosections were then washed with PBS to remove excess OCT, blocked for 1 h at room temperature (10% normal donkey serum (NDS), 0.3% Triton X-100 diluted in PBS), and incubated overnight at 4° C. with primary antibodies in blocking solution. Next day, cryosections were washed with PBS and then incubated with secondary antibodies for 1 h at room temperature. Alexa Fluor secondary antibodies (Life Technologies) diluted in blocking solution at 1:1,000 were used. For neuromuscular junction staining, cryosections were incubated for 30 minutes with anti-bungarotoxin (BTX) conjugated to Alexa Fluor-647 in blocking solution (1:500) after secondary antibody incubation. Following washes with PBS, nuclei were visualized with Hoechst 33258 (Life Technologies). Finally, slides were mounted for microscopy with cover glasses (Fisher Scientific) using Aquamount (Polysciences) and imaged on a Zeiss M1 Axioscope, Keyence fluorescence microscope or Leica TCS SP8 confocal microscope. Images were processed in ImageJ (Fiji). The same procedure was followed for immunocytochemistry of 2D hSkM.

Real-time quantitative PCR (qPCR). For qPCR analysis of spheroids, at least 2-3 spheroids were pooled per sample. mRNA was isolated using the RNeasy Mini kit and RNase-Free DNase set (Qiagen), and template cDNA was prepared by reverse transcription using the SuperScript III First-Strand Synthesis SuperMix for qRT-PCR (Life Technologies). qPCR was performed using Sybr Green (Roche) on a ViiA7 machine (Applied Biosystems, Life Technologies).

Single-cell gene expression (BD Rhapsody system). To capture single cell transcriptomic information of hiPS cell derived hSpS, we used the BD Rhapsody system (formerly known as BD Resolve) (BD Biosciences) as previously reported. hSpS with or without DAPT exposure were dissociated enzymatically into single cells at day 45 of differentiation and processed on the same day. Ten spheroids for each condition were combined, the proportion of live cells was estimated using a fluorescent assay (~90%) and all cells were used for further processing. Single-cell suspension of ~10,000 cells were captured from all isolated cells, without selection, on an array of >200,000 microwells through a limited dilution approach. Beads with oligonucleotide barcodes were added to saturation so that a bead was paired with a cell in a microwell. After exposure to cell lysis buffer, poly-adenylated RNA molecules hybridized to the beads. Beads were retrieved into a single tube for reverse transcription. Upon cDNA synthesis, each cDNA molecule was tagged on the 5' end (that is, the 3' end of a mRNA transcript) with a molecular index and cell label indicating its cell of origin. Whole transcriptome libraries were prepared from 40% of the captured cells by subsampling the Rhapsody beads that were then subject to second strand cDNA synthesis, adaptor ligation, and universal amplification using twenty two cycles of PCR. The rest of the beads were archived. Sequencing libraries were prepared using random priming PCR of the whole-transcriptome amplification products to enrich the 3' end of the transcripts linked with the cell label and molecular indices. The libraries were sequenced on HiSeq4000 (Illumina) using 101×2 chemistry. The BD Rhapsody analysis pipeline was used to process sequencing data (.fastq files). Cell labels and molecular indices were identified, and gene identity was determined by alignment against the gencode comprehensive hg19 reference. A table containing molecule counts per gene per cell was the output. Gene expression profiles of 4,175 and 3,173 cells were recovered for hSpS with or without DAPT, respectively, with an average number of reads of ~17,000, ~2,400 molecules and ~1,400 number of genes detected per cell with average molecular index coverage (that is, the number of times a molecule was sequenced) of 4.8. Analysis of the single cell transcriptome profiles was performed with $BD_{TM}$ Data View as we previously described. Cells with mitochondrial gene (with a gene symbol starting with MT) content >30%, were discarded, retaining a total of 7,888 cells from both samples. We extracted the expression profiles of the 1,278 genes that define the 10 populations in hSpS and conducted tSNE projection on the filtered data.

Electrophysiology. Sections of hSpS (day 45-75) for electrophysiology were obtained as previously described19. In brief, spheroids were incubated in bicarbonate-buffered aCSF at 23° C. and equilibrated with a mixture of 95% O2 and 5% CO2. The aCSF solution contained: 126 mM NaCl, 26 mM $NaHCO_3$, 10 mM glucose, 2.5 mM KCl, 1.25 mM NaH2PO4, 1 mM MgSO4 and 2 mM CaCl2. Slicing was performed using a Leica VT1200 vibratome. Immediately after sectioning, slices were moved to a circulation chamber containing oxygenated aCSF at room temperature. 24 Patch-clamp recordings were performed from cells expressing the Hb9::GFP fluorescent reporter using an upright microscope (Slicescope, Scientifica). Recording electrodes of borosilicate glass had a resistance of 8-10 MΩ when filled with internal solution. The internal solution contained: 145 mM K-gluconate, 0.1 mM CaCl2, 2.5 mM MgCl2, 10 mM HEPES, 0.2 mM EGTA, 4 mM Na-phosphocreatine. 4/7 cells were able to fire repetitive action potentials. Data were collected using a 1550A digitizer (Molecular Devices), a 700B patch-clamp amplifier (Molecular Devices) and acquired with pClamp 10.7 software (Molecular Devices). Data were low-pass filtered at 10 kHz and digitized at 20 kHz. Data averaging, digital subtraction of null traces, and current peak detection were performed using clampfit (Molecular Devices).

Data analysis. Projection quantification. hCS-derived AAV-hSYN1::eYFP projections were quantified using Image J (Fiji). ROIs were manually drawn to cover the area on the hSpS or hCS to be measured in max projection confocal stacks. Both the brightfield and fluorescent channels were used to draw the ROIs. Following background subtraction (50 rolling ball radius), FeatureJ Hessian filter and contrast enhancement (0.4 saturated), the percentage of YFP+pixels over total area of hSpS or hCS was calculated in binary images.

Calcium imaging. Calcium imaging data was processed using ImageJ (Fiji) and custom MATLAB routines. ROIs corresponding to hSkM fibers were automatically generated using the analyze particles plugin on average intensity projections (300 frames) using ImageJ (Fiji). A total number of 798 (hSkM condition), 652 (hCS+hSkM condition), 1006 (hSpS+hSkM condition) and 727 (hSpS+hSkM+curare condition) hSkM fibers were analyzed. Following ROI registration, raw time-series movies were transformed to relative changes in fluorescence: $dF/F(t)=(F(t)-F0)/F0$, where F0 represented the 5th percentile value of the time series of each ROI. To remove slow fluctuations originating from the summation of multiple events, we first high-passed filtered the ROI's dF/F(t) functions (dF/F(t)'. Calcium candidate events were detected whenever the ROI's dF/F(t) crossed a threshold of 7 median absolute deviations (MAD). Calcium events are typically characterized by a sharp rise followed by slower decay. To capture these features, we only considered events that follow this behavior. Event time was set to the time the event crossed the threshold.

Contraction analysis. Muscle contraction of 3D hSkM was quantified using the automated, open-source ImageJ plugin MUSCLEMOTION. MUSCLEMOTION quantifies movement by subtracting the summed, absolute changes in pixel intensity between a reference frame and the frame of interest. Because each imaging field consists of a large area containing multiple muscle fibers, several fibers may be moving simultaneously and summation of pixel intensities in these cases may result in non-changing summed values. Therefore, to reduce the chance of subtraction of pixel values, each imaging field was divided into 16 subfields and the analysis was performed in each of the subfields individually. For the analysis of spontaneous contractions, event detection was performed using custom MATLAB routines. Events over 5 median absolute deviations (MAD) were counted as a contraction event. Correlation between subfields in a field was calculated in MATLAB by computing a nonnormalized covariance calculation. The mean covariance per field was plotted. For the quantification of stimulation experiments of assembloids, pixel intensity analysis was performed with MUSCLEMOTION as described above. Displacement over time was calculated by normalizing all values to 500 frames preceding stimulation. If different fields (i.e. areas) were stimulated per assembloid, then these were plotted separately. If the same field was stimulated more than once, values were averaged and plotted as one point. For optogenetic stimulation, only the first trial was used for quantification, and data values resulting from each of the five pulses of light were averaged.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for producing functionally integrated human cortico-spinal-muscle assembled spheroids in vitro, the method comprising:
   (i) inducing in a human pluripotent stem cell suspension culture a neural fate to provide a first spheroid of neural progenitor cells and a second spheroid of neural progenitor cells;
   (ii) differentiating the neural progenitor cells in the first spheroid to differentiate into human spinal cord spheroids (hSC), and culturing the hSC with human skeletal muscle cells (hSkM) under integrating conditions to generate hSC-hSkM spheroids;
   (iii) differentiating the neural progenitor cells in the second spheroid to differentiate into human cortical spheroids (hCS);
   (iv) culturing the hCS and hSC-hSkM under conditions permissive for spheroid fusion while maintaining for an extended period of time in neural medium; wherein a functionally integrated human cortico-spinal-muscle assembled spheroid is differentiated comprising interacting glutamatergic projection neurons, motor neurons, interneurons, and muscle cells.

2. The method of claim 1, wherein the glutamatergic projection neurons, the motor neurons, and the interneurons of the functionally integrated human cortico-spinal-muscle assembled spheroid comprise at least one allele associated with a neurologic or neuromuscular disorder.

3. The method of claim 1, wherein the pluripotent stem cells are induced pluripotent stem cells.

4. The method of claim 1, wherein the pluripotent stem cell suspension culture is induced to a neural fate by culturing intact colonies of the pluripotent stem cells in medium comprising an effective dose of one or more SMAD inhibitor.

5. The method of claim 4, wherein the medium comprises a dose of dorsomorphin and SB-431542 effective to induce pluripotent stem cells to a neural fate.

6. The method of claim 5, wherein the suspension culture is feeder layer free.

7. The method of claim 1, wherein the pluripotent stem cells are differentiated into the first spheroid of neural progenitors and the second spheroid of neural progenitors by culture in a neural medium comprising a dose of FGF2 and EGF.

8. The method of claim 7, further comprising differentiating the first spheroid of neural progenitors by supplementing a neural medium with an effective dose of an SHH pathway agonist and retinoic acid, optionally supplemented with a gamma secretase inhibitor.

9. The method of claim 8, wherein the first spheroid of neural progenitors are then cultured in the neural medium comprising an effective dose of BDNF; IGF; L-ascorbic acid; and cAMP to mature human spinal cord spheroids.

10. The method of claim 9, wherein the mature human spinal cord spheroids are co-cultured with human skeletal muscle cells, which are derived from hiPSC or isolated from primary tissue, cultured in gel or on top of a gel matrix.

11. The method of claim 7, wherein the human cortical spheroids are differentiated by culturing the second spheroid of neural progenitor cells in a neural medium comprising an effective dose of BDNF and NT3.

12. The method of claim 1, further comprising maintaining functionally integrated human cortico-spinal-muscle assembled spheroids thus produced for an extended period of time in neural medium lacking growth factors.

13. A population of cells isolated from functionally integrated human cortico-spinal-muscle assembled spheroids produced by the method of claim 1.

14. A method for determining the effect of a candidate agent on human cortico-spinal-muscle circuits, the method comprising:
   contacting the candidate agent with one or a panel of functionally integrated human cortico-spinal-muscle assembled spheroids differentiated from induced human pluripotent stem cells (hiPSC) according to the method of claim 1, or a population of cells isolated therefrom; and
   determining the effect of the agent on morphologic, genetic or functional parameters.

15. The method of claim 14, wherein the panel of functionally integrated human cortico-spinal-muscle assembled spheroids comprises at least 2 differing genotypes.

16. The method of claim 14, wherein the effect on neuromuscular activity is determined.

17. An in vitro generated functionally integrated human cortico-spinal-muscle assembled spheroid produced by the method of claim 1.

* * * * *